(12) United States Patent
Kawashima et al.

(10) Patent No.: US 7,736,316 B2
(45) Date of Patent: Jun. 15, 2010

(54) ULTRASONIC DIAGNOSIS APPARATUS

(75) Inventors: Tomonao Kawashima, Tokyo (JP); Saori Obata, Tokyo (JP); Shun Yokoi, Tokyo (JP)

(73) Assignee: Olympus Corporation, Tokyo (JP)

( * ) Notice: Subject to any disclaimer, the term of this patent is extended or adjusted under 35 U.S.C. 154(b) by 662 days.

(21) Appl. No.: 11/589,601

(22) Filed: Oct. 30, 2006

(65) Prior Publication Data

US 2007/0078343 A1    Apr. 5, 2007

Related U.S. Application Data

(63) Continuation of application No. PCT/JP2005/007926, filed on Apr. 26, 2005.

(30) Foreign Application Priority Data

Apr. 30, 2004    (JP)    ............................. 2004-135896

(51) Int. Cl.
    *A61B 8/00* (2006.01)
(52) U.S. Cl. ...................... 600/443; 382/131
(58) Field of Classification Search ................. 600/443; 382/131
    See application file for complete search history.

(56) References Cited

U.S. PATENT DOCUMENTS

| 5,479,927 | A  | * | 1/1996 | Shmulewitz | ................ | 600/445 |
| 6,248,074 | B1 |   | 6/2001 | Ohno et al. | | |
| 7,110,583 | B2 | * | 9/2006 | Yamauchi | .................... | 382/128 |
| 2003/0073904 | A1 | * | 4/2003 | Moriya et al. | ............... | 600/439 |
| 2003/0231789 | A1 |   | 12/2003 | Willis et al. | | |

FOREIGN PATENT DOCUMENTS

| EP | 1 354 557 A1 | 10/2003 |
| EP | 1 504 721 A1 | 2/2005 |
| EP | 1 543 776 A1 | 6/2005 |
| JP | 10-151131 | 6/1998 |
| JP | 2000-023979 | 1/2000 |
| JP | 2000-51217 | 2/2000 |
| JP | 2000-081303 | 3/2000 |
| JP | 2001-340335 | 12/2001 |

(Continued)

OTHER PUBLICATIONS

Okuma et al., "Real-time virtual sonography ni Tsuite", Journal of Medical Ultrasonics, Apr. 15, 2003, vol. 30 Zokango, p. S151, together with English Language Translation.

(Continued)

*Primary Examiner*—Long V Le
*Assistant Examiner*—Saurel J Selkin
(74) *Attorney, Agent, or Firm*—Scully, Scott, Murphy & Presser, P.C.

(57) ABSTRACT

An ultrasonic diagnosis apparatus includes an image processing controlling unit that creates a guide image which corresponds to an anatomical position and orientation of a two-dimensional ultrasound image of an interior of a subject based on anatomical image data which is previously stored as anatomical image data of a human body; and a display unit that outputs and displays various types of images including the guide image and the two-dimensional ultrasound image so that plural images are simultaneously output and displayed.

21 Claims, 23 Drawing Sheets

FOREIGN PATENT DOCUMENTS

| | | |
|---|---|---|
| JP | 2002-363101 | 9/2002 |
| JP | 2003-305044 | 10/2003 |
| WO | WO 2004/028374 A1 | 4/2004 |
| WO | WO 2004/028375 A1 | 4/2004 |

OTHER PUBLICATIONS

Arai et al., "Real time virtual sonography no Kaihatsu", Journal of Medical Ultrasonics, Apr. 15, 2003, vol. 30, Zokango, p. S151, together with English Language Translation.

Comeau, R.M., et al. "Intraoperative US in Interactive Image-guided Neurosurgery1", Image and Therapeutic Technology, A Review Publication of the Radiological Society of North America, Inc, Jul.-Aug. 1998, pp. 1019-1027, vol. 18, No. 4, XP002533708.

Herring, J.L., et al., "Surface-Based Registration of CT Images to Physical Space for Image-Guided Surgery of the Spine: A Sensitivity Study", IEEE Transactions on Medical Imaging, Oct. 1998, pp. 743-752, vol. 17, No. 5.

Japanese Office Action dated Feb. 2, 2010 with Partial English Translation.

* cited by examiner

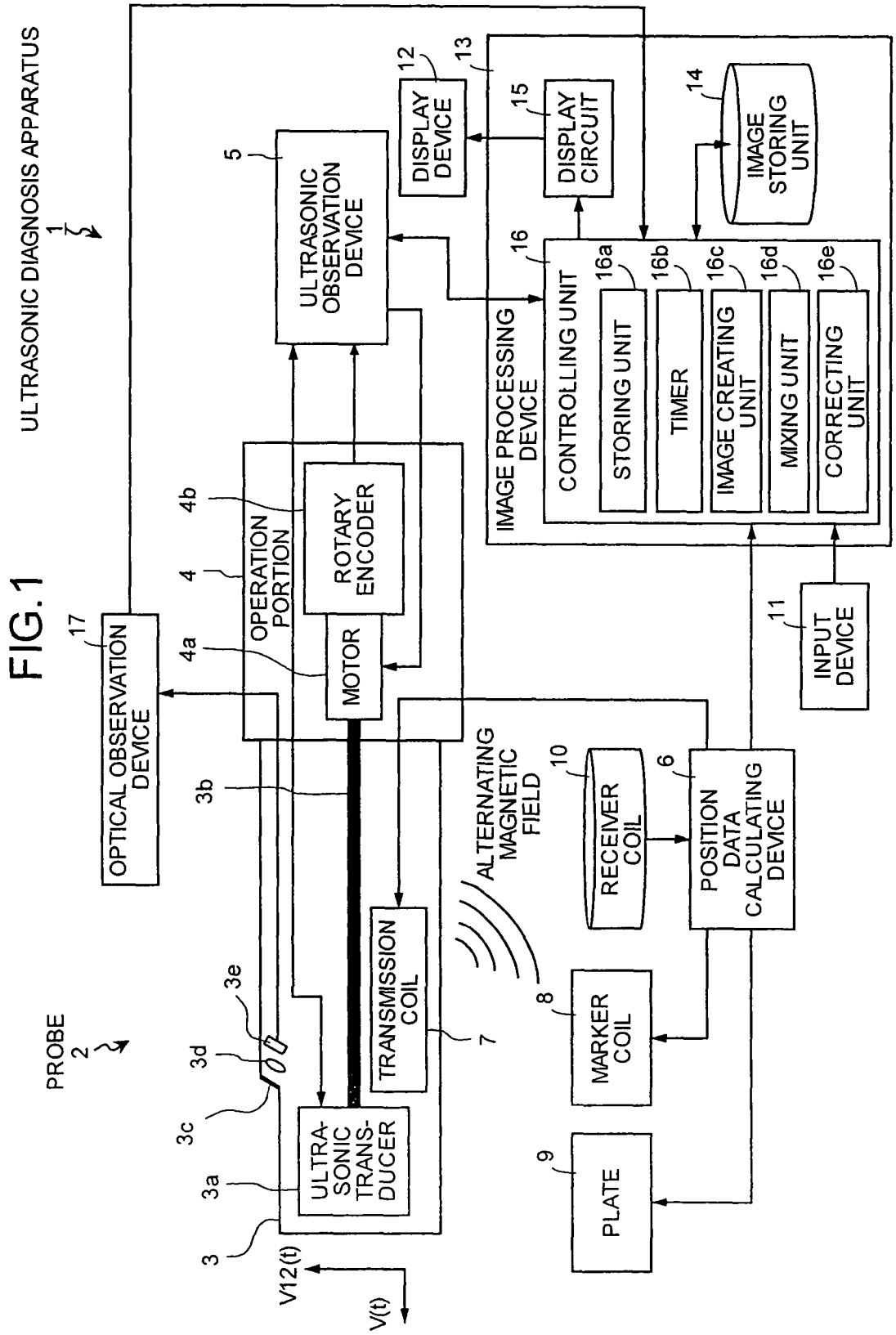

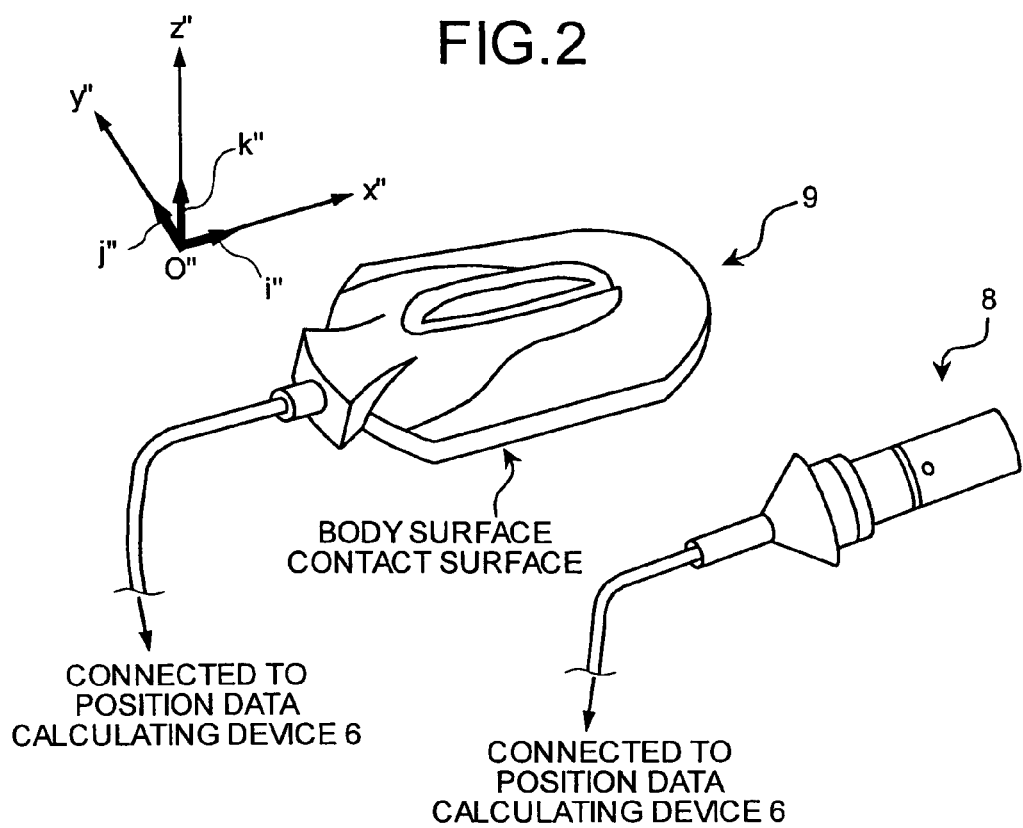
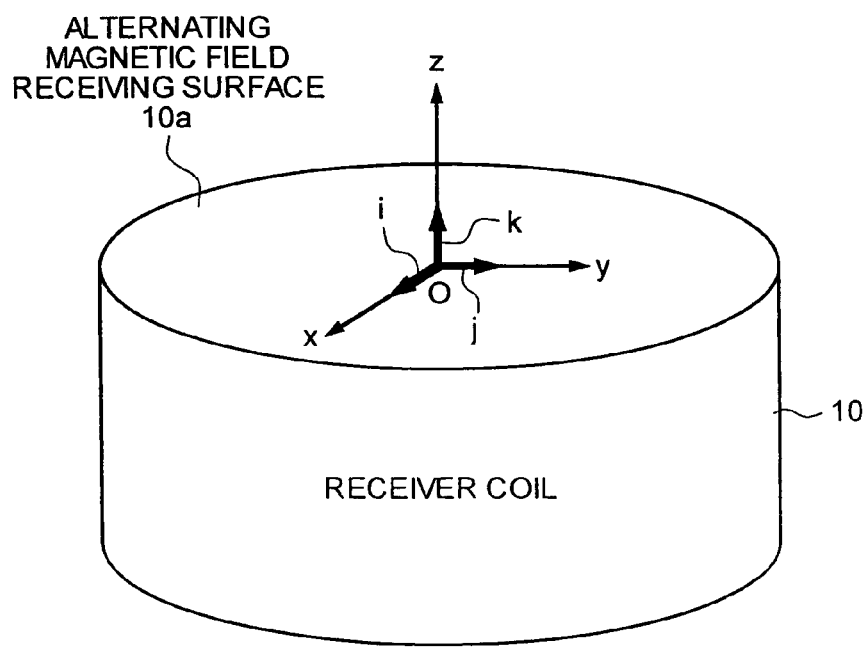

ULTRASONIC DIAGNOSIS APPARATUS

CROSS-REFERENCE TO RELATED APPLICATIONS

This application is a continuation of PCT international application Ser. No. PCT/JP2005/007926 filed Apr. 26, 2005 which designates the United States, incorporated herein by reference, and which claims the benefit of priority from Japanese Patent Application No. 2004-135896, filed Apr. 30, 2004, incorporated herein by reference.

BACKGROUND OF THE INVENTION

1. Field of the Invention

The present invention relates to an ultrasonic diagnosis apparatus that irradiates an interior of a living body with ultrasound in a radial manner, receives and scans an echo of the ultrasound, obtains ultrasound image data from the scanning, and outputs and displays an ultrasound image of the interior of the living body based on the obtained ultrasound image data.

2. Description of the Related Art

Conventionally, an ultrasonic diagnosis apparatus is widely used as a medical diagnosis apparatus that allows for a real-time observation of an interior of a living body. The ultrasonic diagnosis apparatus performs a sector scan by irradiating the interior of the living body with ultrasound and by receiving an ultrasound echo from a living tissue of the living body to generate and output an ultrasound image of the interior of the living body. On using the ultrasonic diagnosis apparatus, an operator recalls known anatomic positional relations of respective organs and tissues inside the living body and keeps the same in mind. While observing the ultrasound image, the operator estimates an anatomic position of a currently observed region inside the living body based on the above knowledge and makes medical diagnosis on the living body. For a support of such diagnosis, one conventionally proposed ultrasonic diagnosis apparatus outputs and displays a guide image to help the operator to track down the anatomic position of a region inside the living body whose ultrasound image the operator currently observes.

For example, the above mentioned conventional ultrasonic diagnosis apparatus includes an ultrasonic probe which is arranged outside a subject and irradiates an interior of the subject, i.e., the living body, with ultrasound from outside the subject, and an anatomical chart database in which anatomic illustrative images are stored. The conventional ultrasonic diagnosis apparatus detects position and orientation of an ultrasonic transducer provided in the ultrasonic probe, selects an illustrative image, which matches with anatomic position and orientation extracted from the detected position and orientation, from the anatomical chart database, and outputs and displays the selected illustrative image. Further, the operator adjusts a contact position and a contact orientation of the ultrasonic probe before starting the diagnosis so that a predetermined section (reference plane) of the living body coincides with a scanning plane of the ultrasonic probe. Thus, the conventional ultrasonic diagnosis apparatus can automatically select an illustrative image from the anatomical chart database according to the position and the orientation of the ultrasonic transducer (see Japanese Patent Laid-Open No. 2002-263101 (KOKAI)).

One manner of matching the reference plane and the scanning plane is: firstly, the ultrasonic diagnosis apparatus displays a bone structure chart which is formulated based on information of a constitution of a subject; then, an operator optionally sets the reference plane on the bone structure chart, and adjusts the contact position and the contact orientation of the ultrasonic probe so that the reference plane coincides with the scanning plane. Another manner of matching is: firstly, the ultrasonic diagnosis apparatus displays a bone structure chart corresponding to a current contact state of the ultrasonic probe, and an operator sets coordinates of the reference plane which coincides with the scanning plane of the ultrasonic probe on the bone structure chart. The ultrasonic diagnosis apparatus matches the scanning plane of the ultrasonic probe and the reference plane on the bone structure chart in the above described manners, thereby matching a coordinate system of the ultrasonic probe (coordinate system the ultrasonic diagnosis apparatus recognizes) with a coordinate system on the living body.

SUMMARY OF THE INVENTION

An ultrasonic diagnosis apparatus according to one aspect of the present invention performs a scan of an interior of a subject to obtain two-dimensional image data of the interior, detects a position and an orientation of a scanning plane of the scan according to which the two-dimensional image data is obtained, and creates and outputs a two-dimensional ultrasound image of the interior based on the position and the orientation detected and the two-dimensional image data. The ultrasonic diagnosis apparatus includes an image processing controlling unit that creates a guide image which corresponds to an anatomical position and orientation of the two-dimensional ultrasound image based on anatomical image data which is previously stored as anatomical image data of a human body; and a display unit that outputs and displays various types of images including the guide image and the two-dimensional ultrasound image so that plural images are simultaneously output and displayed.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 1 is a block diagram illustrating an exemplary structure of an ultrasonic diagnosis apparatus according to a first embodiment of the present invention;

FIG. 2 is a schematic diagram illustrating one example of a marker coil and one example of a plate;

FIG. 3 is a schematic diagram illustrating a state in which an orthogonal coordinate system is set on a receiver coil;

DETAILED DESCRIPTION OF THE PREFERRED EMBODIMENTS

Figure 4:
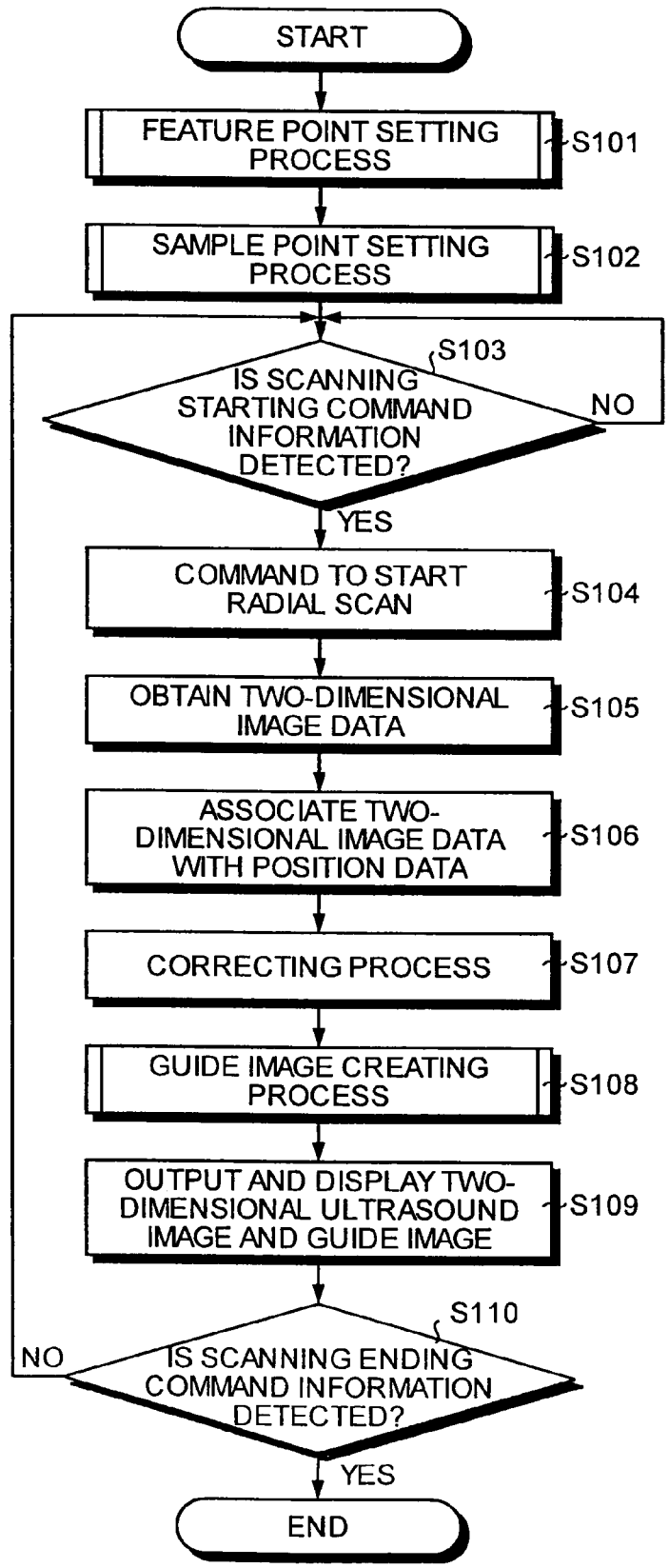
FIG. 4 is a flowchart illustrating a processing procedure up to an output, and display of a two-dimensional ultrasound image and a guide image in an aligned manner on one screen.

Exemplary embodiments of an ultrasonic diagnosis apparatus according to the present invention will be described in detail below with reference to the accompanying drawings. It should be noted that the present invention is not limited to the embodiments.

FIG. 1 is a block diagram illustrating an exemplary structure of an ultrasonic diagnosis apparatus according to a first embodiment of the present invention. In FIG. 1, an ultrasonic diagnosis apparatus 1 includes a probe 2 which has an insertion portion 3 to be inserted inside a subject and an operation portion 4 to be employed for an operation of the insertion portion 3, an ultrasonic observation device 5, a position data calculating device 6, a transmission coil 7 having plural coils, a marker coil 8, a plate 9 having plural coils, a receiver coil 10, an input device 11, a display device 12, an image processing device 13, and an optical observation device 17. An ultrasonic transducer 3a is rotatably embedded at a distal end side of the insertion portion 3, and the operation portion 4 is arranged at a back end of the insertion portion 3. Near the ultrasonic transducer 3a, the transmission coil 7 is arranged in a detachable manner. Further, the insertion portion 3 includes a shaft 3b which serves as a rotation axis of the ultrasonic transducer 3a, and the operation portion 4 includes a motor 4a and a rotary encoder 4b. The motor 4a is connected to the ultrasonic transducer 3a via the shaft 3b. The rotary encoder 4b is connected to the motor 4a. The ultrasonic observation device 5 is electrically connected to the ultrasonic transducer 3a, the motor 4a, and the rotary encoder 4b via a power switch (not shown) provided in the operation portion 4, a cable, or the like. The position data calculating device 6 is electrically connected to the transmission coil 7, the marker coil 8, the plate 9, and the receiver coil 10 via a cable or the like. Further, the probe 2 includes an optical observation window 3c which is made with a cover glass, a lens 3d, a CCD (Charge Coupled Device) camera 3e, and an illumination light irradiation window (not shown) which irradiates an inside of a body cavity with illumination light. The CCD camera 3e is electrically connected with the optical observation device 17 via a cable or the like. The image processing device 13 is electrically connected to the ultrasonic observation device 5, the position data calculating device 6, the input device 11, the display device 12, and the optical observation device 17 via a cable or the like.

In the probe 2, the ultrasonic transducer 3a rotates and repeatedly and radially transmits/receives ultrasound while the insertion portion 3 is inside the subject, whereby a radial scan of the interior of the subject is performed. The insertion portion 3 is formed with a flexible member, and has an elongated cylindrical shape as appropriate for the insertion into the subject. The ultrasonic transducer 3a is made from piezoceramic such as barium titanate, and lead zirconate titanate. The ultrasonic transducer 3a has a function of converting a pulsing voltage applied from the ultrasonic observation device 5 into ultrasound by inverse piezoelectric effect, and a function of converting a reflective wave (echo) of the ultrasound into electric signals (scan signals) by piezoelectric effect and outputting the electric signals to the ultrasonic observation device 5. The shaft 3b is a flexible shaft, and functions as a flexible rotation axis which conveys the rotary drive of the motor 4a to the ultrasonic transducer 3a. Hence, the ultrasonic transducer 3a rotates around the rotation axis which lies substantially in the same direction as a direction of the insertion of the insertion portion 3 into the subject.

The operation portion 4 has a function of bending the distal end of the insertion portion 3 in response to a manipulation by an operator, i.e., a person who performs an intracorporeal observation or a diagnosis of the subject. The bent portion includes a portion where the ultrasonic transducer 3a and the transmission coil 7 are arranged. When the operator manipulates the power switch in the operation portion 4 or gives a predetermined command from the input device 11 via the image processing device 13 and the ultrasonic observation device 15, thereby turning a power supply on, the ultrasonic transducer 3a, the motor 4a, the rotary encoder 4b, and the ultrasonic observation device 5 are electrically connected. In this state, the ultrasonic observation device 5 can apply pulsing voltage (pulse voltage) of approximately 100 V to the ultrasonic transducer 3a, and driving direct current voltage of approximately 12 V to the motor 4a, while receiving electric signals from the rotary encoder 4b. The motor 4a gives rotary drive using the driving direct current voltage applied by the ultrasonic observation device 5 and conveys the rotary drive to the ultrasonic transducer 3a via the shaft 3b. Thus, the motor 4a rotates the ultrasonic transducer 3a around the shaft 3b as the rotation axis. Further, the rotary encoder 4b detects a rotation angle of the rotary drive by the motor 4a, and outputs electric signals (angle detection signals) corresponding to the detected rotation angle to the ultrasonic observation device 5.

The optical observation window 3c is arranged near the ultrasonic transducer 3a or the transmission coil 7, for example, at a position 0.5 cm away from the transmission coil 7. The above described illumination light irradiation window (not shown) passes the illumination light to illuminate the interior of the subject. An image of a surface of a lumen inside the subject passes through the optical observation window 3c and the lens 3d and is focused on the CCD camera 3e. The CCD camera 3e outputs electrical signals (CCD signals) corresponding to the focused image to the optical observation device 17. The optical observation device 17 creates data of the image of the surface of the lumen inside the body cavity of the subject based on the CCD signals sent from the CCD camera 3e, and outputs the resulting data as optical image data to a controlling unit 16 inside the image processing device 13.

The ultrasonic observation device 5 includes, for example, a detecting circuit, an amplifying circuit, an A/D converting circuit, and a coordinates converting circuit. The ultrasonic observation device 5 performs known processes such as an envelope detecting process, a logarithmic amplifying process, an A/D converting process, and a coordinates converting process from a polar coordinate system to an orthogonal coordinate system using scan signals sequentially received from the ultrasonic transducer 3a and angle detection signals received from the rotary encoder 4b. Thus, the ultrasonic observation device 5 sequentially creates one piece of two-dimensional image data for every portion of sequentially received scan signals, in other words, for every performance of the above described radial scan. Thereafter, the ultrasonic observation device 5 sequentially transmits the created two-dimensional image data to the image processing device 13. Here, the two-dimensional image data is digital image data which corresponds to a two-dimensional ultrasound image of the interior of the subject obtained by the radial scan. In the two-dimensional image data, a reference direction is set in a direction parallel to a two-dimensional image plane based on the above described angle detection signal. In the first embodiment, the reference direction will be referred to as a direction of twelve o'clock, i.e., upward direction of the two-dimensional ultrasound image, hereinafter.

When the operator turns the power switch (not shown) provided in the position data calculating device 6 on, the position data calculating device 6 supplies electric currents to the transmission coil 7, the marker coil 8, and the plate 9 via the cable or the like and receives the electric signals from the receiver coil 10. Specifically, the position data calculating device 6 excites respective coils forming the transmission coil 7, the marker coil 8, and the plate 9 at different frequencies. Thereafter, the position data calculating device 6 receives the electric signals from the receiver coil 10. The received electric signals correspond to respective alternating magnetic fields generated from the coils of the transmission coil 7, the marker coil 8, and the plate 9. The receiver coil 10 detects each of the alternating magnetic fields generated from the coils forming the transmission coil 7, the marker coil 8, and the plate 9, and converts the detected alternating magnetic fields into the electric signals. At the same time, the receiver coil 10 transmits the electric signals to the position data calculating device 6 as position detection signals.

The position data calculating device 6 divides the position detection signals from the receiver coil 10 with respect to each frequency, thereby dividing the received position detection signal with respect to each alternating magnetic field. In other words, the position data calculating device 6 obtains the position detection signal attributable to the alternating magnetic field of each coil forming the transmission coil 7, the marker coil 8, and the plate 9 by separating the received position detection signals. Then, the position data calculating device 6 calculates data (position data) of a position and an orientation of each of the transmission coil 7, the marker coil 8, and the plate 9 based on the respective obtained position detection signals, and transmits the calculated position data to the image processing device 13.

The transmission coil 7 includes a first coil and a second coil. An axis of winding (coil axis) of the first coil is fixed in a direction of the rotation axis of the ultrasonic transducer 3a, i.e., the direction of the insertion axis of the insertion portion 3 into the subject. An axis (coil axis) of the second coil is fixed in a direction of 12 o'clock of the two-dimensional ultrasound image, i.e., a reference direction based on the angle detection signal from the rotary encoder 4b, i.e., a direction perpendicular to the direction of the insertion axis. As described above, the transmission coil 7 is arranged in a detachable manner in the vicinity of the ultrasonic transducer 3a, i.e., a position approximately 0.5 to 1 cm away from the ultrasonic transducer 3a. Here, the transmission coil 7 is fixed so that a distance from the ultrasonic transducer 3a and an orientation of the transmission coil 7 are substantially constant. Therefore, the position and the orientation of each of the first coil and the second coil are fixed substantially constant with respect to the ultrasonic transducer 3a. The transmission coil 7 generates an alternating magnetic field when the position data calculating device 6 supplies electric currents to the first coil and the second coil. The position data calculating device 6, as described above, can obtain the position data on the position and the orientation of the ultrasonic transducer 3a based on each of the position detection signals corresponding to the respective alternating magnetic fields from the first coil and the second coil. When the transmission coil 7 is arranged near the ultrasonic transducer 3a, the transmission coil 7 may be arranged onto an outer wall of the insertion portion 3 in a detachable manner. It is desirable, however, that the transmission coil 7 be buried inside the insertion portion 3 in a detachable manner.

The marker coil 8 incorporates a coil which converts the electric currents supplied from the position data calculating device 6 into a predetermined alternating magnetic field. The marker coil 8 has a stick-like shape. The incorporated coil is arranged at a distal end side of the stick-like marker coil 8. When the position data calculating device 6 supplies electric currents to the marker coil 8 while the marker coil is in contact with a surface of the subject body, the marker coil 8 generates an alternating magnetic field which indicates a position near the body surface. The position data calculating device 6, as described above, can obtain the position data on the contact position on the surface of the subject body based on the position detection signal corresponding to the alternating magnetic field from the marker coil 8.

The plate 9 incorporates three coils that convert the electric currents supplied from the position data calculating device 6 into a predetermined alternating magnetic field. The plate 9 has a plate-like shape such as an oval shape so as to be easily attachable to the body surface of the subject. If the position data calculating device 6 supplies electric currents to the plate 9 while the plate is in contact with the body surface of the subject, the plate 9 generates an alternating magnetic current that indicates a position near the body surface. Further, the three coils of the plate 9 are arranged in the plate 9 in such a manner that coil axes of the respective coils are not located linearly. Depending on the arrangement of the three coils, an orthogonal coordinate system x"y"z", in which x"-axis, y"-axis, and z"-axis intersect with each other at right angles at an origin O", is previously set in the plate 9. The orthogonal coordinate system x"y"z" is fixed on the plate 9. Hence, when the plate 9 moves, the orthogonal coordinate system x"y"z" moves accordingly. The setting of the orthogonal coordinate system x"y"z" to the plate 9 will be described later.

The receiver coil 10 includes plural coils. The receiver coil 10 detects each of the alternating magnetic fields generated from the transmission coil 7, the marker coil 8, and the plate 9, and converts the detected alternating magnetic fields into the position detection signals. At the same time, the receiver coil 10 transmits the generated position detection signals to the position data calculating device 6. Further, an orthogonal coordinate system xyz, in which three axes, i.e., x-axis, y-axis, and z-axis intersect at right angles with each other at an origin O, is set on the receiver coil 10. The orthogonal coordinate system xyz is fixed to the receiver coil 10. Since the receiver coil 10 does not move in a subsequent operation, a position and an orientation of the orthogonal coordinate system xyz are fixed in a space. The orthogonal coordinate system xyz is employed to represent the position data calculated by the position data calculating device 6, i.e., positions inside the subject body detected by the transmission coil 7, the marker coil 8, and the plate 9, and the position and the orientation of the ultrasonic transducer 3a. The setting of the orthogonal coordinate system xyz on the receiver coil 10 will be described later.

The input device 11 is realized as one or a combination of a keyboard, a touch panel, a track ball, a mouse, a joystick, and the like. The input device 11 is employed to input various types of information to the image processing device 13. The input information includes, for example, command information to indicate a start, an end, or a switching of various processes and operations performed by the ultrasonic diagnosis apparatus 1, such as radial scan described above, and display of various types of images on the display device 12, coordinate information concerning the three-axis orthogonal coordinate system set on the receiver coil 10, and coordinate information of a feature point described later. When the keyboard or the touch panel is employed, the operator inputs or selects desired command information or coordinate information, or, the operator directly inputs from information menu or a coordinate position as displayed on the display device 12 or the touch panel. Thus, the desired command information or the coordinate information is input. On the other hand, when the track ball, the mouse, or the joystick is employed, the operator selects desired command information from the information menu displayed on the display device 12, or the operator directly designates a coordinate position as displayed on the display device 12. Thus, the desired command information or the coordinate information is input. Specifically, the operator manipulates the track ball, the mouse, or the joystick, to move a cursor or the like displayed on the display device 12 to a position where an option of desired command information or a desired coordinate position is displayed, and performs a click manipulation. Thus, desired command information or coordinate information is input.

The image processing device 13 is realized with a known computer, and has an image storing unit 14, a display circuit 15, and the controlling unit 16. The image storing unit 14 is realized with various data readable and writable storage device such as various IC memories such as an EEPROM, or a flash memory, a hard disk drive, or a magnet-optical disc drive. The image storing unit 14 stores various types of image data such as the two-dimensional image data supplied from the controlling unit 16, and the guide image data described later under the control of the controlling unit 16. Here, the image storing unit 14 can store position data of each of the various pieces of image data such as the two-dimensional image data, or the guide image data in association with the image data under the control of the controlling unit 16. Further, the image storing unit 14 transmits the stored various types of image data or the like to the controlling unit 16 under the control of the controlling unit 16.

Further, the image storing unit 14 previously stores a slice image data group which includes plural pieces of slice image data which is anatomic image data of a section of a living body. In the slice image data group, an orthogonal coordinate system x'y'z', in which three axes, i.e., x'-axis, y'-axis, and z'-axis intersect with each other at right angles at an origin O', is previously set. In other words, the slice image data group is stored in the image storing unit 14 as arranged on the orthogonal coordinate system x'y'z'. Thus, the controlling unit 16 can read out the slice image data or the slice image data group as associated with the orthogonal coordinate system x'y'z'.

To obtain the slice image data, a frozen human body other than that of the subject is sliced at a pitch of 1 mm in a parallel direction, for example, and each sliced portion is imaged to obtain photograph data of an approximately 40-cm-square. Pixels of the photograph data are sorted by organ, and the pixels are colored differently for each organ. Thus obtained image data is the slice image data. One side of the photograph data is set to approximately 40 cm, so that an overall transverse section, i.e., a section perpendicular to a body axis of the human body can be accommodated therein.

The display circuit 15 performs a D/A converting process or the like on the various types of image data supplied from the controlling unit 16 under the control of the controlling unit 16, and converts the supplied image data into image signals so that the data can be displayed on the display device 12. Thereafter, the display circuit 15 transmits the image signals to the display device 12. The display device 12 outputs and displays one or more of various images corresponding to the various image data based on the image signals sent from the display circuit 15 by switching the display images, or by aligning the plural images side by side. For example, the display device 12 outputs and displays a two-dimensional ultrasound image corresponding to two-dimensional image data generated by the ultrasonic observation device 5, by receiving image signals corresponding to the two-dimensional image data from the display circuit 15. Further, the display device 12 outputs and displays an optical image of a surface of a lumen, for example, inside the subject corresponding to optical image data generated by the optical observation device 17, by receiving image signals corresponding to the optical image data from the display circuit 15. Here, a single optical image may be displayed, or alternatively, plural optical images are displayed in turn or in an aligned manner under the control of the controlling unit 16.

The controlling unit 16 has a storing unit 16a that includes a ROM which previously stores various data such as a processing program and a RAM which temporarily stores data such as operation parameters, and a CPU that executes the processing program. The controlling unit 16 controls various operations of the ultrasonic diagnosis apparatus 1 concerning the above described radial scan, and an image display operation of the display device 12. The controlling unit 16 performs control of an input/output of various pieces of information supplied from the ultrasonic observation device 5, the position data calculating device 6, and the input device 11. At the same time, the controlling unit 16 controls an operation of the ultrasonic observation device 5 and an operation of each element of the image processing device 13. Further, the storing unit 16a temporarily stores various pieces of image data, various pieces of information supplied from the input device 11, various pieces of position data supplied from the position data calculating device 6, and the like, under the control of the controlling unit 16.

The controlling unit 16 further includes a timer 16b, an image creating unit 16c, a mixing unit 16d, and a correcting unit 16e. The timer 16b functions to notify the controlling unit 16 of a time t at a predetermined timing under the control of the controlling unit 16. For example, the timer 16b notifies the controlling unit 16 of a time at which the controlling unit 16 receives sample point setting command information described later from the input device 11, or a time at which the controlling unit 16 receives the two-dimensional image data from the ultrasonic observation device 5 under the control of the controlling unit 16.

The image creating unit 16c functions to set a point (hereinafter referred to as feature point) on the orthogonal coordinate system x'y'z' set on the above described slice image data group based on the coordinate information supplied from the input device 11 under the control of the controlling unit 16. Specifically, the operator inputs feature point coordinate information using the input device 11 while confirming a slice image on the display device 12. The controlling unit 16 detects the feature point coordinate information supplied by the operator. At this time, the image creating unit 16c sets feature points on coordinates on the orthogonal coordinate system x'y'z' based on the feature point coordinate information under the control of the controlling unit 16. Thereafter, the image creating unit 16c sets a three-axis coordinate system $P_1'P_2'P_3'$ using four points (feature points $P_0'$, $P_1'$, $P_2'$, and $P_3'$) among plural, i.e., at least four set feature points. The controlling unit 16 stores coordinate data of the feature points set by the image creating unit 16c in association with the slice image data group described above in the image storing unit 14.

The feature point is set as a point that indicates an anatomically characteristic region. For example, it is desirable that the feature point be set at an anatomically characteristic region, such as an ensiform cartilage, a right end or a left end of a pelvis, a pylorus, a duodenal papilla (outlet of common bile duct to a duodena), or a cardiac orifice. The feature point coordinate information is coordinate information for the setting of the feature point as a point on the orthogonal coordinate system x'y'z'. The three-axis coordinate system $P_1'P_2'P_3'$ is a coordinate system having three axes and having one of the four feature points (for example, feature point $P_0'$) as an origin. The three axes are determined by vectors passing through the origin (i.e., feature point $P_0'$) and the respective remaining feature points $P_1'$, $P_2'$, and $P_3'$. Therefore, the three axes do not necessarily intersect with each other at right angles.

Further, the image creating unit 16c functions so as to set a point on the orthogonal coordinate system xyz set on the receiver coil 10 as described above based on the information supplied from the input device 11 under the control of the controlling unit 16. Specifically, the operator inputs command information (sample point setting command information) to designate setting of a point using the input device 11 while keeping the marker coil 8 and the plate 9 in contact with the body surface of the subject, or while manipulating the probe 2 and confirming the optical image on the display device 12. The controlling unit 16 detects the input sample point setting command information. Here, the image creating unit 16c sets a point (hereinafter referred to as sample point) on the orthogonal coordinate system xyz using the position data supplied from the position data calculating device 6 based on the sample point setting command information under the control of the controlling unit 16. Thereafter, the image creating unit 16c sets a three-axis coordinate system $P_1P_2P_3$ using four sample points ($P_0$, $P_1$, $P_2$, $P_3$) among the at least four set sample points.

The sample points $P_0$, $P_1$, $P_2$, $P_3$ are points that indicate regions that anatomically correspond to the above described feature points $P_0'$, $P_1'$, $P_2'$, $P_3'$, respectively, and indicate particular regions on the body surface of the subject or the surface of lumen inside the subject. For example, if the sample point $P_0$ is on an ensiform cartilage of the subject, the feature point $P_0'$ is a point that indicates the ensiform cartilage in the slice image data group. Similarly, if the sample point $P_1$ is on the right end of the pelvis of the subject, the feature point $P_1'$ is a point that indicates the right end of the pelvis in the slice image data group; if the sample point $P_2$ is on the pylorus of the subject, the feature point $P_2'$ is a point that indicates the pylorus in the slice image data group; if the sample point $P_3$ is on the duodenal papilla of the subject, the feature point $P_3'$ is a point that indicates the duodenal papilla in the slice image data group. Further, the sample point has coordinate components that correspond to one of the position data of the transmission coil 7, i.e., the position data on the ultrasonic transducer 3a, the position data of the marker coil 8, and the position data of the plate 9 within the orthogonal coordinate system xyz. Further, the three-axis coordinate system $P_1P_2P_3$ is a coordinate system having three axes and one of the four sample points (for example, the sample point $P_0$) as the origin. The three axes are determined based on vectors that connect the origin (i.e., the sample point $P_0$) and the remaining sample points $P_1$, $P_2$, $P_3$, respectively. Therefore, the three axes do not necessarily intersect with each other at right angles.

Further, the image creating unit 16c, in response to the reception of the two-dimensional image data sent from the ultrasonic observation device 5 at the controlling unit 16 as a trigger, associates the two-dimensional image data with the position data from the position data calculating device 6 under the control of the controlling unit 16. For example, the image creating unit 16c associates the position data sent from the position data calculating device 6 with the two-dimensional image data sent from the ultrasonic observation device 5 substantially at the same timing with the reception of the two-dimensional image data by the controlling unit 16. Thus, the image creating unit 16c can set the position and the orientation of the two-dimensional image data.

Specifically, the position data calculating device 6 calculates a direction component with respect to the orthogonal coordinate system xyz of each of a position vector OC(t) of the position C(t) of the first coil, a direction vector V(t) corresponding to the direction of the coil axis of the first coil, a direction vector $V_{12}(t)$ corresponding to the direction of the coil axis of the second coil, respectively. The coil axis of the second coil is fixed in the direction of 12 o'clock of the two-dimensional ultrasound image, i.e., the reference direction which is determined based on the angle detection signal sent from the rotary encoder 4b as described above. Here, the position data calculating device 6 standardizes and outputs each of the direction vector V(t) and the direction vector $V_{12}(t)$ as a unit length vector. Thereafter, the position data calculating device 6 transmits the obtained direction component of each of the position vector OC(t), the direction vector V(t), and the direction vector $V_{12}(t)$ as the position data to the controlling unit 16. The image creating unit 16*c* associates the position data with the two-dimensional image data which the controlling unit 16 receives substantially at the same timing.

A two-dimensional image plane of the two-dimensional image data corresponds to the scanning plane of the above mentioned radial scan. Further, since the transmission coil 7 is arranged in the vicinity of the ultrasonic transducer 3*a* as described above, the position vector OC(t) can be regarded as the position vector of the rotation center of the ultrasonic transducer 3*a*. Further, since the direction of the coil axis of the first coil in the transmission coil 7 is fixed in the direction of the insertion axis, the direction vector V(t) can be regarded as a normal vector, i.e., a vector in a direction perpendicular to the two-dimensional ultrasound image. Since the direction of the coil axis of the second coil is fixed in the direction of 12 o'clock of the two-dimensional ultrasound image as described above, the direction vector $V_{12}(t)$ can be regarded as the vector in the direction of 12 o'clock of the two-dimensional image data. Therefore, a central position C(t), the position vector OC(t), the direction vector V(t), and the direction vector $V_{12}(t)$ are coordinates, a position vector, a normal vector, and a vector in the direction of 12 o'clock at the time t, respectively. The coordinates of the central position C(t), and the direction components of the vectors vary depending on the changes in the position or the orientation of the distal end of the insertion portion 3 as the time t elapses.

Further, the image creating unit 16*c* functions so as to create guide image data based on the slice image data group read out from the image storing unit 14 and the various types of position data supplied from the position data calculating device 6 under the control of the controlling unit 16. Specifically, the image creating unit 16*c* calculates relations between the position and the orientation of the three-axis coordinate system $P_1P_2P_3$ and the position and the orientation of the two-dimensional image plane on the orthogonal coordinate system xyz, which is uniquely determined by the position vector OC(t), the direction vector V(t), and the direction vector $V_{12}(t)$. Then, based on the result of the calculation, the image creating unit 16*c* finds a plane (hereinafter referred to as guide image plane) which is on the orthogonal coordinate system x'y'z' and which has the same positional and the orientational relations with the three-axis coordinate system $P_1'P_2'P_3'$ as the relations between the two-dimensional image plane on the orthogonal coordinate system xyz and the three-axis coordinate system $P_1P_2P_3$. The controlling unit 16 reads out a part, which corresponds to the guide image plane, from the data in the slice image data group in the image storing unit 14. The image creating unit 16*c* performs an interpolating process, a coordinate converting process, or the like on the read out data, and creates guide image data which corresponds to a sectional image along the guide image plane of the slice image data group in the image storing unit 14. Thereafter, the guide image data is supplied to the mixing unit 16*d*.

Here, the guide image data is image data of a section of a living body and anatomically corresponds to the two-dimensional image data created by the ultrasonic observation device 5. Therefore, a position and an orientation of an organ or the like displayed in an guide image output and displayed by the display device 12 based on the guide image data anatomically correspond to those in the two-dimensional ultrasound image that corresponds to the two-dimensional image data. For example, if the two-dimensional image data supplied from the ultrasonic observation device 5 is image data of a section of a head of pancreas viewed from a side of the duodena, the image creating unit 16*c* creates guide image data of the section of the head of pancreas viewed from the duodena as image data anatomically corresponding to the two-dimensional image data. These pieces of data correspond with each other, for the following reasons. Firstly, though the anatomical structure of the human body and the shapes of the organs are different from one person to another, the anatomical structure and the shape of an abdomen are expected to be approximately the same among different sexes though there can be a difference attributable to differences in constitution. Secondly, the four sample points $P_0$, $P_1$, $P_2$, and $P_3$ on the actual body surface of the subject, or on the surface of the lumen inside the subject anatomically correspond to the four feature points $P_0'$, $P_1'$, $P_2'$, and $P_3'$ set on the slice image data group. Thirdly, the positional and the orientational relations of the two-dimensional image plane and the three-axis coordinate system $P_1P_2P_3$ having the four sample points $P_0$, $P_1$, $P_2$, and $P_3$ are the same as the positional and the orientational relations of the guide image plane and the three-axis coordinate system $P_1'P_2'P_3'$ having four feature points $P_0'$, $P_1'$, $P_2'$, and $P_3'$. Because of the above-described three reasons, if a corresponding point R' on the guide image data is at the same position and has the same address as an optional point R on the two dimensional image data, the corresponding point R' corresponds to the same body part, the same organ, or the same living tissue as the optional point R in anatomical sense. Hence, it can be said that the two-dimensional image data and the guide image data anatomically correspond with each other. Here, the slice image data group, which is employed for the creation of the guide image data by the image creating unit 16*c*, is previously colored with respect to each organ as described above. The guide image data is therefore colored with respect to each organ similarly to the slice image data.

The mixing unit 16*d* employs the two-dimensional image data supplied from the ultrasonic observation device 5 and the guide image data generated by the image creating unit 16*c*, to create image data (mixed image data) for outputting and displaying a two-dimensional ultrasound image corresponding to the two-dimensional image data and a guide image corresponding to the guide image data on one screen of the display device 12 in an aligned manner under the control of the controlling unit 16. The mixed image data created by the mixing unit 16*d* is supplied to the display circuit 15 under the control of the controlling unit 16. The display circuit 15 converts the mixed image data into image signals corresponding thereto and outputs the resulting image signals under the control of the controlling unit 16. The display device 12 outputs and displays the two-dimensional ultrasound image and the guide image both corresponding to the mixed image data on one screen in an aligned manner based on the image signals sent from the display circuit 15.

The correcting unit 16*e* functions so as to correct the coordinate data of the sample points which change over the elapse of the time t under the control of the controlling unit 16. The correcting unit 16*e* converts the coordinate data of the sample points at the time t to coordinate data of current sample points, i.e., at a subsequent time through a correcting process, and finds the coordinate data of the current sample points which are different from the previous sample points due to the changes in the position of the subject over the elapse of the time t. Along with the correction processing, the image creating unit 16*c* updates the three-axis coordinate system $P_1P_2P_3$ described above using the coordinate data of the current sample points after the correction.

FIG. 2 is a schematic diagram illustrating one example of the marker coil 8 and one example of the plate 9. The marker coil 8 has a stick-like shape, as shown in FIG. 2. Further, one coil is incorporated in the stick-like marker coil 8 at the distal end side thereof as described above. On the other hand, the plate 9 has an oval plate-like shape, for example, so that the plate 9 can easily be attached to the body surface of the subject as described above, and has a body surface contact surface which is an attachment surface to the body surface of the subject as shown in FIG. 2. Further, the orthogonal coordinate system x"y"z" described above is set in the plate 9. The orthogonal coordinate system x"y"z", as shown in FIG. 2, has z"-axis which runs upwards when the body surface contact surface of the plate 9 faces downward, and x"-axis and y"-axis set parallel to the body surface contact surface. Further, the origin O" of the orthogonal coordinate system x"y"z" is set on the plate 9 at a fixed position relative to the plate 9. For example, the origin O" is set at a reference position L on the plate 9. The reference position L is set at a gravitational point of three coil positions on the plate 9, a median point of a straight line connecting a median point of the two coil positions on the plate 9 and the remaining one coil position, or a position where one coil is arranged near the center of the body surface contact surface of the plate 9. Here, in the orthogonal coordinate system x"y"z", a unit vector i" is set along the x"-axis, a unit vector j" is set along the y"-axis, and a unit vector k" is set along the z"-axis, as shown in FIG. 2.

FIG. 3 is a schematic diagram illustrating the receiver coil 10 in which the orthogonal coordinate system xyz is set. As shown in FIG. 3, the origin O is set on the receiver coil 10 at a fixed position relative to the receiver coil 10. For example, the origin O is set at a position near a central axis of an alternating magnetic field receiving surface 10a of the receiver coil 10. In addition, with the origin O as the reference, z-axis is set in a direction of a normal line of the alternating magnetic field receiving surface 10a, and x-axis and y-axis are set parallel to the alternating magnetic field receiving surface 10a. Thus, the orthogonal coordinate system xyz is set on the receiver coil 10. The orthogonal coordinate system xyz is set as a spatial coordinate system of an actual space where the operator examines the subject. In the orthogonal coordinate system xyz, as shown in FIG. 3, a unit vector i is set along x-axis, a unit vector j is set along y-axis, and a unit vector k is set along z-axis.

The receiver coil 10 on which the orthogonal coordinate system xyz is set detects an alternating magnetic field of each of the transmission coil 7, the marker coil 8, and the plate 9 as described above, and transmits the position detection signals to the position data calculating device 6. The position data calculating device 6 calculates a direction component in the orthogonal coordinate system xyz of each of the position vector OC(t) of the central position C(t) of the two-dimensional image plane of the two-dimensional image data, the direction vector V(t) of the two-dimensional image plane of the two-dimensional image data, $V_{12}(t)$, the position vector OL(t) of the reference position L(t) of the plate 9, the rotating matrix T(t) that indicates-the orientation of the plate 9, and the position vector OM(t) of the position M(t) of the marker coil 8.

Here, each of the central position C(t), the position vector OC(t), the direction vector V(t), the direction vector. $V_{12}(t)$, the reference position L(t), the position vector OL(t), the rotating matrix T(t), the position M(t), and the position vector OM(t) is one of the position, the vector, and the rotating matrix that are detected at the time t, and changes over the elapse of the time t along with the changes in the position and the orientation of the distal end of the insertion portion 3.

Here the rotating matrix T(t) is a rotating matrix which indicates the orientation of the plate 9 in the orthogonal coordinate system xyz, and is a 3×3 rotating matrix whose (f,g) component is $t_{fg}(t)$. Since the orthogonal coordinate system x"y"z" is set on the plate 9, as described above, $t_{fg}(t)$ can be defined by the following equation (1):

$$t_{fg}(t) = e''_f \cdot e_g \qquad (1)$$

where integer numbers f and g are one of 1, 2, and 3. A unit vector $e_1$ is the unit vector i described above, a unit vector $e_2$ is the unit vector j described above, and a unit vector $e_3$ is the unit vector k described above. Similarly, a unit vector $e''_1$ is the unit vector i" described above, a unit vector $e''_2$ is the unit vector j" described above, and a unit vector $e''_3$ is the unit vector k" described above. In the equation (1), $e''_f \cdot e_g$ is an inner product of the unit vector $e''_f$ and the unit vector $e_g$. When the rotating matrix T(t) is defined as above, the following equation (2) is satisfied:

$$(ijk) = (i''j''k'') T(t) \qquad (2)$$

Here, the rotating matrix T(t) is based generally on an assumption that the orthogonal coordinate system xyz comes to coincide with the orthogonal coordinate system x"y"z" set on the plate 9 when the orthogonal coordinate system xyz is rotated by so-called Euler angles θ, φ, and Φ, firstly around the z-axis by the angle of Φ degrees, secondly around the y-axis by the angle of φ degrees, and thirdly around the x-axis by the angle of θ degrees, in this order. The rotating matrix T(t) can be represented similarly by the following equation (3). It should be noted that the Euler angles θ, φ, and Φ change according to the change in the posture of the subject, if the subject changes posture over the elapse of the time t.

$$T(t) = \begin{pmatrix} \cos\phi\cos\psi & \cos\phi\sin\psi & -\sin\phi \\ \sin\theta\sin\phi\cos\psi - \cos\theta\sin\psi & \sin\theta\sin\phi\sin\psi + \cos\theta\cos\psi & \sin\theta\cos\phi \\ \cos\theta\sin\phi\cos\psi + \sin\theta\sin\psi & \cos\theta\sin\phi\sin\psi - \sin\theta\cos\psi & \cos\theta\cos\phi \end{pmatrix} \qquad (3)$$

The processing procedure of the controlling unit 16 will be described in detail below. The processing procedure described includes setting of the three-axis coordinate system $P_1'P_2'P_3'$ based on the feature points in the orthogonal coordinate system x'y'z'; setting of the three-axis coordinate system $P_1P_2P_3$ based on the sample points in the orthogonal coordinate system xyz; creation of the guide image data described above based on the two-dimensional image data associated with the above described position data, the three-axis coordinate systems $P_1P_2P_3$ and $P_1'P_2'P_3'$, and the slice image data group; and outputting and displaying of the two-dimensional ultrasound image corresponding to the two-dimensional image data and the guide image corresponding to the guide image data on the same screen of the display device 12 in an aligned manner. In the following, an examination of pancreas of the subject will be described as an example. Four coordinates of four points respectively on the ensiform cartilage, the right end of the pelvis, the pylorus, and the duodenal papilla will be obtained as feature points from the slice image data group, and coordinates of four points on the ensiform cartilage, the right end of the pelvis, the pylorus, and the duodenal papilla of the subject will be obtained as sample points, by way of example. It should be noted however, that the present invention is not limited to the example described here.

FIG. 4 is a flowchart illustrating the processing procedure of the controlling unit 16 up to the outputting and displaying of the two-dimensional ultrasound image corresponding to the two-dimensional image data and the guide image corresponding to the guide image data on the same screen of the display device 12 in an aligned manner. As shown in FIG. 4, when the operator manipulates the input device 11 to perform a command input of the feature point coordinate information for each position of the ensiform cartilage, the right end of the pelvis, the pylorus, and the duodenal papilla on the slice image displayed on the display device 12, the controlling unit 16 detects the feature point coordinate information for each position of the ensiform cartilage, the right end of the pelvis, the pylorus, and the duodenal papilla, and controls the image creating unit 16*c*. The image creating unit 16*c* performs the feature point setting process to set each feature point on the orthogonal coordinate system x'y'z' based on the input feature point coordinate information under the control of the controlling unit 16 (step S101). Subsequently, the controlling unit 16 associates the coordinate data of each feature point set by, the image creating unit 16*c* with the above described slice image data group and stores the coordinate data in the image storing unit 14.

For example, the image creating unit 16*c* sets the feature point. $P_0'$ based on the feature point coordinate information on the orthogonal coordinate system. x'y'z' corresponding to the ensiform cartilage on the slice image under the control of the controlling unit 16, and sets the feature point $P_1'$ based on the feature point coordinate information on the orthogonal coordinate system x'y'z' corresponding to the right end of the pelvis on the slice image. Similarly, the image creating unit 16*c* sets the feature point $P_2'$ based on the feature point coordinate information on the orthogonal coordinate system x'y'z' corresponding to the pylorus on the slice image, and sets the feature point $P_3'$ based on the feature point coordinate information on the orthogonal coordinate system x'y'z' corresponding to the duodenal papilla on the slice image under the control of the controlling unit 16. The controlling unit 16 associates the coordinate data of each of the feature points $P_0'$ to $P_3'$ set by the image creating unit 16*c* with the above described slice image data group and stores the same in the image storing unit 14.

Subsequently, when the operator inputs sample point setting command information for each position of the ensiform cartilage, the right end of the pelvis, the pylorus, and the duodenal papilla, using the probe 2, the marker coil 8 or the plate 9, and the input device 11, the controlling unit 16 detects the sample point setting command information for each position of the ensiform cartilage, the right end of the pelvis, the pylorus, and the duodenal papilla, and recognizes each piece of the position data sent from the position data calculating device 6 received at the timing of the detection as the position data for each sample point, and controls the image creating unit 16. Further, the controlling unit 16 detects the time t at which the controlling unit 16 detects each piece of the sample point setting command information with the timer 16*b*. The image creating unit 16*c* performs a sample point setting process to set each of the sample points on the orthogonal coordinate system xyz based on the input sample point setting command information using each piece of the position data recognized as the position data of each sample point under the control of the controlling unit 16 (step S102).

For example, the image creating unit 16*c* sets the sample point $P_0$ on the orthogonal coordinate system xyz based on the sample point setting command information and the position data corresponding to the ensiform cartilage of the subject under the control of the controlling unit 16. Further, the controlling unit 16 sets the sample point $P_1$ on the orthogonal coordinate system xyz based on the sample point setting command information and the position data corresponding to the right end of the pelvis of the subject. Here, the controlling unit 16 detects the time t at which the controlling unit 16 detects the sample point setting command information as a time t1 at which the sample points $P_0$ and $P_1$ are set. Similarly, the image creating unit 16*c* sets the sample point $P_2$ on the orthogonal coordinate system xyz based on the sample point setting command information and the position data corresponding to the pylorus of the subject, and sets the sample point $P_3$ on the orthogonal coordinate system xyz based on the sample point setting command information and the position data corresponding to the duodenal papilla of the subject under the control of the controlling unit 16. Here, the controlling unit 16 detects the time t at which the controlling unit 16 detects the sample setting command information as times t2 and t3 at which the sample points $P_2$ and $P_3$ are set, respectively. The controlling unit 16 stores each piece of the coordinate data of the sample points $P_0$, $P_1$, $P_2$, and $P_3$ set by the image creating unit 16*c* in the storing unit 16*a*.

If the operator does not perform an input manipulation of scanning starting command information using the input device 11, the controlling unit 16 does not detect the scanning starting command information (No in step S103), and subsequently repeats the processing procedure of step S103. Thus, the controlling unit 16 monitors on a steady basis whether the operator inputs the scanning starting command information from the input device 11 or not.

On the other hand, when the operator performs the input manipulation of the scanning starting command information using the input device 11, the controlling unit 16 detects the scanning starting command information (Yes in step S103), and commands the ultrasonic observation device 5 to start the radial scan based on the scanning starting command information (step S104). The ultrasonic observation device 5 drive controls the ultrasonic transducer 3*a* and the motor 4*a* to start the radial scan under the control of the controlling unit 16.

Then, the controlling unit 16 obtains the two-dimensional image data from the ultrasonic observation device 5 (step S105), and detects a time ts with the timer 16*b* as the time of obtainment of the two-dimensional image data. The image creating unit 16*c* associates the two-dimensional image data with the position data sent from the position data calculating unit 6 at substantially the same timing as the time (time ts) of the data obtainment (step S106). The position data, here, is position data based on the alternating magnetic field from the transmission coil 7, and more specifically, is the coordinate data of the position vector OC(ts) of the central position C(ts), the coordinate data of the direction vector V(ts), and the coordinate data of the direction vector $V_{12}$(ts) described above. In the step S106, the two-dimensional image data is made associated with the position vector OC(t) of the central position C(ts) of the image plane, the direction vector V(ts) of the image plane, and the direction vector $V_{12}$(ts) of the image plane. The controlling unit 16 stores each piece of the coordinate data in the orthogonal coordinate system xyz of the central position C(ts), the position vector OC(ts), the direction vector V(ts), and the direction vector $V_{12}$(ts) in the storing unit 16*a*.

The correcting process by the correcting unit 16*e* will be described. In the process described by way of example below, the operator attaches and fixes the plate 9 to the subject so that the reference position L(t) of the plate 9 is always on the position of the ensiform cartilage of the subject, and the position and the orientation of the plate 9 changes according to the change in the posture of the subject. When the controlling unit 16 detects the elapse of the time t in the above-described steps S102 to S106 based on the time t detected with the timer 16*b*, the correcting unit 16*e*, in response to the above detection as a trigger, performs the correcting process to correct differences between the coordinate components of the sample points $P_0$ to $P_3$ that are set at the times t1 to t3 described above and the coordinate components of the sample point $P_0$ to $P_3$ at the time ts (i.e., the current time) (step S107). The correcting unit 16e performs the correcting process based on the respective coordinate components of the sample points $P_0$ to $P_3$ at time t1 to t3, the rotating matrixes T(t1) to T(t3), and the position data input from the position data calculating device 6 at the time ts, such as the position vector OL(ts) of the reference position L(ts) of the plate 9 and the rotating matrix T(ts) indicating the orientation of the plate 9 under the control of the controlling unit 16. Thus, the correcting unit 16e updates the sample points $P_0$ to $P_3$ that are set at the times t1 to t3 to the sample points $P_0$ to $P_3$ of the time ts (i.e., the current time).

For example, the correcting unit 16e updates the position vector $OP_0(t1)$ of the sample point $P_0$ at the time t1 on the orthogonal coordinate system xyz to the position vector $OP_0(ts)$ of the sample point $P_0$ at the time ts on the orthogonal coordinate system xyz using the coordinate component of the sample point $P_0$ at the time t1 and the direction component of the position vector OL(ts). Since the sample point $P_0$ always coincides with the reference position L(t) of the plate 9, the position vector $OP_0(ts)$, which corresponds to the sample point $P_0$ at the time ts, can be regarded as the same as the position vector OL(ts), and can be represented by the following equation (4):

$$OP_0(ts) = x_{P0}(ts)i + y_{P0}(ts)j + z_{P0}(ts)k \qquad (4)$$
$$= OL(ts)$$

In the equation (4), the direction components $x_{P0}(ts)$, $y_{P0}(ts)$, and $z_{P0}(ts)$ are coordinate components of the position vector $OP_0(ts)$ in the x-axis direction, the y-axis direction, and the z-axis direction, respectively.

Further, the correcting unit 16e updates the position vector $OP_1(t1)$ of the sample point $P_1$ at the time t1 on the orthogonal coordinate system xyz to the position vector $OP_1(ts)$ of the sample point $P_1$ at the time ts on the orthogonal coordinate system xyz using the coordinate component of the sample point $P_1$ at the time t1, the respective coordinate components of the sample point $P_0$ at the time t1 and ts, and the rotating matrixes T(t1), T(ts).

Here, the respective direction components $x_{P1}(ts)$, $y_{P1}(ts)$, and $z_{P1}(ts)$ of the position vector $OP_1(ts)$ in the x-axis direction, the y-axis direction, and the z-axis direction can be represented by the following equation (5), and the position vector $OP_1(ts)$ can be represented by the following equation (6):

$$\begin{pmatrix} x_{P1}(ts) \\ y_{P1}(ts) \\ z_{P1}(ts) \end{pmatrix} = \begin{pmatrix} x_{P0}(ts) \\ y_{P0}(ts) \\ z_{P0}(ts) \end{pmatrix} + {}^tT(ts)T(t1)\begin{pmatrix} x_{P1}(ts) - x_{P0}(t1) \\ y_{P1}(ts) - y_{P0}(t1) \\ z_{P1}(ts) - z_{P0}(t1) \end{pmatrix} \qquad (5)$$

$$OP_1(ts) = x_{P1}(ts)i + y_{P1}(ts)j + z_{P1}(ts)k \qquad (6)$$

Here, the transposed matrix ${}^tT(ts)$ is a transposed matrix of the rotating matrix T(ts), and is calculated based on the rotating matrix T(ts).

Further, the correcting unit 16e updates the position vector $OP_2(t2)$ of the sample point $P_2$ at the time t2 on the orthogonal coordinate system xyz to the position vector $OP_2(ts)$ of the sample point $P_2$ at the time ts on the orthogonal coordinate system xyz using the coordinate component of the sample $P_2$ at the time t2, the respective coordinate components of the sample point $P_0$ at the times t2 and ts, and the rotating matrixes T(t2) and T(ts) at the times t2 and ts. Here, the respective direction components $x_{P2}(ts)$, $y_{P2}(ts)$, and $z_{P2}(ts)$ of the position vector $OP_2(ts)$ in the x-axis direction, the y-axis direction, and the z-axis direction are represented by the following equation (7), and the position vector $OP_2(ts)$ is represented by the following equation (8):

$$\begin{pmatrix} x_{P2}(ts) \\ y_{P2}(ts) \\ z_{P2}(ts) \end{pmatrix} = \begin{pmatrix} x_{P0}(ts) \\ y_{P0}(ts) \\ z_{P0}(ts) \end{pmatrix} + {}^tT(ts)T(t2)\begin{pmatrix} x_{P2}(t2) - x_{P0}(t2) \\ y_{P2}(t2) - y_{P0}(t2) \\ z_{P2}(t2) - z_{P0}(t2) \end{pmatrix} \qquad (7)$$

$$OP_2(ts) = x_{P2}(ts)i + y_{P2}(ts)j + z_{P2}(ts)k \qquad (8)$$

Further, the correcting unit 16e updates the position vector $OP_3(t3)$ of the sample point $P_3$ at the time t3 on the orthogonal coordinate system xyz to the position vector $OP_3(ts)$ of the sample point $P_3$ at the time ts on the orthogonal coordinate system xyz using the coordinate components of the sample point $P_3$ at the time t3, the respective-coordinate components of the sample point $P_0$ at the times t3 and ts, and the rotating matrixes T(t3) and T(ts) at the times t3 and ts. Here, the respective direction components $x_{P3}(ts)$, $y_{P3}(ts)$, and $z_{P3}(ts)$ of the position vector $OP_3(ts)$ in the x-axis direction, the y-axis direction, and the z-axis direction are represented by the following equation (9) and the position vector $OP_3(ts)$ is represented by the following equation (10);

$$\begin{pmatrix} x_{P3}(ts) \\ y_{P3}(ts) \\ z_{P3}(ts) \end{pmatrix} = \begin{pmatrix} x_{P0}(ts) \\ y_{P0}(ts) \\ z_{P0}(ts) \end{pmatrix} + {}^tT(ts)T(t3)\begin{pmatrix} x_{P3}(t3) - x_{P0}(t3) \\ y_{P3}(t3) - y_{P0}(t3) \\ z_{P3}(t3) - z_{P0}(t3) \end{pmatrix} \qquad (9)$$

$$OP_3(ts) = x_{P3}(ts)i + y_{P3}(ts)j + z_{P3}(ts)k \qquad (10)$$

Thus, the correcting unit 16e updates the sample point $P_0$ set at the time t1 (corresponding to the ensiform cartilage of the subject at the time t1) and the sample point $P_1$ set at the time t1 (corresponding to the right end of the pelvis of the subject at the time t1) to the sample point $P_0$ at the time ts (corresponding to the ensiform cartilage of the subject at the time ts) and the sample point $P_1$ at the time ts (corresponding to the right end of the pelvis of the subject at the time ts), respectively. Further, the correcting unit 16e updates the sample point $P_2$ set at the time t2 (corresponding to the pylorus of the subject at the time t2) to the sample point $P_2$ at the time ts (corresponding to the pylorus of the subject at the time ts), and updates the sample point $P_3$ set at the time t3 (corresponding to the duodenal papilla of the subject at the time t3) to the sample point $P_3$ at the time ts (corresponding to the duodenal papilla of the subject at the time ts).

Then, the image creating unit 16c performs the guide image creating process to create guide image data which anatomically corresponds to the two-dimensional image data at the time ts based on the various types of position data of the two-dimensional image data obtained by the controlling unit 16 at the time ts, for example, the position vector OC(ts), the direction vector V(ts), and the direction vector $V_{12}(ts)$, and the respective coordinate components of the sample points $P_0$ to $P_3$ at the time ts as updated in step S107 described above, and the slice image data group read out from the image storing unit 14 (step S108). The guide image data is created as image data that anatomically corresponds to the two-dimensional image data at the time ts, and as the position data thereof, the position vector O'C'(ts) of the central position C'(ts) of the guide image plane, the direction vector V'(ts), and the direction vector $V_{12}$'(ts) are associated with on the above described orthogonal coordinate system x'y'z'. The position vector O'C'(ts), the direction vector V'(ts), and the direction vector $V_{12}$'(ts) anatomically correspond to the position vector OC(ts), the direction vector V(ts), and the direction vector $V_{12}$(ts), respectively.

Subsequently, the mixing unit 16d creates mixed image data using the two-dimensional image data associated with the position data of the time ts in the above described step S106 and the guide image data of the time ts created in the step S108 under the control of the controlling unit 16 in order to output and display the two-dimensional image data at the time ts and the guide image data at the time ts on the same screen of the display device 12 in an aligned manner. The mixed image data created by the mixing unit 16d is output to the display circuit 15 under the control of the controlling unit 16. The display circuit 15 converts the mixed image data into the image signals corresponding to the mixed image data and outputs the resulting image signals under the control of the controlling unit 16 as described above. The display device 12 outputs and displays the two-dimensional ultrasound image of the time ts and the guide image of the time ts both corresponding to the mixed image data on the same screen in an aligned manner based on the image signals sent from the display circuit 15. In other words, the controlling unit 16 makes the display device 12 output and display the two-dimensional ultrasound image of the time ts and the guide image of the time ts on the same screen in an aligned manner by sending the mixed image data to the display circuit 15 (step S109).

If the operator performs an input manipulation of scanning ending command information using the input device 11 in the above described state, the controlling unit 16 detects the scanning ending command information (Yes in step S110), and commands the ultrasonic observation device 5 to end the radial scan based on the scanning ending command information. The ultrasonic observation device 5 drive controls the ultrasonic transducer 3a and the motor 4a to end the radial scan under the control of the controlling unit 16. On the other hand, if the operator does not perform the input manipulation of the scanning ending command information, the controlling unit 16 does not detects the scanning ending command information (No in step S110), and repeats the processing procedure from the step S103 described above.

Figure 5:
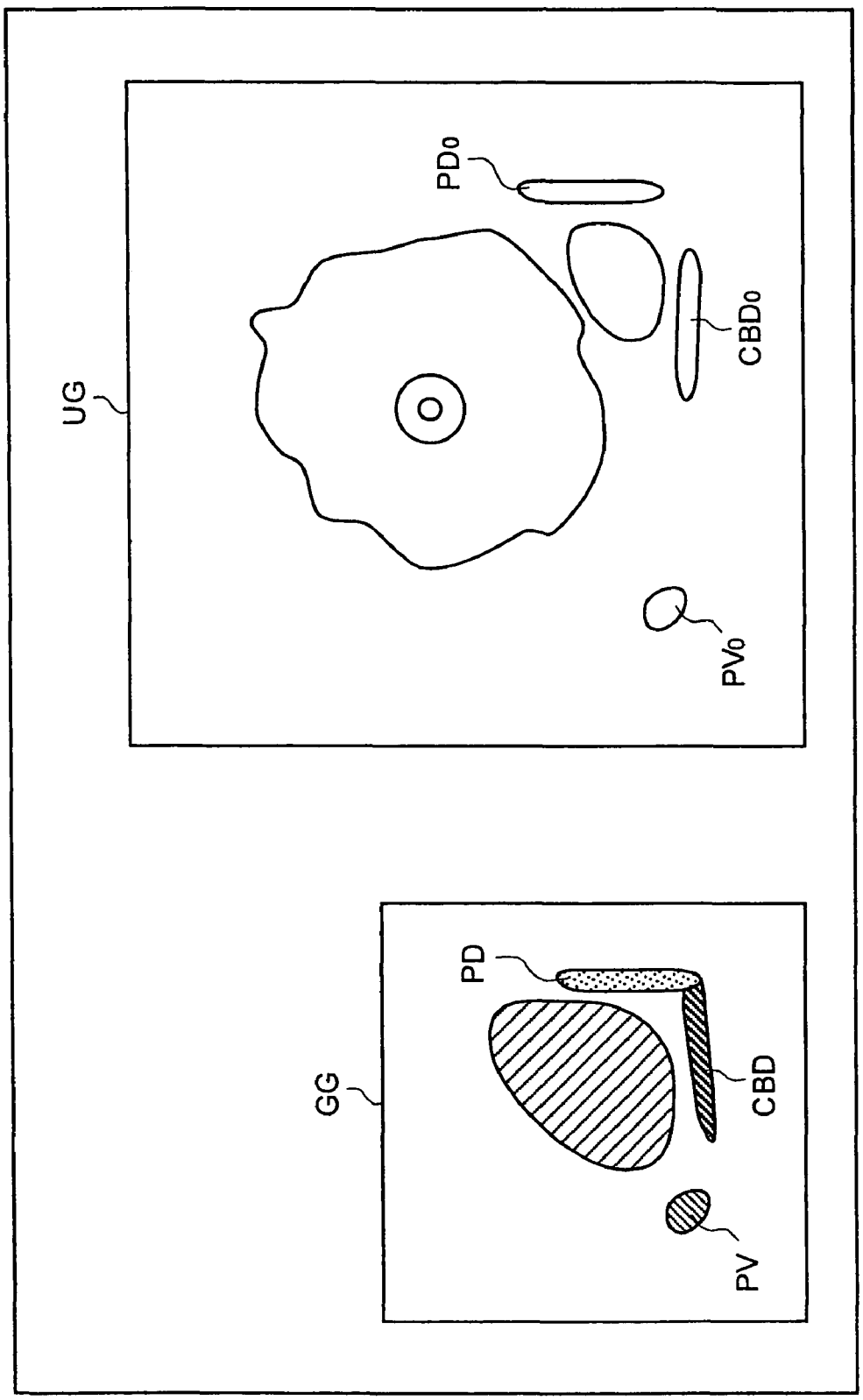
FIG. 5 is a schematic diagram of an exemplary display of the two-dimensional ultrasound image and the guide image in an aligned manner on one screen.

FIG. 5 is a schematic diagram illustrating an example of the two dimensional ultrasound image and the guide image output and displayed in an aligned manner on the same screen of the display device 12. A two-dimensional ultrasound image UG corresponds to the two-dimensional image data of the time ts described above, and a guide image GG corresponds to the guide image data of the time ts described above. In FIG. 5, the two-dimensional ultrasound image UG represents a region near a merging section of a pancreas duct and a bile duct of the subject, and shows a pancreas duct $PD_0$, a common bile duct $CBD_0$, and a portal vein $PV_0$. A center of the image of the two-dimensional ultrasound image UG corresponds to the rotational center of the ultrasonic transducer 3a, i.e., the central position C(ts), and a direction of a normal line of the two-dimensional ultrasound image UG corresponds to the direction vector V(ts). A direction of twelve o'clock of the two-dimensional ultrasound image UG, i.e., the upward direction in FIG. 5 corresponds to the direction vector $V_{12}$(ts), and a direction of three o'clock of the two-dimensional ultrasound image UG, i.e., the rightward direction in FIG. 5, corresponds to an outer product $V_{12}(ts) \times V(ts)$ of the direction vector $V_{12}(ts)$ and the direction vector V(ts). On the other hand, a center of an image of the guide image GG corresponds to the central position C'(ts), and a direction of a normal line corresponds to the direction vector V'(ts). Further, a direction of twelve o'clock of the guide image GG, i.e., an upward direction in FIG. 5 corresponds to the direction vector $V_{12}$'(ts), and a direction of three o'clock of the guide image GG, i.e., the rightward direction in FIG. 5 corresponds to an outer product $V_{12}$'(ts)$\times$V'(ts) of the direction vector $V_{12}$'(ts) and the direction vector V'(ts)

Here, the controlling unit 16 makes an image direction represented by the direction vector V(ts) anatomically coincide with an image direction represented by the direction vector V'(ts), an image direction represented by the direction vector $V_{12}$(ts) anatomically coincide with an image direction represented by the direction vector $V_{12}$'(ts), and an image direction represented by an outer product $V_{12}(ts) \times V(ts)$ anatomically coincide with an image direction represented by an outer product $V_{12}$'(ts)$\times$V'(ts), thereby allowing an output and display of the two-dimensional ultrasound image UG and the guide image GG on the same screen in an aligned manner so that the position and the orientation of the organ or the like presented in each image correctly corresponds with each other in an anatomical sense.

Further, since the organs in the guide image data are presented in different colors as described above, when the guide image GG is output and displayed on the display device 12, each organ is presented in different color. For example, the guide image GG shows the merging section of the pancreas duct and the bile duct as shown in FIG. 5, and different colors are assigned to characteristic organs, such as the pancreas duct PD, the common bile duct CBD, and the portal vein PV, respectively. Further, the controlling unit 16 can make the display device 12 output and display the guide image GG together with abbreviations for organs (for example, abbreviations like PD, CBD, and PV shown in FIG. 5) as annotations for each organ by controlling the mixing unit 16d so that the abbreviations such as PD, CBD, and PV for the respective organs are superposed onto the guide image GG. Annotation information which is related to the abbreviations of the organs is previously stored in the image storing unit 14 in association with the slice image data group.

Further, the controlling unit 16 can sequentially obtain the two-dimensional image data and the position data thereof, and the guide image data which anatomically corresponds to the two-dimensional image data and the position data thereof by repeating the processing procedure of the above described steps S103 to S110. Then, the controlling unit 16 sequentially updates the obtained two-dimensional image data and the guide image data, and the two-dimensional ultrasound image and the guide image corresponding respectively thereto, and at the same time, outputs and displays the two-dimensional ultrasound image and the guide image on the same screen of the display device 12 in an aligned manner. For example, when the operator repeatedly performs the radial scan with the ultrasonic diagnosis apparatus 1 to find an interest region inside the subject, the controlling unit 16 repeats the above described processing procedure of the steps S103 to S110, and thereby outputs and displays the guide image and the two-dimensional ultrasound image in real time on the display device 12 while sequentially updating the guide image and the two-dimensional ultrasound image.

Therefore, the operator can recognize correctly and easily which anatomical region of the subject is represented by the currently displayed two-dimensional ultrasound image, simply by looking at the two-dimensional ultrasound image and the guide image displayed on the display device 12 and referring to the colored images of the organs or the like in the guide image. Thus, the operator can make medical diagnosis of the subject correctly and efficiently. For example, when the pancreas is shown in yellow color on the guide image, the operator can easily know that the yellowish region on the guide image represents the pancreas while observing the two-dimensional ultrasound image, or the operator can move the distal end of the insertion portion 3 thereby moving the scanning plane of the ultrasonic transducer 3a to locate the pancreas.

Figure 6:
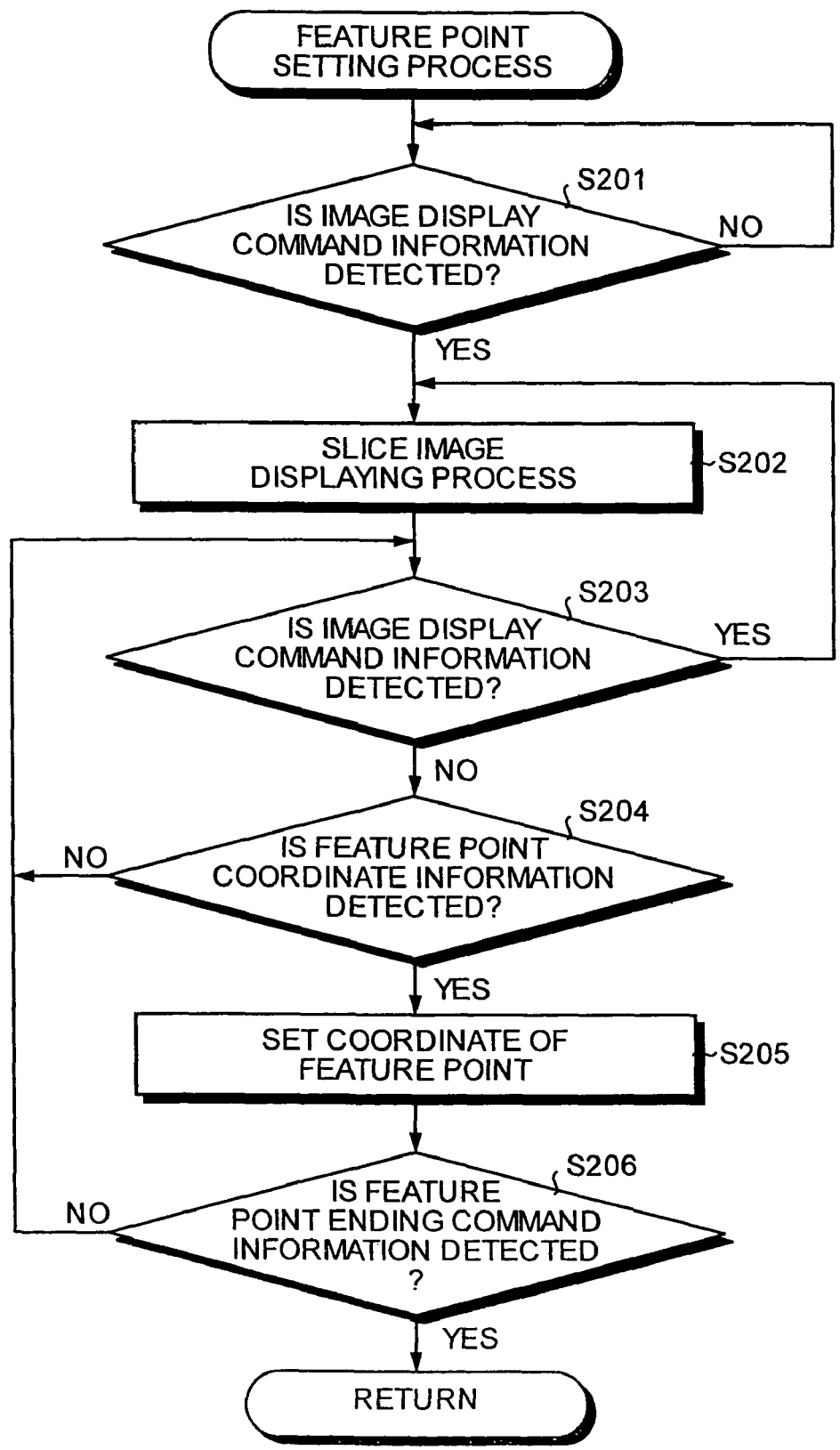
FIG. 6 is a flowchart illustrating a processing procedure up to a completion of a feature point setting process.
Figure 7:
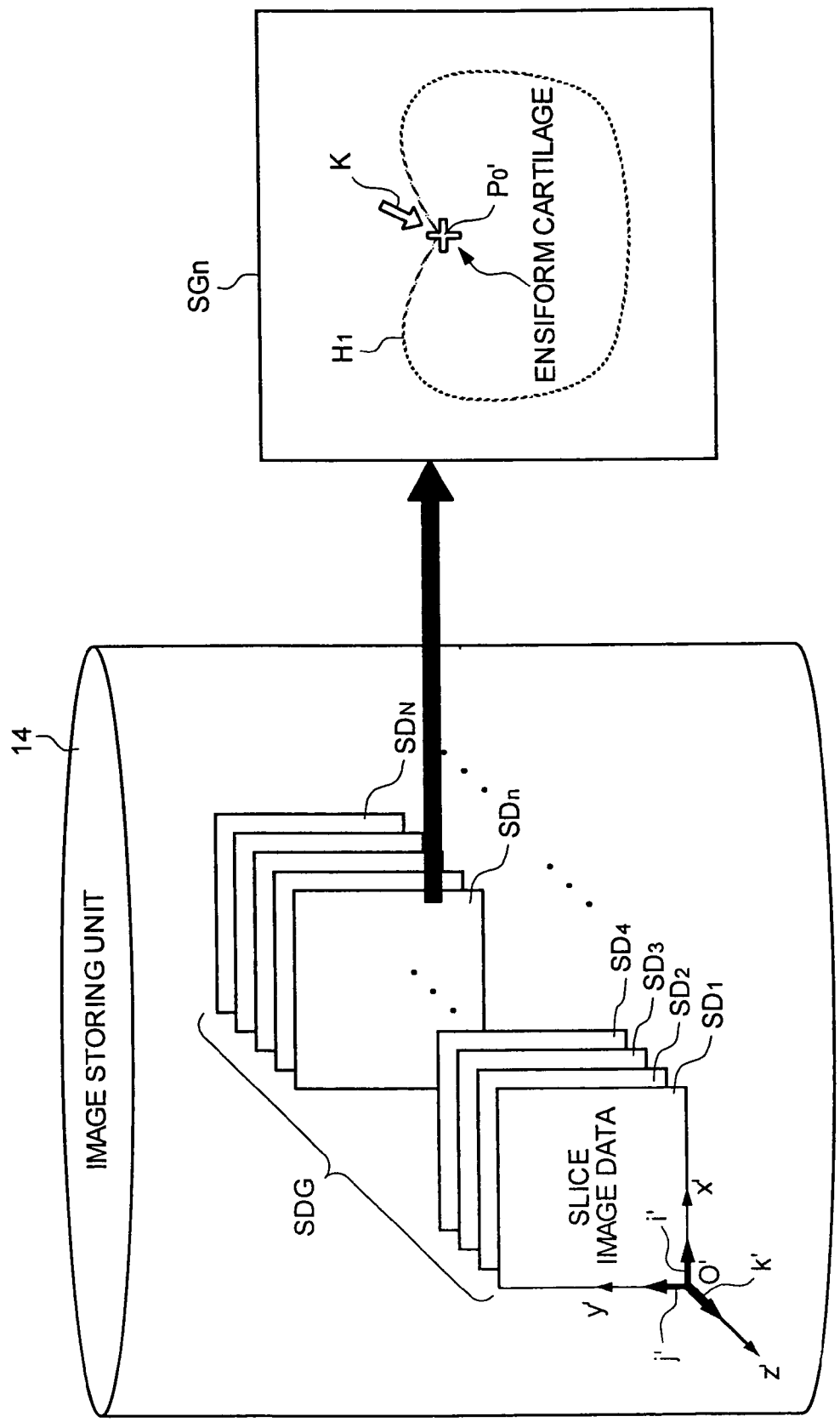
FIG. 7 is a schematic diagram illustrating an operation of setting a feature point on slice image data.

The feature point setting process of step S101 described above will be described in more detail. FIG. 6 is a flowchart illustrating the processing procedure up to the completion of the feature point setting process by the controlling unit 16. FIG. 7 is a schematic diagram illustrating the operation of setting a feature point on the slice image data previously stored in the image storing unit 14. As shown in FIGS. 6 and 7, before the observation of the interior of the subject body, the operator selects slice image data in which an anatomically characteristic point is shown from the slice image data group SDG stored in the image storing unit 14. Specifically, when the operator performs an input manipulation of image display command information using the input device 11 to command the output and the display of a slice image, the controlling unit 16 detects the input image display command information (Yes in step S201). Then, the controlling unit 16 performs a slice image displaying process by reading out one piece of slice image data from the slice image data group SDG in the image storing unit 14 based on the detected image display command information and by making the display device 12 output and display a slice image which corresponds to the read out slice image data (step S202). On the other hand, if the operator does not perform the input manipulation of the image display command information, the controlling unit 16 does not detect the image display command information (No in step S201), and repeats the processing procedure of step S201. Thus, the controlling unit 16 monitors the input of the image display command information from the input device 11 on a steady basis.

The slice image data group SDG is an image data group in which N (N is an integer number) pieces of the slice image data $SD_1$ to $SD_N$ are arranged in the orthogonal coordinate system x'y'z' described above as shown in FIG. 7. Here, the orthogonal coordinate system x'y'z' is set as shown in FIG. 7 so that the origin O' is located at a corner of the first slice image data $SD_1$ and each image plane of the slice image data $SD_1$ to $SD_N$ is a plane consisting of the x'-axis and the y'-axis. Further, in the orthogonal coordinate system x'y'z', a unit vector i' is set along the x'-axis, a unit vector j' is set along the y'-axis, and a unit vector k' is set along the z'-axis as shown in FIG. 7.

In the slice image displaying process of step S202 described above, the controlling unit 16 reads out the slice image data $SD_1$ from the image storing unit 14 based on the image display command information detected in step S201, and transmits the read out slice image data $SD_1$ to the display circuit 15. The display circuit 15 converts the slice image data $SD_1$ into image signals and outputs the generated image signals as described above. The display device 12 receives the image signals from the display circuit 15 and outputs and displays a slice image corresponding to the slice image data $SD_1$.

If the operator performs an input manipulation of the image display command information using the input device 11 in the above described state, the controlling unit 16 detects the input image display command information (Yes in step S203), and repeats the processing procedure from step S202 described above. Here, the controlling unit 16 sequentially reads out the slice image data $SD_2$ to $SD_N$ from the image storing unit 14 corresponding to each piece of the detected image display command information based on the image display command information detected in step S203, and sequentially transmits the read out slice image data $SD_2$ to $SD_N$ to the display circuit 15. Thus, the controlling unit 16 makes the display device 12 sequentially update, output, and display the slice images each corresponding to the slice image data $SD_2$ to $SD_N$. Since the controlling unit 16 repeats the processing procedure of steps S201 to S203 described above, the operator can sequentially confirm slice images each corresponding to the slice image data $SD_1$ to $SD_N$ on the display device 12. For example, the operator can find an anatomically characteristic region such as the ensiform cartilage, the right end of the pelvis, the pylorus, and the duodenal papilla, on the slice image $SG_n$ which corresponds to the slice image data $SD_n$, which is an n-th (n is an integer number ranging from 1 to N) piece of data in the slice image data group SDG.

When the operator finds an anatomically characteristic region on the slice image $SG_n$, the operator performs an input manipulation of the feature point coordinate information of a feature point using the input device 11 in order to allocate the feature point at the found region. The controlling unit 16 does not detect the image display command information (No in step S203), and instead detects the input feature point coordinate information (Yes in step S204). Then, the image creating unit 16c sets coordinate data based on the detected feature point coordinate information as the slice image data $SD_n$, i.e., coordinate data of the feature point on the orthogonal coordinate system x'y'z' (step S205).

For example, if the slice image $SG_n$ shows an ensiform cartilage of a costa $H_1$, as shown in FIG. 7, the operator manipulates the input device 11 to move a cursor K on the display device 12 to a position of the ensiform cartilage, and performs a click manipulation or the like to input the feature point coordinate information. The controlling unit 16 detects the input feature point coordinate information, and the image creating unit 16c sets coordinate data based on the detected feature point coordinate information as the coordinate data of the feature point $P_0'$ under the control of the controlling unit 16. Thus, the feature point $P_0'$ is set as the coordinate point which is on the orthogonal coordinate system x'y'z' and which corresponds to the ensiform cartilage of the costa $H_1$ on the slice image $SG_n$, as shown in FIG. 7.

Subsequently, if the operator does not perform an input manipulation of feature point ending command information to command to end the feature point setting process, the controlling unit 16 does not detect the feature point ending command information (No in step S206) and repeats the processing procedure from the step S203 described above. Thus, the operator can designate and input feature point coordinate information for every characteristic region in substantially the same manner as the manner of information input for the feature point $P_0'$ which corresponds to the ensiform cartilage. The image creating unit 16c sequentially sets feature points on the orthogonal coordinate system x'y'z' based on each piece of the feature point coordinate information input for the characteristic regions under the control of the controlling unit 16. For example, the image creating unit 16c sequentially sets the feature points $P_1'$ to $P_3'$ as coordinate points each corresponding to one of the right end of the pelvis, the pylorus, and the duodenal papilla on the orthogonal coordinate system x'y'z' based on the feature point coordinate information on the right end of pelvis, the pylorus, or the duodenal papilla that are the characteristic regions.

On the other hand, if the operator performs the input manipulation of the feature point ending command information using the input device 11, the controlling unit 16 detects the input feature point ending command information (Yes in step S206), and performs the processing procedure from the step S102 described above. Further, if the controlling unit 16 does not detect the feature point coordinate information in step S204 (No in step S204), the controlling unit 16 repeats the processing procedure from step S203.

Here, the image creating unit 16c sets the feature points $P_0'$ to $P_3'$ on the orthogonal coordinate system x'y'z' as described above. Therefore, the position vector $O'P_0'$ of the feature point $P_0'$, the position vector $O'P_1'$ of the feature point $P_1'$, the position vector $O'P_2'$ of the feature point $P_2'$, and the position vector $O'P_3'$ of the feature point $P_3'$ are represented by the following equations (11) to (14), respectively, with respect to the orthogonal coordinate system x'y'z':

$$O'P_0' = x_{P0}'i' + y_{P0}'j' + z_{P0}'k' \quad (11)$$

$$O'P_1' = x_{P1}'i' + y_{P1}'j' + z_{P1}'k' \quad (12)$$

$$O'P_2' = x_{P2}'i' + y_{P2}'j' + z_{P2}'k' \quad (13)$$

$$O'P_3' = x_{P3}'i' + y_{P3}'j' + z_{P3}'k' \quad (14)$$

Here, the direction components $x_{P0}'$, $y_{P0}'$, and $z_{P0}'$ are coordinate components of the position vector $O'P_0'$ in the x'-axis direction, the y'-axis direction, and the z'-axis direction, respectively. The direction components $x_{P1}'$, $y_{P1}'$, and $z_{P1}'$ are coordinate components of the position vector $O'P_1'$ in the x'-axis direction, the y'-axis direction, and the z'-axis direction, respectively. The direction components $x_{P2}'$, $y_{P2}'$, and $z_{P2}'$ are coordinate components of the position vector $O'P_2'$ in the x'-axis direction, the y'-axis direction, and the z'-axis direction, respectively. The direction components $x_{P3}'$, $y_{P3}'$, $z_{P3}'$ are coordinate components of the position vector $O'P_3'$ in the x'-axis direction, the y'-axis direction, and the z'-axis direction, respectively.

The image plane of each piece of the slice image data $SD_1$ to $SD_N$ is a 40-cm-square as described above, and the image planes are arranged at 1-mm pitch in parallel. Therefore, the image creating unit 16c can calculate the direction component of each of the position vectors $O'P_0'$, $O'P_1'$, $O'P_2'$, and $O'P_3'$, based on the above arrangement. The controlling unit 16 obtains the direction component of each of the position vectors $O'P_0'$, $O'P_1'$, $O'P_2'$, and $O'P_3'$ as calculated and output by the image creating unit 16c.

Figure 8:
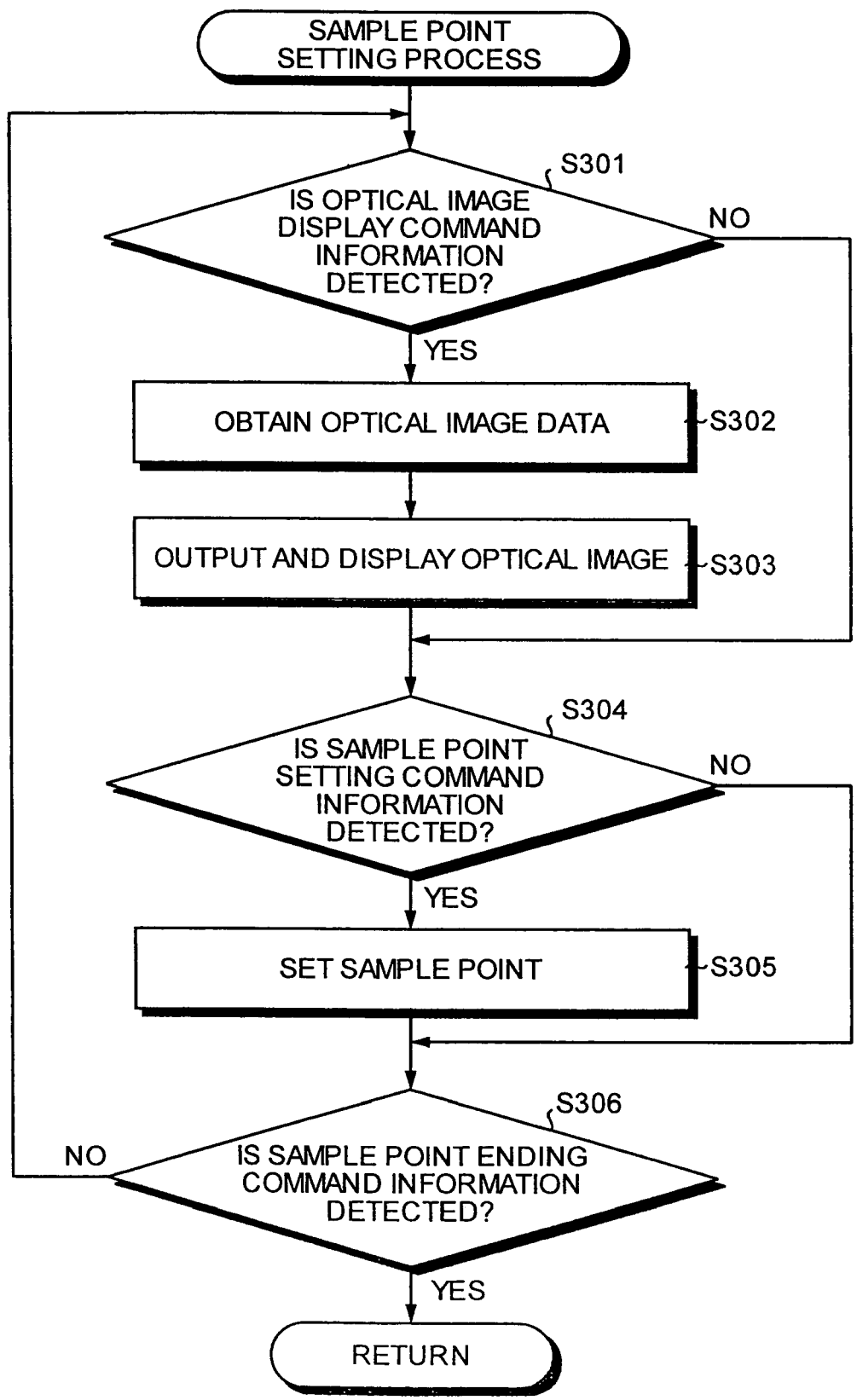
FIG. 8 is a flowchart illustrating a processing procedure up to a completion of a sample point setting process.

The sample point setting process of step S102 described above will be described in more detail. FIG. 8 is a flowchart illustrating the processing procedure up to the completion of the sample point setting process by the controlling unit 16. As described above, the operator inputs the sample point setting command information while keeping the marker coil 8 and the plate 9 in contact with the body surface of the subject or while manipulating the probe 2 and confirming the optical image on the display device 12. A content of the sample setting command information includes not only command information such as "set the sample point", but also command information concerning an obtainment of the position data, such as "simultaneously obtain position data of the marker coil 8 and the plate 9 from the position data calculating device 6", and "simultaneously obtain position data of the transmission coil 7 and the plate 9 from the position data calculating device 6" for the setting of the sample point.

In FIG. 8, if the operator performs an input manipulation of the sample point setting command information using the input device 11 without performing an input manipulation of command information (optical image display command information) to command an output and display of the above described optical image to the display device 12, while keeping the marker coil 8 and the plate 9 in contact with the body surface at a position near the right end of the pelvis and at a position near the ensiform cartilage of the subject, respectively, the controlling unit 16 detects the sample point setting command information (Yes in step S304) without detecting the optical image display command information (No in step S301), and detects the current time with the timer 16b. At the same time, the image creating unit 16c sets the sample point on the orthogonal coordinate system xyz based on the sample point setting command information using the position data supplied from the position data calculating device 6 under the control of the controlling unit 16 (step S305). The controlling unit 16 stores the position data of the sample point set by the image creating unit 16c, i.e., each piece of the coordinate data on the orthogonal coordinate system xyz in the storing unit 16a.

For example, if the content of the sample point setting command information is command information "set the sample point" and "simultaneously obtain the position data of the marker coil 8 and the plate 9 from the position data calculating device 6", the controlling unit 16 detects the time t1 with the timer 16b, and receives position data based on the alternating magnetic field from the plate 9 (plate position data) and position data based on the alternating magnetic filed from the marker coil 8 (marker coil position data) from the position data calculating device 6. Here, the plate position data is coordinate data of the position vector OL(t1) of the reference position L(t1) and the rotating matrix T(t1) described above. The marker coil position data is coordinate data of the position vector OM(t1) at the position M(t1) described above.

The image creating unit 16c sets the coordinate data based on the plate position data of the time t1 as coordinate data of the sample point $P_0$ on the orthogonal coordinate system xyz, and sets the coordinate data based on the marker coil position data of the time t1 as coordinate data of the sample point $P_1$ on the orthogonal coordinate system xyz under the control of the controlling unit 16. Thus, the image creating unit 16c sets the sample point $P_0$ corresponding to the ensiform cartilage of the subject and the sample point $P_1$ corresponding to the right end of the pelvis of the subject on the orthogonal coordinate system xyz.

Here, since the coordinate data of the sample point $P_0$ at the time t1 is based on the coordinate data of the position vector OL(t1), the position vector $OP_0(t1)$ of the sample point $P_0$ at the time t1 in the orthogonal coordinate system xyz can be regarded to be the same as the position vector OL(t1), and can be represented by the following equation (15):

$$OP_0(t1) = x_{P0}(t1)i + y_{P0}(t1)j + z_{P0}(t1)k \quad (15)$$
$$= OL(t1)$$

In the equation (15), the direction components $x_{P0}(t1)$, $y_{P0}(t1)$, and $z_{P0}(t1)$ are coordinate components of the position vector $O_{P0}(t1)$ in the x-axis direction, the y-axis direction, and the z-axis direction, respectively. Further, the position vector $O_{P0}(t1)$ and the above described rotating matrix T(t1) are employed in the correcting process of step S107.

Since the coordinate data of the sample point $P_1$ at the time t1 is based on the coordinate data of the position vector OM(t1), the position vector $OP_1$(t1) of the sample point $P_1$ at the time t1 in the orthogonal coordinate system xyz can be regarded to be the same as the position vector OM(t1), and can be represented by the following equation (16):

$$OP_1(t1) = x_{P1}(t1)i + y_{P1}(t1)j + z_{P1}(t1)k \qquad (16)$$
$$= OM(t1)$$

In the equation (16), the direction components $x_{P1}$(t1), $y_{P1}$(t1), and $z_{P1}$(t1) are coordinate components of the position vector $OP_1$(t1) in the x-axis direction, the y-axis direction, and the z-axis direction, respectively.

Thereafter, if the operator does not perform an input manipulation of the sample point ending command information to command an ending of the sample point setting process, the controlling unit 16 does not detect the sample point ending command information (No in step S306), and repeats the processing procedure from step S301 described above. If the operator performs an input manipulation of the optical image display command information in this state, the controlling unit 16 detects the input optical image display command information (Yes in step S301), and obtains optical image data from the optical observation device 17 based on the detected optical image display command information (step S302).

Then, the controlling unit 16 outputs the obtained optical image data to the display circuit 15. The display circuit 15, as described above, converts the optical image data into image signals corresponding to the optical image data supplied from the controlling unit 16 and outputs the resulting image signals under the control of the controlling unit 16. The display device 12 outputs and displays an optical image corresponding to the optical image data based on the image signals supplied from the display circuit 15. In other words, the controlling unit 16 makes the display device 12 output and display the optical image by sending the optical image data to the display circuit 15 (step S303).

Thereafter, if the operator performs an input manipulation of the sample point setting command information using the input device 11 while confirming the optical image on the display device 12 and keeping the distal end of the insertion portion 3, i.e., a portion close to the ultrasonic transducer 3a, the transmission coil 7, and the optical observation window 3c in contact with the anatomically characteristic region inside the subject body, the controlling unit 16 detects the sample point setting command information (Yes in step S304), and detects the current time with the timer 16b. Then, the image creating unit 16c sets the sample point on the orthogonal coordinate system xyz based on the sample point setting command information using the position data supplied from the position data calculating device 6 under the control of the controlling unit 16 (step S305). The controlling unit 16 stores the position data of the set sample point, i.e., respective pieces of the coordinate data on the orthogonal coordinate system xyz in the storing unit 16a. The controlling unit 16 repeats the processing procedure of steps S301 to S306 until the controlling unit 16 detects the sample point ending command information supplied from the input device 11.

For example, if the content of the sample point setting command information is command information instructing to "set the sample point" and to "simultaneously obtain the position data of the transmission coil 7 and the plate 9 from the position data calculating device 6", the controlling unit 16 detects the time t2 with the timer 16b and receives the position data (transmission coil position data) based on the alternating magnetic field from the transmission coil 7 and the plate position data from the position data calculating device 6. If the distal end of the insertion portion 3 is in contact with a region near the pylorus inside the subject body at the time t2, the controlling unit 16 receives the transmission coil position data as the coordinate data corresponding to the pylorus. Here, the transmission coil position data at the time t2 is the coordinate data of the position vector OC(t2) of the central position C(t2) described above, the coordinate data of the direction vector V(t2), and the coordinate data of the direction vector $V_{12}$(t2). Further, the plate position data at the time t2 is the coordinate data of the position vector OL(t2) at the reference position L(t2) described above and the rotating matrix T(t2).

The image creating unit 16c sets the coordinate data based on the transmission coil position data at the time t2 as the coordinate data of the sample point $P_2$ on the orthogonal coordinate system xyz under the control of the controlling unit 16. Thus, the image creating unit 16c comes to set the sample point $P_2$ corresponding to the pylorus of the subject on the orthogonal coordinate system xyz. At the same time, the image creating unit 16c obtains the position vector $OP_0$(t2) of the sample point $P_0$ at the time t2 based on the plate position data at the time t2. The position vector $OP_0$(t2) can be represented by the following equation (17):

$$OP_0(t2) = x_{P0}(t2)i + y_{P0}(t2)j + z_{P0}(t2)k \qquad (17)$$
$$= OL(t2)$$

In the equation (17), the direction components $x_{P0}$(t2), $y_{P0}$(t2), $z_{P0}$(t2) are coordinate components of the position vector $OP_0$(t2) in the x-axis direction, the y-axis direction, and the z-axis direction, respectively. The position vector $OP_0$(t2) and the above described rotating matrix T(t2) are employed in the correcting process of step S107 described above.

Since the coordinate data of the sample point $P_2$ at the time t2 is based on the coordinate data of the position vector OC(t2), the position vector $OP_2$(t2) of the sample point $P_2$ at the time t2 in the orthogonal coordinate system xyz can be regarded to be the same as the position vector OC(t2), and can be represented by the following equation (18):

$$OP_2(t2) = x_{P2}(t2)i + y_{P2}(t2)j + z_{P2}(t2)k \qquad (18)$$
$$= OC(t2)$$

In the equation (18), the direction components $x_{P2}$(t2), $y_{P2}$(t2), and $z_{P2}$(t2) are coordinate components of the position vector $OP_2$(t2) in the x-axis direction, the y-axis direction, and the z-axis direction, respectively.

Further, the controlling unit 16 detects the time t3 with the timer 16b, and receives the transmission coil position data and the plate position data at the time t3 from the position data calculating device 6. If the distal end of the insertion portion 3 is in contact with a region near the duodenal papilla inside the subject body at the time t3, the controlling unit 16 receives the transmission coil position data at the time t3 as the coordinate data corresponding to the duodenal papilla. The transmission coil position data at the time t3 is the coordinate data of the position vector OC(t3) of the central position C(t3) described above, the coordinate data of the direction vector V(t3), and the coordinate data of the direction vector $V_{12}$(t3). The plate position data at the time t3 is the coordinate data of the position vector OL(t3) of the reference position L(t3) and the rotating matrix T(t3) described above.

The image creating unit 16c sets the coordinate data based on the transmission coil position data at the time t3 as the coordinate data of the sample point $P_3$ on the orthogonal coordinate system xyz under the control of the controlling unit 16. Thus, the image creating unit 16c comes to set the sample point $P_3$ corresponding to the duodenal papilla of the subject on the orthogonal coordinate system xyz. At the same time, the image creating unit 16c obtains the position vector $OP_0$(t3) of the sample point $P_0$ at the time t3 based on the plate position data at the time t3. The position vector $OP_0$(t3) can be represented by the following equation (19):

$$OP_0(t3) = x_{P0}(t3)i + y_{P0}(t3)j + z_{P0}(t3)k \quad (19)$$
$$= OL(t3)$$

In the equation (19), the direction components $x_{P0}$(t3), $y_{P0}$(t3), $z_{P0}$(t3) are coordinate components of the position vector $OP_0$(t3) in the x-axis direction, the y-axis direction, and the z-axis direction, respectively. The position vector $OP_0$(t3) and the above described rotating matrix T(t3) are employed in the correcting process of step S107 described above.

Since the coordinate data of the sample point $P_3$ at the time t3 is based on the coordinate data of the position vector OC(t3), the position vector $OP_3$(t3) of the sample point $P_3$ at the time t3 in the orthogonal coordinate system xyz can be regarded to be the same as the position vector OC(t3), and can be represented by the following equation (20):

$$OP_3(t3) = x_{P3}(t3)i + y_{P3}(t3)j + z_{P3}(t3)k \quad (20)$$
$$= OC(t3)$$

In the equation (20), the direction components $X_{P3}$(t3), $y_{P3}$(t3), and $Z_{P3}$(t3) are coordinate components of the position vector $OP_3$(t3) in the x-axis direction, the y-axis, direction, and the z-axis direction, respectively.

On the other hand, if the operator performs an input manipulation of the sample point ending command information using the input device 11 after the processing procedure of step S305 described above, the controlling unit 16 detects the input sample point ending command information (Yes in step S306), and performs the processing procedure following the step S103 described above. Further, if the controlling unit 16 does not detect the sample point setting command information in step S304 (No in step S304), the controlling unit 16 repeats the processing procedure from step S306 described above.

Figure 9:
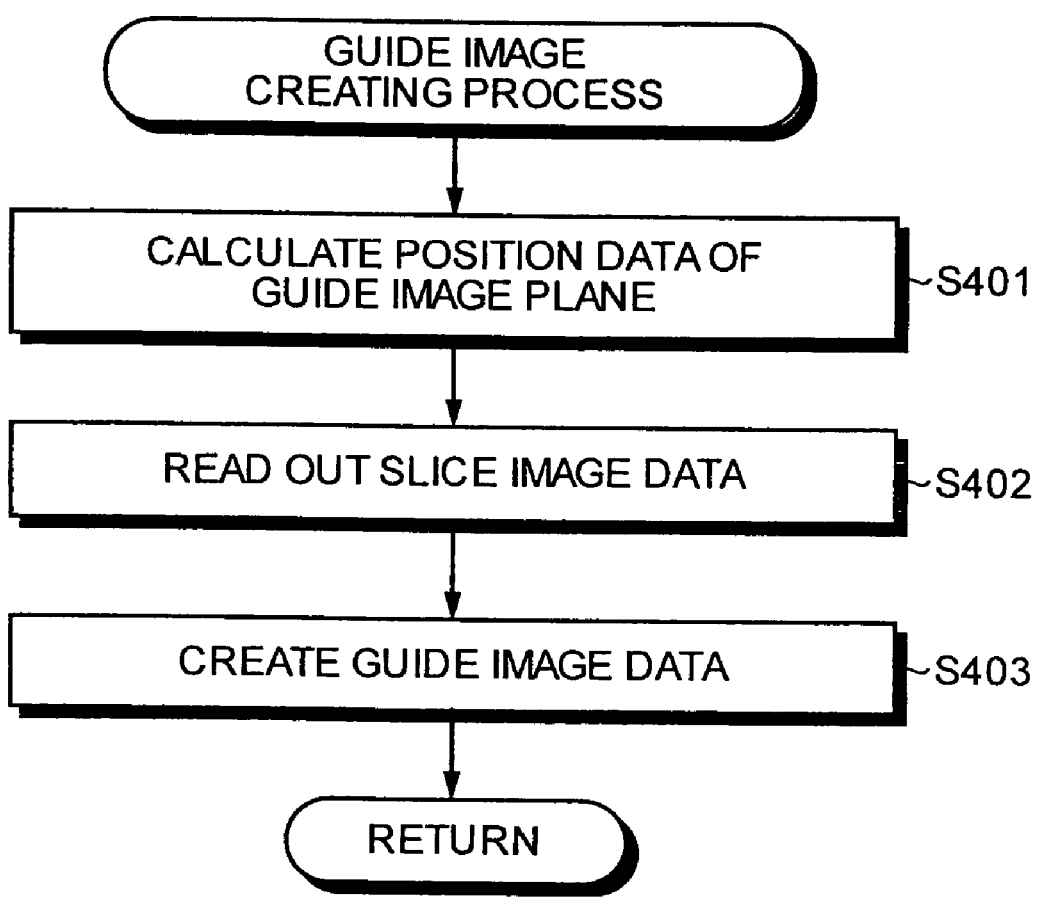
FIG. 9 is a flowchart illustrating a processing procedure up to a completion of a guide image creating process.
Figure 10:
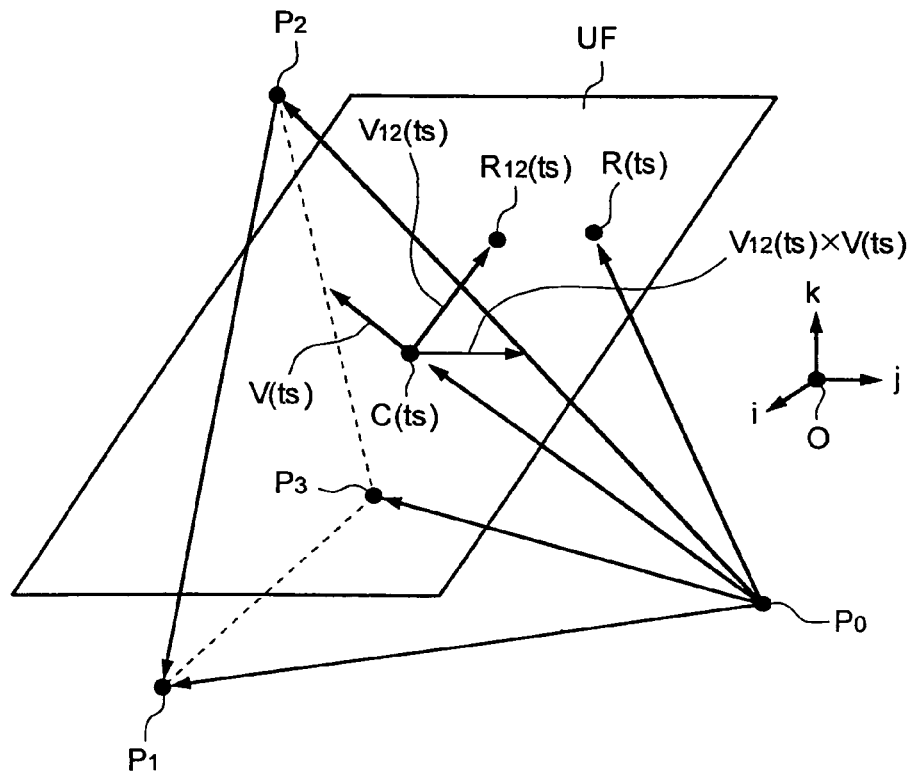
FIG. 10 is a schematic diagram illustrating a relation between a two-dimensional image plane and a three-axis coordinate system based on sample points.
Figure 11:
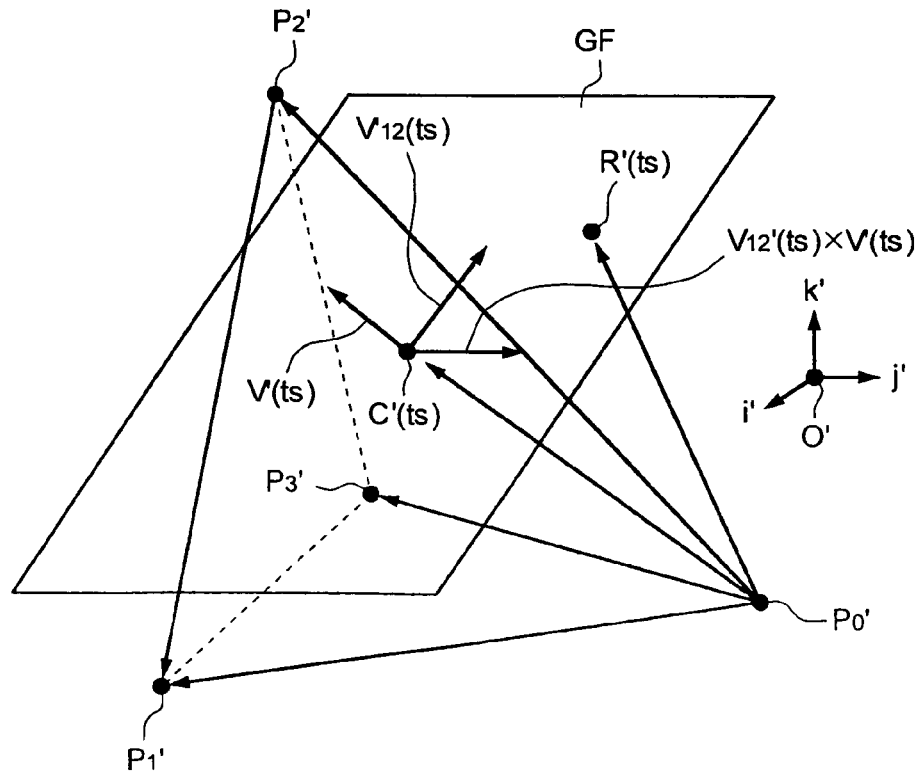
FIG. 11 is a schematic diagram illustrating an operation of calculating a guide image plane and position data thereof.

The guide image creating process of step S108 described above will be described in more detail. FIG. 9 is a flowchart illustrating the processing procedure up to the completion of the guide image creating process described above by the controlling unit 16. FIG. 10 is a schematic diagram illustrating a relation between the two-dimensional image plane of the two-dimensional image data at the time ts and the three-axis coordinate system $P_1P_2P_3$ formed with the sample points $P_0$ to $P_3$ processed by the image creating unit 16c. FIG. 11 is a schematic diagram illustrating an operation of the image creating unit 16c, calculating the guide image plane at the time ts and the position data of the guide image plane.

In FIGS. 9 to 11, after the controlling unit 16 performs step S107 described above, the image creating unit 16c calculates a guide image plane GF of the guide image data at the time ts based on the four feature points $P_0$' to $P_3$' set in the step S101 described above, the four sample points $P_0$ to $P_3$ obtained after the correction and updating in step S107, and the position data associated with the two-dimensional image data of the time ts in step S106 described above (step S401).

Conceptually, the guide image plane GF is calculated in the step S401 as follows. The image creating unit 16c sets the three-axis coordinate system $P_1'P_2'P_3'$ on the orthogonal coordinate system x'y'z' using the feature points $P_0$' to $P_3$' under the control of the controlling unit 16, and at the same time, sets the three-axis coordinate system $P_1P_2P_3$ on the orthogonal coordinate system xyz using the sample points $P_0$ to $P_3$. Here, it is sufficient if the image creating unit 16c sets the three-axis coordinate system using one of the feature points $P_0$' to $P_3$' as the origin. However, it is desirable that the image creating unit 16c use a feature point $P_0$' which anatomically corresponds to the sample point $P_0$ based on the above described plate position data as the origin of the three-axis coordinate system $P_1'P_2'P_3'$ as shown in FIG. 11. In the following, the desirable setting is described. Further, the image creating unit 16c sets the three-axis coordinate system $P_1P_2P_3$ whose axis directions anatomically correspond with those of the three-axis coordinate system $P_1'P_2'P_3'$. In other words, it is desirable that the image creating unit 16c set the sample point $P_0$ based on the above described plate position data as the origin of the three-axis coordinate system $P_1P_2P_3$ as shown in FIG. 10. Such a setting will be described below.

Conceptually, the image creating unit 16c finds the guide image plane GF as follows. Firstly, the image creating unit 16c finds the coordinates of an optional point R(ts) on the two-dimensional image plane UF shown in FIG. 10 in the three-axis coordinate system $P_1P_2P_3$ using the position data which is associated with the two-dimensional image data in step S106 described above. By finding the coordinates, the image creating unit 16c can calculate the positional and orientational relations between the two-dimensional image plane UF and the three-axis coordinate system $P_1P_2P_3$.

Secondly, the image creating unit 16c finds a corresponding point R'(ts) which corresponds to the optional point R(ts) represented by the above mentioned coordinates, and which resides on the three-axis coordinate system $P_1'P_2'P_3'$ shown in FIG. 11, and sets a collection of the corresponding points R'(ts) as the guide image GF. Thus, the image creating unit 16c can derive the guide image plane GF whose positional and orientational relations with the three-axis coordinate system $P_1'P_2'P_3'$ are equal to the positional and orientational relations of the two-dimensional image plane UF with the three-axis coordinate system $P_1P_2P_3$.

When the guide image plane GF is found in the above described manner, the two-dimensional image plane UF and the guide image plane GF coincide with each other anatomically. This is because that though the anatomical structure of the human body and the shapes of the organs are different from one person to another depending on the constitutions, the anatomical structure and the shapes of the organs in an abdominal region are expected to be approximately the same among different sexes, and because that the four sample points $P_0$, $P_1$, $P_2$, and $P_3$ on the body surface of an actual subject, or on the surface of the lumen inside the subject anatomically correspond respectively to the four feature points $P_0'$, $P_1'$, $P_2'$, and $P_3'$ set on the slice image data group.

In practice, however, the image creating unit 16c finds the guide image plane GF as follows. To calculate the guide image plane GF means to calculate three vectors, i.e., the position vector O'C'(ts) of the central position C'(ts) of the guide image plane GF, the direction vector V'(ts) which indicates a direction of a normal line of the guide image plane GF, and the direction vector $V_{12}'$(ts) which indicates a direction of twelve o'clock of the guide image plane GF, on the orthogonal coordinate system x'y'z'. If the above mentioned three vectors are calculated, the guide image plane GF can be uniquely defined on the orthogonal coordinate system x'y'z'. Here, the image creating unit 16c calculates the above mentioned three vectors so that they anatomically coincide with the position vector OC(ts), of the central position C(ts) of the two-dimensional image plane UF, the direction vector V(ts) which indicates the direction of the normal line of the two-dimensional image plane UF, and the direction vector $V_{12}$(ts) which indicates a direction of twelve o'clock of the two-dimensional image plane UF, respectively, in order to make the two-dimensional image plane UF and the guide image plane GF anatomically coincide with each other. Therefore, in practice, the image creating unit 16c does not find the corresponding point R'(ts) as described above for each of all the optional points R(ts) on the two-dimensional image plane UF.

In the following, a concept of a manner to find the guide image plane GF will be described first. Then, as an actual manner of finding the guide image plane GF, a manner of calculating the central position of the guide image plane GF, the direction of normal line, and the direction of twelve o'clock will be described. In the following description of the concept of the guide image plane GF finding, plural equations will be mentioned. The equations are cited in order to describe an overall concept and to describe a background of equations actually employed in finding the guide image plane GF. In practice, the image creating unit 16c performs a numerical operating process to find the guide image plane GF based on equations described in relation to an actual manner of guide image plane GF finding.

The concept of finding the guide image plane GF described above will be described in more detail below. Here, a manner of making the optional point R(ts) on the two-dimensional image plane UF anatomically coincide with the corresponding point R'(ts) on the guide image plane GF will be mainly described.

A position vector $P_0R(ts)$ between the plate 9 and the optional point R(ts) can be represented on the three-axis coordinate system $P_1P_2P_3$ with appropriate actual numbers a, b, and c as the direction components as represented by the following equation (21):

$$P_0R(ts)=aP_0P_1(ts)+bP_0P_2(ts)+cP_0P_3(ts) \quad (21)$$

On the other hand, the feature points $P_0'$, $P_1'$, $P_2'$, and $P_3'$ are associated with the sample points $P_0$, $P_1$, $P_2$, and $P_3$, respectively, as anatomically identical positions. Further, though the anatomical structure of the human body and the shapes of the organs are different from one person to another depending on physical constitutions, anatomical structure and shapes of organs in an abdominal region are expected to be approximately the same among different sexes. Therefore, if the optional point R(ts) is located at a specific position relative to the three-axis coordinate system $P_1P_2P_3$, the corresponding point R'(ts) which is at a similar position relative to the three-axis coordinate system $P_1'P_2'P_3'$ can be regarded to correspond with a point which resides anatomically on the same organ or on the same tissue as the optional point R(ts). Therefore, assuming that the actual numbers a, b, and c in the equation (21) are the direction-components of the three-axis coordinate system $P_1P_2P_3$, a point which is on the orthogonal coordinate system x'y'z' which can be represented similarly to the equation (21) as shown by the following equation (22) can be regarded to be the corresponding point R'(ts) which anatomically corresponds to the optional point R(ts):

$$P_0'R'(ts)=aP_0'P_1'(ts)+bP_0'P_2'(ts)+cP_0'P_3'(ts) \quad (22)$$

Here, when the direction components of the position vector OR(ts) of the optional point R(ts) in the orthogonal coordinate system xyz are defined respectively as $x_R(ts)$, $y_R(ts)$, and $z_R(ts)$, and when the direction components of the position vector O'R'(ts) of the corresponding point R'(ts) on the orthogonal coordinate system x'y'z' are defined respectively as $X_R'(ts)$, $y_R'(ts)$, $z_R'(ts)$, the following equations (23) and (24) are satisfied:

$$OR(ts)=x_R(ts)i+y_R(ts)j+z_R(ts)k \quad (23)$$

$$O'R'(ts)=x_R'(ts)'+y_R'(ts)j'+z_R'(ts)k' \quad (24)$$

Further, based on the above described equation (21), the following equation (25) can be obtained:

$$OR(ts) - OP_0(ts) = \quad (25)$$
$$a(OP_1(ts) - OP_0(ts)) + b(OP_2(ts) - OP_0(ts)) + c(OP_3(ts) - OP_0(ts))$$

Then, based on the equations (25), (4) to (10), and (23), the following equation (26) can be obtained.

$$\begin{pmatrix} x_R(ts) \\ y_R(ts) \\ z_R(ts) \end{pmatrix} - \begin{pmatrix} x_{P0}(ts) \\ y_{P0}(ts) \\ z_{P0}(ts) \end{pmatrix} = \quad (26)$$
$$\begin{pmatrix} x_{P1}(ts) - x_{P0}(ts) & x_{P2}(ts) - x_{P0}(ts) & x_{P3}(ts) - x_{P0}(ts) \\ y_{P1}(ts) - y_{P0}(ts) & y_{P2}(ts) - y_{P0}(ts) & y_{P3}(ts) - y_{P0}(ts) \\ z_{P1}(ts) - z_{P0}(ts) & z_{P2}(ts) - z_{P0}(ts) & z_{P3}(ts) - z_{P0}(ts) \end{pmatrix} \begin{pmatrix} a \\ b \\ c \end{pmatrix}$$

Hereinbelow, for simplicity of the description of the equations, a 3×3 matrix Q(ts) is defined as the following equation (27):

$$Q(ts) = \begin{pmatrix} x_{P1}(ts) - x_{P0}(ts) & x_{P2}(ts) - x_{P0}(ts) & x_{P3}(ts) - x_{P0}(ts) \\ y_{P1}(ts) - y_{P0}(ts) & y_{P2}(ts) - y_{P0}(ts) & y_{P3}(ts) - y_{P0}(ts) \\ z_{P1}(ts) - z_{P0}(ts) & z_{P2}(ts) - z_{P0}(ts) & z_{P3}(ts) - z_{P0}(ts) \end{pmatrix} \quad (27)$$

Thus, the above described equation (26) can be transposed to the following equation (28):

$$\begin{pmatrix} x_R(ts) \\ y_R(ts) \\ z_R(ts) \end{pmatrix} - \begin{pmatrix} x_{P0}(ts) \\ y_{P0}(ts) \\ z_{P0}(ts) \end{pmatrix} = Q(ts) \begin{pmatrix} a \\ b \\ c \end{pmatrix} \quad (28)$$

Thus, the actual numbers a, b, and c can be obtained as in the following equation (29):

$$\begin{pmatrix} a \\ b \\ c \end{pmatrix} = Q(ts)^{-1} \left\{ \begin{pmatrix} x_R(ts) \\ y_R(ts) \\ z_R(ts) \end{pmatrix} - \begin{pmatrix} x_{P0}(ts) \\ y_{P0}(ts) \\ z_{P0}(ts) \end{pmatrix} \right\} \quad (29)$$

On the other hand, based on the above described equation (22), the following equation (30) can be obtained:

$$O'R'(ts) - O'P_0' = a(O'P_1' - O'P_0') + b(O'P_2' - O'P_0') \quad (30)$$

Then, similarly to the derivation of the above described equation (26), based on the equations (30), (11) to (14), and (24), the following equation (31) can be obtained:

$$\begin{pmatrix} x_R'(ts) \\ y_R'(ts) \\ z_R'(ts) \end{pmatrix} - \begin{pmatrix} x_{P0}' \\ y_{P0}' \\ z_{P0}' \end{pmatrix} = \begin{pmatrix} x_{P1}' - x_{P0}' & x_{P2}' - x_{P0}' & x_{P3}' - x_{P0}' \\ y_{P1}' - y_{P0}' & y_{P2}' - y_{P0}' & y_{P3}' - y_{P0}' \\ z_{P1}' - z_{P0}' & z_{P2}' - z_{P0}' & z_{P3}' - z_{P0}' \end{pmatrix} \begin{pmatrix} a \\ b \\ c \end{pmatrix} \quad (31)$$

Hereinbelow, for simplicity of the description of the equations, a 3×3 matrix Q' is defined as the following equation (32):

$$Q' = \begin{pmatrix} x_{P1}' - x_{P0}' & x_{P2}' - x_{P0}' & x_{P3}' - x_{P0}' \\ y_{P1}' - y_{P0}' & y_{P2}' - y_{P0}' & y_{P3}' - y_{P0}' \\ z_{P1}' - z_{P0}' & z_{P2}' - z_{P0}' & z_{P3}' - z_{P0}' \end{pmatrix} \quad (32)$$

Thus, the above described equation (31) can be transposed to the following equation (33):

$$\begin{pmatrix} x_R'(ts) \\ y_R'(ts) \\ z_R'(ts) \end{pmatrix} - \begin{pmatrix} x_{P0}' \\ y_{P0}' \\ z_{P0}' \end{pmatrix} = Q' \begin{pmatrix} a \\ b \\ c \end{pmatrix} \quad (33)$$

Thus, based on the above described equations (29) and (33), the following equation (34) is obtained. Then, the following equation (35) is obtained. In the equations (34) and (35), the matrix $Q(ts)^{-1}$ is an inverse matrix of the matrix $Q(ts)$.

$$\begin{pmatrix} x_R'(ts) \\ y_R'(ts) \\ z_R'(ts) \end{pmatrix} - \begin{pmatrix} x_{P0}' \\ y_{P0}' \\ z_{P0}' \end{pmatrix} = Q' Q(ts)^{-1} \left\{ \begin{pmatrix} x_R(ts) \\ y_R(ts) \\ z_R(ts) \end{pmatrix} - \begin{pmatrix} x_{P0}(ts) \\ y_{P0}(ts) \\ z_{P0}(ts) \end{pmatrix} \right\} \quad (34)$$

$$\begin{pmatrix} x_R'(ts) \\ y_R'(ts) \\ z_R'(ts) \end{pmatrix} = \begin{pmatrix} x_{P0}' \\ y_{P0}' \\ z_{P0}' \end{pmatrix} + Q' Q(ts)^{-1} \left\{ \begin{pmatrix} x_R(ts) \\ y_R(ts) \\ z_R(ts) \end{pmatrix} - \begin{pmatrix} x_{P0}(ts) \\ y_{P0}(ts) \\ z_{P0}(ts) \end{pmatrix} \right\} \quad (35)$$

Thus, analytically based on the equations (24) and (35), the position vector O'R'(ts) of the anatomically corresponding point R'(ts) of the optional point R(ts) on the two-dimensional image plane UF in the orthogonal coordinate system xyz, and the direction components $X_R'(ts)$, $y_R'(ts)$, and $Z_R'(ts)$ thereof in the orthogonal coordinate system x'y'z' are found. Thus, the guide image plane GF is a collection of corresponding points R'(ts) which can be calculated from the equations (24) and (35) with respect to the optional point R(ts) on the two-dimensional image plane UF, with the use of the coordinate data of the feature point stored in the image storing unit 14 by the controlling unit 16 in step S101, the coordinate data of the sample point stored in the storing unit 16a by the controlling unit 16 in step S102, and the position data associated with the two-dimensional image data at the time ts and stored in the storing unit 16a by the controlling unit 16 in step S106.

Then, an actual manner of finding the above described guide image plane GF will be described in detail. Hereinbelow, an actual manner taken by the image creating unit 16c to find the guide image plane GF will be mainly described, in which the position data that determines the central position C'(ts) and the orientation of the guide image plane GF described above, i.e., the position vector O'C'(ts) in the orthogonal coordinate system x'y'z', the direction vector V'(ts), and the direction vector $V_{12}'(ts)$ are calculated with the use of the position data associated with the two-dimensional image data at the time ts, i.e., the position vector OC(ts) of the central position C(ts), the direction vector V(ts), and the direction vector $V_{12}(ts)$ of the two-dimensional image plane UF.

Firstly, a manner of finding the position vector O'C'(ts) will be described. The image creating unit 16c performs a coordinate converting process which is substantially the same with the equation (35) described above using the three-axis coordinate systems $P_1P_2P_3$, and $P_1'P_2'P_3'$ described above and the position vector OC(ts) under the control of the controlling unit 16, and calculates the position vector O'C'(ts). Here, since the central position C(ts) is set in the orthogonal coordinate system xyz, the position vector OC(ts) can be represented by the following equation (36). Further, since the central position C'(ts) is set in the orthogonal coordinate system x'y'z', the position vector O'C'(ts) can be represented by the following equation (37):

$$OC(ts) = x_C(ts)i + y_C(ts)j + z_C(ts)k \quad (36)$$

$$O'C'(ts) = x_C'(ts)i' + y_C'(ts)j' + z_C'(ts)k' \quad (37)$$

In the equation (36), the direction components $x_C(ts)$, $y_C(ts)$, $z_C(ts)$ are coordinate components of the position vector OC(ts), respectively in the x-axis direction, the y-axis direction, and the z-axis direction. Further, in the equation (37), the direction components $x_C'(ts)$, $y_C'(ts)$, and $z_C'(ts)$ are coordinate components of the position vector O'C'(ts), respectively in the x'-axis direction, the y'-axis direction, and the z'-axis direction.

In the above described equation (35), when the optional point R(ts) is replaced with the central position C(ts), and the corresponding point R'(ts) is replaced with the central position C'(ts), the following equation (38) is obtained. The image creating unit 16c can find the coordinate data of the central position C'(ts) of the guide image plane GF based on the equation (38). Thus, the image creating unit 16c sets the central positions C(ts) and C'(ts) on the two-dimensional image plane UF and the guide image plane GF, respectively, as shown in FIGS. 10 and 11, and determines the respective central positions so that the two-dimensional image plane UF and the guide image plane GF anatomically correspond with each other.

$$\begin{pmatrix} x'_c(ts) \\ y'_c(ts) \\ z'_c(ts) \end{pmatrix} - \begin{pmatrix} x'_{P0} \\ y'_{P0} \\ z'_{P0} \end{pmatrix} = Q'Q(ts)^{-1} \left\{ \begin{pmatrix} x_c(ts) \\ y_c(ts) \\ z_c(ts) \end{pmatrix} - \begin{pmatrix} x_{P0}(ts) \\ y_{P0}(ts) \\ z_{P0}(ts) \end{pmatrix} \right\} \quad (38)$$

Secondly, a manner of finding the direction vector $V_{12}'$(ts) that indicates a direction of twelve o'clock on the guide image plane GF will be described. Based on the assumption that there is a unit point $R_{12}$(ts) which is a unit distance away from the central position C(ts) of the two-dimensional image plane UF in a direction of twelve o'clock based on the optional point R(ts), the direction vector $V_{12}'$(ts) of the guide image plane GF is derived based on the assumed unit point $R_{12}$(ts). Here, since the unit point $R_{12}$(ts) is set in the orthogonal coordinate system xyz, the position vector $OR_{12}$(ts) is represented by the following equation (39):

$$OR_{12}(ts) = x_{R12}(ts)i + y_{R12}(ts)j + z_{R12}(ts)k \quad (39)$$

In the equation (39), the direction components $X_{R12}$(ts), $y_{R12}$(ts), and $z_{R12}$(ts) are coordinate components of the position vector $OR_{12}$(ts) in the x-axis direction, the y-axis direction, and the z-axis direction, respectively.

Further, since the unit point $R_{12}'$(ts) which anatomically corresponds to the unit point $R_{12}$(ts) is a point on the guide image plane GF that is set in the orthogonal coordinate system x'y'z', the position vector $O'R_{12}'$(ts) can be represented by the following equation (40):

$$O'R_{12}'(ts) = x_{R12}'(ts)i' + y_{R12}'(ts)j' + z_{R12}'(ts)k' \quad (40)$$

In the equation (40), the direction components $X_{R12}'$(ts), $y_{R12}'$(ts), and $Z_{R12}'$(ts) are coordinate components of the position vector $O'R_{12}'$(ts) in the x'-axis direction, the y'-axis direction, and the z'-axis direction, respectively.

In the equation (35) described above, when the optional point R(ts) is replaced with the unit point $R_{12}$(ts), and the corresponding point R'(ts) is replaced with the unit point $R_{12}'$(ts), the following equation (41) is obtained. Based on the equations (40) and (41), the coordinate data of the unit point $R_{12}'$(ts) of the guide image plane GF can be obtained.

$$\begin{pmatrix} x'_{R12}(ts) \\ y'_{R12}(ts) \\ z'_{R12}(ts) \end{pmatrix} - \begin{pmatrix} x'_{P0} \\ y'_{P0} \\ z'_{P0} \end{pmatrix} + Q'Q(ts)^{-1} \left\{ \begin{pmatrix} x_{R12}(ts) \\ y_{R12}(ts) \\ z_{R12}(ts) \end{pmatrix} - \begin{pmatrix} x_{P0}(ts) \\ y_{P0}(ts) \\ z_{P0}(ts) \end{pmatrix} \right\} \quad (41)$$

Here, the position vector $OR_{12}$(ts) of the unit point $R_{12}$(ts) can be represented by the following equation (42) with the use of the position vector OC(ts) and the direction vector $V_{12}$(ts):

$$OR_{12}(ts) = OC(ts) + V_{12}(ts) \quad (42)$$

Hence, the direction vector $V_{12}$(ts) can be represented by the following equation (43) with the use of the position vectors $OR_{12}$(ts), and OC(ts):

$$V_{12}(ts) = OR_{12}(ts) - OC(ts) \quad (43)$$

The image creating unit 16c can find the direction vector $V_{12}'$(ts) by standardizing the difference between the position vector O'C'(ts) and the position vector $O'R_{12}'$(ts) to a unit length based on the equation (43). The direction vector $V_{12}'$(ts) can be represented by the following equation (44):

$$V_{12}'(ts) = (O'R_{12}'(ts) - O'C'(ts))/|O'R_{12}'(ts) - O'C'(ts)| \quad (44)$$

Thus, the image creating unit 16c sets the direction vectors $V_{12}$(ts) and $V_{12}'$(ts) as shown in FIGS. 10 and 11 on the two-dimensional image plane UF and the guide image plane GF, respectively, and determines the direction of twelve o'clock for each of the two-dimensional image plane UF and the guide image plane GF, so that the two-dimensional image plane UF and the guide image plane GF anatomically correspond with each other.

The direction components $xv_{12}'$(ts), $yv_{12}'$(ts), and $zv_{12}'$(ts) of the direction vector $V_{12}'$(ts) in respective axis directions in the orthogonal coordinate system x'y'z', i.e., the coordinate data of the direction vector $V_{12}'$(ts) calculated by the image creating unit 16c will be described in detail. As described above, the direction vector $V_{12}'$(ts) is calculated based on the difference between the position vector $O'R_{12}'$(ts) and the position vector O'C'(ts) The coordinate data based on the difference in position vectors is represented by the following equation (45) based on the above described equations (38) and (41).

$$\begin{pmatrix} x'_{R12}(ts) \\ y'_{R12}(ts) \\ z'_{R12}(ts) \end{pmatrix} - \begin{pmatrix} x'_c(ts) \\ y'_c(ts) \\ z'_c(ts) \end{pmatrix} = Q'Q(ts)^{-1} \left\{ \begin{pmatrix} x_{R12}(ts) \\ y_{R12}(ts) \\ z_{R12}(ts) \end{pmatrix} - \begin{pmatrix} x_c(ts) \\ y_c(ts) \\ z_c(ts) \end{pmatrix} \right\} \quad (45)$$

The right side of the equation (45) can be represented by the coordinate data of the direction vector $V_{12}$(ts), i.e., the direction components $xv_{12}$(ts), $yv_{12}$(ts), and $zv_{12}$(ts) in the respective axis directions of the orthogonal coordinate system xyz based on the equation (43), whereby the following equation (47) is obtained. The direction vector $V_{12}$(ts) can be represented by the following equation (46) with the direction components $xv_{12}$(ts), $yv_{12}$(ts), and $zv_{12}$(ts):

$$V_{12}(ts) = xv_{12}(ts)i + yv_{12}(ts)j + zv_{12}(ts)k \quad (46)$$

$$\begin{pmatrix} x'_{R12}(ts) \\ y'_{R12}(ts) \\ z'_{R12}(ts) \end{pmatrix} - \begin{pmatrix} x'_c(ts) \\ y'_c(ts) \\ z'_c(ts) \end{pmatrix} = Q'Q(ts)^{-1} \begin{pmatrix} xv_{12}(ts) \\ yv_{12}(ts) \\ zv_{12}(ts) \end{pmatrix} \quad (47)$$

Since the direction vector $V_{12}'$(ts) is calculated based on the standardization of the above described difference between the position vector $O'R_{12}'$(ts) and the position vector O'C'(ts) to the unit length, the direction vector $V_{12}'$(ts) can be obtained by the standardization of the right side of the equation (47) to the unit length. Then, the following equation (49) is obtained. The direction vector $V_{12}'$(ts) is represented by the following equation (48) with the direction components $xv_{12}'$(ts), $yv_{12}'$(ts), and $zv_{12}'$(ts)

$$V_{12}'(ts) = xv_{12}'(ts)i' + yv_{12}'(ts)j' + zv_{12}'(ts)k' \quad (48)$$

$$\begin{pmatrix} xv_{12}'(ts) \\ yv_{12}'(ts) \\ zv_{12}'(ts) \end{pmatrix} = \frac{Q'Q(ts)^{-1} \begin{pmatrix} xv_{12}(ts) \\ yv_{12}(ts) \\ zv_{12}(ts) \end{pmatrix}}{\left| Q'Q(ts)^{-1} \begin{pmatrix} xv_{12}(ts) \\ yv_{12}(ts) \\ zv_{12}(ts) \end{pmatrix} \right|} \quad (49)$$

Thirdly, a manner of finding the direction vector V'(ts) that indicates the direction of the normal line of the guide image plane GF will be described. The image creating unit 16c calculates a vector that intersects with all the vectors formed by the optional points on the guide image plane GF anatomically corresponding to the two-dimensional image plane UF, as the normal vector, i.e., as the direction vector V'(ts). Assume that there are two optional points $R_1(ts)$ and $R_2(ts)$ on the two-dimensional image plane UF, and there are two corresponding points $R_1'(ts)$ and $R_2'(ts)$ that are on the guide image plane and that anatomically correspond, respectively, to the optional points $R_1(ts)$ and $R_2(ts)$. The position vectors $OR_1(ts)$ and $OR_2(ts)$ of the optional points $R_1(ts)$ and $R_2(ts)$ are represented by the following equations (50) and (51):

$$OR_1(ts) = x_{R1}(ts)i + y_{R1}(ts)j + z_{R1}(ts)k \qquad (50)$$

$$OR_2(ts) = x_{R2}(ts)i + y_{R2}(ts)j + z_{R2}(ts)k \qquad (51)$$

In the equation (50), the direction components $x_{R1}(ts)$, $y_{R1}(ts)$, and $z_{R1}(ts)$ are coordinate components of the position vector $OR_1(ts)$ in the x-axis direction, the y-axis direction, and the z-axis direction, respectively. Further in the equation (51), the direction components $x_{R2}(ts)$, $y_{R2}(ts)$, and $z_{R2}(ts)$ are coordinate components of the position vector $OR_2(ts)$ in the x-axis direction, the y-axis direction, and the z-axis direction, respectively.

The position vectors $O'R_1'(ts)$ and $O'R_2'(ts)$ of the corresponding points $R_1'(ts)$ and $R_2'(ts)$ can be represented by the following equations (52) and (53), respectively:

$$O'R_1'(ts) = x_{R1}'(ts)i' + y_{R1}'(ts)j' + z_{R1}'(ts)k' \qquad (52)$$

$$O'R_2'(ts) = x_{R2}'(ts)i' + y_{R2}'(ts)j' + z_{R2}'(ts)k' \qquad (53)$$

In the equation (52), the direction components $x_{R1}'(ts)$, $y_{R1}'(ts)$, and $z_{R1}'(ts)$ are coordinate components of the position vector $O'R_1'(ts)$ in the x'-axis direction, the y'-axis direction, and the z'-axis direction, respectively. Further in the equation (53), the direction components $x_{R2}'(ts)$, $y_{R2}'(ts)$, and $z_{R2}'(ts)$ are coordinate components of the position vector $O'R_2'(ts)$ in the x'-axis direction, the y'-axis direction, and the z'-axis direction, respectively.

Further, based on the above described equation (35), and with the coordinate data of the position vectors $OR_1(ts)$ and $OR_2(ts)$, and the coordinate data of the position vectors $O'R_1'(ts)$ and $O'R_2'(ts)$, the following equations (54) and (55) are obtained:

$$\begin{pmatrix} x_{R1}'(ts) \\ y_{R1}'(ts) \\ z_{R1}'(ts) \end{pmatrix} = \begin{pmatrix} x_{P0}' \\ y_{P0}' \\ z_{P0}' \end{pmatrix} + Q'Q(ts)^{-1}\left\{\begin{pmatrix} x_{R1}(ts) \\ y_{R1}(ts) \\ z_{R1}(ts) \end{pmatrix} - \begin{pmatrix} x_{P0}(ts) \\ y_{P0}(ts) \\ z_{P0}(ts) \end{pmatrix}\right\} \qquad (54)$$

$$\begin{pmatrix} x_{R2}'(ts) \\ y_{R2}'(ts) \\ z_{R2}'(ts) \end{pmatrix} = \begin{pmatrix} x_{P0}' \\ y_{P0}' \\ z_{P0}' \end{pmatrix} + Q'Q(ts)^{-1}\left\{\begin{pmatrix} x_{R2}(ts) \\ y_{R2}(ts) \\ z_{R2}(ts) \end{pmatrix} - \begin{pmatrix} x_{P0}(ts) \\ y_{P0}(ts) \\ z_{P0}(ts) \end{pmatrix}\right\} \qquad (55)$$

Thereafter, by subtracting the right side and the left side of the equation (55) from those of the equation (54), respectively, the following equation (56) is obtained.

$$\begin{pmatrix} x_{R1}'(ts) \\ y_{R1}'(ts) \\ z_{R1}'(ts) \end{pmatrix} - \begin{pmatrix} x_{R2}'(ts) \\ y_{R2}'(ts) \\ z_{R2}'(ts) \end{pmatrix} = Q'Q(ts)^{-1}\left\{\begin{pmatrix} x_{R1}(ts) \\ y_{R1}(ts) \\ z_{R1}(ts) \end{pmatrix} - \begin{pmatrix} x_{R2}(ts) \\ y_{R2}(ts) \\ z_{R2}(ts) \end{pmatrix}\right\} \qquad (56)$$

Further, by multiplying the respective sides of the equation (56) with $Q(ts)Q'^{-1}$ from the left, the following equation (57) is obtained.

$$\begin{pmatrix} x_{R1}(ts) \\ y_{R1}(ts) \\ z_{R1}(ts) \end{pmatrix} - \begin{pmatrix} x_{R2}(ts) \\ y_{R2}(ts) \\ z_{R2}(ts) \end{pmatrix} = Q(ts)Q'^{-1}\left\{\begin{pmatrix} x_{R1}'(ts) \\ y_{R1}'(ts) \\ z_{R1}'(ts) \end{pmatrix} - \begin{pmatrix} x_{R2}'(ts) \\ y_{R2}'(ts) \\ z_{R2}'(ts) \end{pmatrix}\right\} \qquad (57)$$

The direction vector V(ts) of the two-dimensional image plane UF is represented by the following equation (58) with the direction components xv(ts), yv(ts), and zv(ts) of the orthogonal coordinate system xyz in the respective axis directions:

$$V(ts) = xv(ts)i + yv(ts)j + zv(ts)k \qquad (58)$$

Since the direction vector V(ts) is the two-dimensional image data at the time ts, i.e., the normal vector in the two-dimensional image plane UF, the direction vector V(ts) intersects with the vector $R_2R_1(ts)$ that connects the optional points $R_1(ts)$ and $R_2(ts)$. Based on the above, the following equation (59) can be obtained. In the equation (59), an inner product $V(ts) \cdot R_2R_1(ts)$ is an inner product of the direction vector V(ts) and the vector $R_2R_1(ts)$ $$0 = V(ts) \cdot R_2R_1(ts) \qquad (59)$$

$$= \begin{pmatrix} xv(ts) & yv(ts) & zv(ts) \end{pmatrix}\left\{\begin{pmatrix} x_{R1}(ts) \\ y_{R1}(ts) \\ z_{R1}(ts) \end{pmatrix} - \begin{pmatrix} x_{R2}(ts) \\ y_{R2}(ts) \\ z_{R2}(ts) \end{pmatrix}\right\}$$

Further, based on the equations (57) and (59), the following equation (60) is obtained:

$$\begin{pmatrix} xv(ts) & yv(ts) & zv(ts) \end{pmatrix}Q(ts)Q'^{-1}\left\{\begin{pmatrix} x_{R1}'(ts) \\ y_{R1}'(ts) \\ z_{R1}'(ts) \end{pmatrix} - \begin{pmatrix} x_{R2}'(ts) \\ y_{R2}'(ts) \\ z_{R2}'(ts) \end{pmatrix}\right\} = 0 \qquad (60)$$

Here, the direction vector V'(ts) of the guide image plane GF is represented by the following equation (61) with the use of the direction components xv'(ts), yv'(ts), and zv'(ts) of the orthogonal coordinate system x'y'z' in the respective axis directions:

$$V'(ts) = xv'(ts)i' + yv'(ts)j' + zv'(ts)k' \qquad (61)$$

Further, the direction components xv'(ts), yv'(ts), and zv'(ts) of the direction vector V'(ts) are defined so as to satisfy the following equation (62):

$$(xv'(ts)\ yv'(ts)\ zv'(ts)) = (xv(ts)\ yv(ts)\ zv(ts))Q(ts)Q'^{-1} \qquad (62)$$

According to the above definition, the following equation (63) is obtained based on the above described equations (60) and (62), in turn, the following equation (64) is obtained.

$$\begin{pmatrix} xv'(ts) & yv'(ts) & zv'(ts) \end{pmatrix}\left\{\begin{pmatrix} x_{R1}'(ts) \\ y_{R1}'(ts) \\ z_{R1}'(ts) \end{pmatrix} - \begin{pmatrix} x_{R2}'(ts) \\ y_{R2}'(ts) \\ z_{R2}'(ts) \end{pmatrix}\right\} = 0 \qquad (63)$$

$$V'(ts) \cdot R_2'R_1'(ts) = 0 \qquad (64)$$

In the equation (64), the vector R2'R1'(ts) is a vector connecting the corresponding points R1'(ts) and R2'(ts) on the guide image plane GF.

Here, the equation (64) indicates that the direction vector V'(ts) intersects with all the vectors connecting the optional points on the guide image plane GF. In other words, the direction vector V'(ts) based on the above described equations (61) and (62) is a normal vector determining the direction of a normal line in the guide image plane GF. Therefore, the image creating unit 16c can calculate the direction vector V'(ts) that determines the direction of normal line of the guide image plane GF based on the above described equations (61) and (62). Thus, the image creating unit 16c, as shown in FIGS. 10 and 11, sets the direction vectors V(ts) and V'(ts) on the two-dimensional image plane UF and the guide image plane GF, respectively, and determines the direction of normal line of each plane so that the two-dimensional image plane UF and the guide image plane GF anatomically correspond with each other.

Thus, the image creating unit 16c can find the orientation (central position, direction of normal line, direction of twelve o'clock) of the guide image plane GF calculated in step S401 described above under the control of the controlling unit 16, and the image creating unit 16c can set the guide image plane GF, with which the above orientation is associated, as an image plane which anatomically corresponds to the two-dimensional image plane UF.

Then, the controlling unit 16, in response to the setting of the guide image plane GF by the image creating unit 16c as a trigger, reads out the slice image data group that corresponds to the guide image plane GF from the image storing unit 14 (step S402). Specifically, the controlling unit 16 reads out image data which is located on an intersecting line of each piece of the slice image data of the slice image data group and the guide image plane GF based on the position data of the position and the orientation of the guide image plane GF obtained in step S401 described above. The image creating unit 16c performs the interpolating process, the coordinate converting process, or the like on the read out slice image data group located on the intersecting line, and creates guide image data corresponding to a sectional image along the guide image plane GF from the slice image data group stored in the image storing unit 14 (step S403). Subsequently, the controlling unit 16 performs the processing procedure of step S109 described above.

In the first embodiment of the present invention, the controlling unit 16 sets the feature point on the slice image data based on the coordinate information, which is input by the operator through the input device 11, of the feature point. The present invention, however, is not limited to the above arrangement. When an interest region or a protocol of the examination is determined in advance, plural sets of feature points may be stored in the image storing unit 14 as the default coordinate data together with the slice image data group at the time of shipment from the manufacturing facility. Then, the controlling unit 16 may read out the default coordinate data of the feature points from the image storing unit 14 and set the feature point according to the read out data based on command information supplied from the input device 11 for the selection of feature points.

In the first embodiment of the present invention, at the setting of the feature points, the controlling unit 16, based on the image display command information sequentially supplied through the input device 11 by an input manipulation of the operator, sequentially reads out the slice image data group starting from a leading piece arranged first in the sequence to a last piece arranged last in the sequence, and the controlling unit 16 sequentially outputs and displays the read out data on the screen of the display device 12. The present invention, however, is not limited to the above arrangement. The slice image data group may be collectively read out based on the image display command information, and the slice images may be displayed on the screen of the display device 12 in a list format.

Further, in the first embodiment of the present invention, the plate 9 or the marker coil 8 is attached to each of previously determined plural positions of the subject, such as the ensiform cartilage and the pelvis. The fluctuations in various types of position data attributable to the change in posture of the subject or the difference in physical constitutions of the subjects are corrected. After the correction, the marker coil 8 is detached from the subject while the plate 9 remains on the body surface of the subject. Based on the position data obtained from the alternating magnetic field from the remaining plate 9, the fluctuations in the coordinate data of the sample point caused by the change in posture of the subject during the examination is corrected. The present invention, however, is not limited to the above arrangement. The posture of the subject may be made unchangeable through anesthesia or the like immediately before the examination and the sample point may be sequentially set based on the position data obtained from the alternating magnetic field of the marker coil 8, or alternatively, the subsequent correction of the coordinate data of the sample point may be omitted. Still alternatively, the fluctuation in the coordinate data of the sample point attributable to the change in posture of the subject may be corrected based on the alternating magnetic field output from the plate 9 and the marker coil 8 attached on the body surface of the subject during the examination. According to such an arrangement, preciseness of the guide image anatomically corresponding to the two-dimensional ultrasound image can be enhanced by the attachment of the marker coil 8 at a suitable position.

Further, in the first embodiment of the present invention, the guide image plane is set through the calculation of the position and the orientation of the guide image plane (central position, direction of normal line, direction of twelve o'clock). The present invention, however, is not limited to the above arrangement. For example, coordinate points of four corners of the obtained two-dimensional image data may be detected; four coordinate points anatomically corresponding to the coordinate points of the four corners, respectively, are found; and the guide image plane may be calculated based on the four coordinate points based on the equation (35) described above. Still alternatively, command information concerning the size of the guide image, e.g., numerical information, selection information, or the like in which the display size and the display magnification are previously reflected may be input from the input device 11 by a command or a selection, and the size of the guide image plane may be determined based on the supplied command information.

Still further, in the first embodiment of the present invention, the first coil and the second coil of the transmission coil 7 are arranged near the ultrasonic transducer 3a so that the first coil and the second coil intersect with each other; while the direction of one coil axis is arranged in the direction of normal line of the two-dimensional image data, and the direction of another coil axis is arranged in the direction of twelve o'clock of the two-dimensional image data. The present invention, however, is not limited to the above arrangement. Alternatively, the first coil and the second coil may be arranged at fixed positions relative to the ultrasonic transducer 3a, while the direction of the coil axis of the first coil or the direction of the coil axis of the second coil is arranged in a known direction, and the direction of normal line and the direction of twelve o'clock of the two-dimensional image data may be corrected and calculated based on the positional relation relative to the known direction. Still alternatively, the first coil and the second coil may be arranged in an inclined manner, and the direction of normal line and the direction of twelve o'clock of the two-dimensional image data may be corrected and calculated based on the directions of coil axes of the first coil and the second coil. With such an arrangement, the insertion portion 3 of the probe 2 can be made even thinner.

In the first embodiment of the present invention, the position data of the ultrasonic transducer 3a is detected through the reception of the alternating magnetic field from the transmission coil 7 in the probe 2 by the receiver coil 10. The present invention, however, is not limited thereto. Alternatively, the receiver coil 10 may be arranged in the probe 2, while the transmission coil 7 may be arranged in the position data calculating device 6. The alternating magnetic field from the transmission coil 7 may be received by the receiver coil 10 in the probe 2, whereby the position data of the ultrasonic transducer 3a may be detected. Still alternatively, in place of the alternating magnetic field from the transmission coil 7, acceleration or the like caused by the change in relative position of the ultrasonic transducer 3a relative to the interior of the subject body may be employed for the detection of the position and the orientation of the two-dimensional image data.

Still further, in the first embodiment of the present invention, the origin O of the orthogonal coordinate system xyz is set at a predetermined position of the receiver coil 10, e.g., near the central axis of the alternating magnetic field receiving surface. The present invention, however, is not limited to the above arrangement. The origin O may be set at any desirable position whose relative positional relation with the receiver coil 10 does not change.

Still further, in the first embodiment of the present invention, the slice image data is previously created based on photograph data which is sectional images of a frozen human body other than the body of the subject, and the guide image is created from the slice image data. The present invention, however, is not limited to the above arrangement. For example, the radial scan may be performed on the subject or a human body other than that of the subject with the ultrasonic diagnosis apparatus 1 or a similar ultrasonic diagnosis apparatus, and a two-dimensional image data group may be obtained. Images included in the two-dimensional image data group may be colored with respect to organs, and a colored image data group is created and stored previously in the image storing unit 14. Then, the colored image data group may be employed in place of the above described slice image data group. Still alternatively, three-dimensional image data may be obtained in advance with an extracorporeal type ultrasonic diagnosis apparatus which employs a modality other than ultrasound, such as Position Emission Tomography (PET) or which irradiates the ultrasound from outside the subject body. The obtained three-dimensional image data may be previously stored in the image storing unit 14, and the feature points may be set and the guide image may be created based on the stored three-dimensional image data.

As described above, in the first embodiment of the present invention, the slice image data group, which is the anatomical image data colored with respect to organs, is previously stored. The feature point is set in the orthogonal coordinate system x'y'z' of the slice image data group. Further, the sample point is set in the orthogonal coordinate system xyz of the subject so that the sample point anatomically corresponds with the feature point. Further, the two-dimensional image data inside the subject obtained through the radial scan and the position data concerning the position and the orientation of the two-dimensional image plane thereof are obtained. The two-dimensional image plane is converted from the orthogonal coordinate system xyz to the orthogonal coordinate system x'y'z' with the use of the coordinate data of four feature points among at least four set feature points, the coordinate data of the four sample points that anatomically correspond to the four feature points among at least four set sample points, and the position data of the two-dimensional image plane. Thus, the guide image plane which anatomically corresponds to the two-dimensional image plane is created. Then, the guide image data anatomically corresponding to the two-dimensional image data is created based on the position data concerning the position and the orientation of the guide image plane and the slice image data group. Then, the two-dimensional ultrasound image corresponding to the two-dimensional image data and the guide image corresponding to the guide image data are output and displayed on the same screen in an aligned manner. Thus realized is an ultrasonic diagnosis apparatus which can sequentially output and display in real time the two-dimensional ultrasound image together with the guide image which anatomically correctly corresponds to the two-dimensional ultrasound image in terms of the position and orientation of the presented organs or the like, and which includes displays of the annotation information such as an abbreviation of each organ, and the like, and which displays organ images each in different colors.

Further, when the coordinate data of the sample point set in the past, i.e., before the current time differs from the coordinate data of the current sample point due to the change in posture of the subject or the like, such difference is corrected so that the past sample point is updated to the current sample point. Hence, the guide image data which anatomically corresponds to the two-dimensional image data sequentially obtained in real time can be correctly obtained, and the correctness of the anatomical correspondence between the two-dimensional ultrasound image and the guide image which is output and displayed together with the two-dimensional ultrasound image can be enhanced.

Still further, the coordinate data of two sample points among the above described four sample points are detected based on the alternating magnetic fields from the plate and the marker coil respectively arranged near the body surface, for example, at the ensiform cartilage and the right end of the pelvis of the subject, and the coordinate data of the remaining two sample points are detected based on the alternating magnetic field from the transmission coil arranged at random inside the subject body, for example, near the pylorus and duodenal papilla. Therefore, compared with the detection of the coordinate data of the four sample points from the body surface of the subject with the probe incorporating the transmission coil, a trouble of cleaning the probe before the operation can be reduced. Further, the sample point can be set at a position corresponding to a position inside the subject while the probe incorporating the transmission coil is inside the subject body. Therefore, the sample point can be set at a position inside the body following the movement and positional change of the target interest region inside the body caused by the movement of the probe. Still further, the sample point can be set at a position inside the body near the target interest region. Thus, the correctness of anatomical correspondence between the guide image and the two-dimensional ultrasound image can be enhanced. Specifically, the pylorus and the duodenal papilla may move inside the body together with the head of pancreas according to the movement of the insertion portion of the probe. However, since these regions can be set as the sample point, the anatomical correctness of the guide image can be enhanced.

By employing the ultrasonic diagnosis apparatus, the operator can simultaneously confirm the two-dimensional ultrasound image and the guide image. For example, the operator can correctly and easily recognize which portion of the subject the current two-dimensional ultrasound image anatomically indicates by referring to the colored organ images in the guide image. Therefore, the operator can easily locate the interest region, such as pathological lesions or the like inside the subject body, correctly observe the interest region, and make a medical diagnosis of the subject correctly and efficiently. Therefore, the ultrasonic diagnosis apparatus of the present invention is far more useful in medical term compared with an ultrasonic diagnosis apparatus which irradiates the ultrasound from outside the subject body. In particular, the above described ultrasonic diagnosis apparatus largely contributes to the reduction of examination time of the, subject and the reduction of learning time of an immature operator.

A second embodiment of the present invention will be described in detail. In the first embodiment described above, the guide image data is created with the use of the slice image data group previously stored in the image storing unit 14. In the second embodiment, anatomical image data is created with a diagnostic imaging apparatus such as a three-dimensional magnetic resonance imaging (MRI) apparatus, and an X-ray three-dimensional helical computer tomography (CT) apparatus. The anatomical image data is obtained via a network and the guide image data is created based on the obtained anatomical image data.

Figure 12:
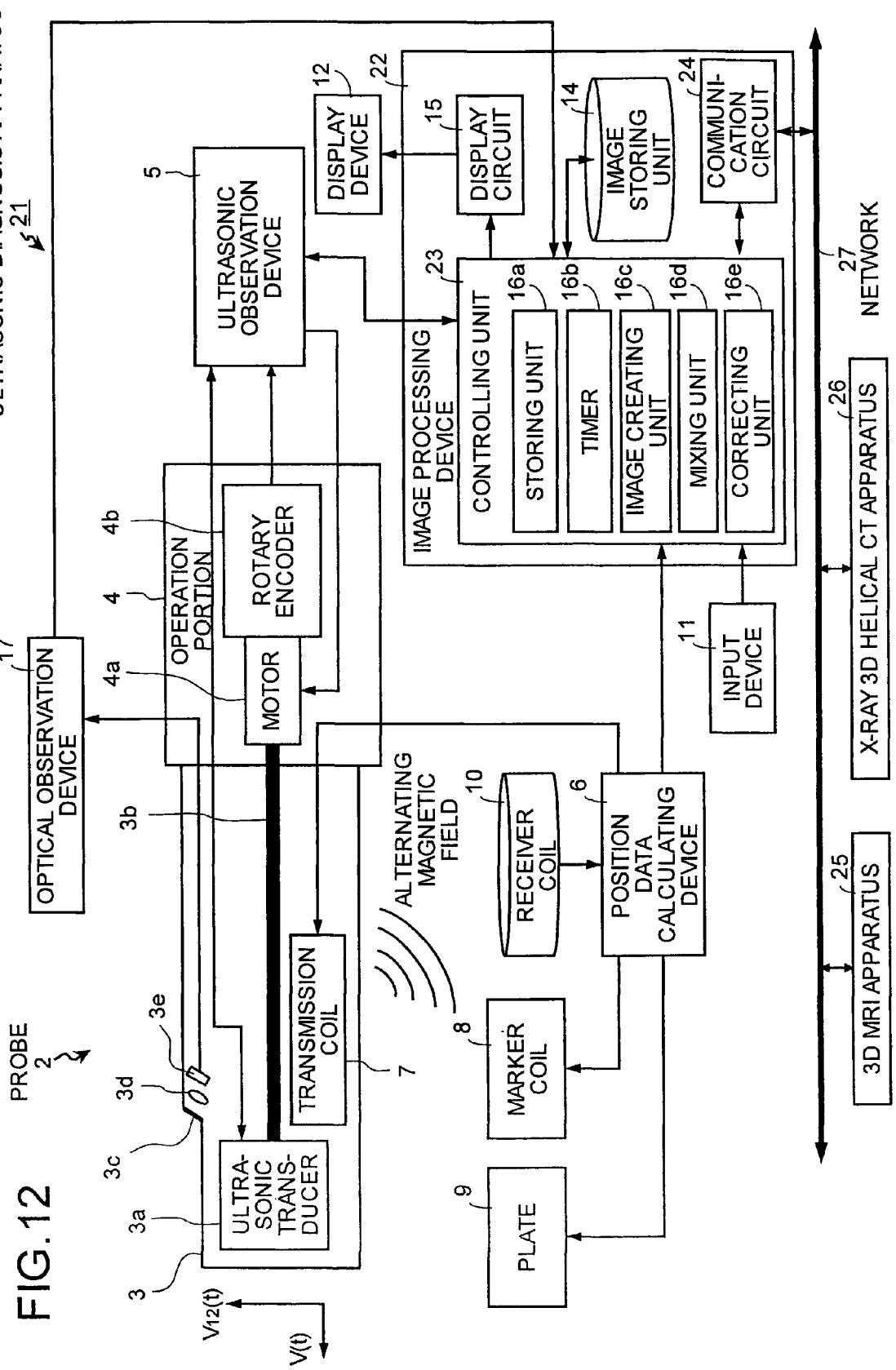
FIG. 12 is a block diagram illustrating an exemplary structure of an ultrasonic diagnosis apparatus according to a second embodiment of the present invention.

FIG. 12 is a block diagram illustrating an exemplary structure of an ultrasonic diagnosis apparatus according to the second embodiment of the present invention. In an ultrasonic diagnosis apparatus 21, an image processing device 22 is arranged in place of the image processing device 13. The image processing device 22 includes a controlling unit 23 in place of the controlling unit 16, and further includes a communication circuit 24. The communication circuit 24 is electrically connected to the controlling unit 23, and further communicatively connected to a three-dimensional MRI apparatus 25 and an X-ray three-dimensional helical CT apparatus 26 via a network 27. In other respects, the structure of the second embodiment is the same as the structure of the first embodiment, and the same elements are denoted by the same reference characters.

The controlling unit 23 has the same structure and function as those of the controlling unit 16 described above. The controlling unit 23 functions so as to control the communication circuit 24, and to perform an information communication process with the three-dimensional MRI apparatus 25, or the X-ray three-dimensional helical CT apparatus 26 via the network 27. When the operator performs an input manipulation to input obtainment command information to command to obtain anatomical image data and to input selection command information to command to select a sender of the anatomical image information using the input device 11, the controlling unit 23 detects the input obtainment command information and the selection command information, and performs the information communication process based on the detected obtainment command information and the selection command information, and obtains the anatomical image data from one of the three-dimensional MRI apparatus 25 and the X-ray three-dimensional helical CT apparatus 26 through the communication circuit 24 and the network 27. When the controlling unit 23 obtains the anatomical image data from the three-dimensional MRI apparatus 25, the anatomical image data is obtained in a form of three-dimensional volume data, whereas when the controlling unit 23 obtains the anatomical image data from the X-ray three-dimensional helical CT apparatus 26, the anatomical image data is obtained in a form of a two-dimensional CT image data group which includes plural pieces of two-dimensional CT image data.

Here, the volume data is a collection of voxels. Voxel is a unit of data identified based on monochrome or color luminance or the like. The volume data corresponds to an intra-subject image data over entire three-dimensional region of the subject, or another subject. The two-dimensional CT image data group is a group of pieces of two-dimensional sectional image data of the subject or another subject and the data pieces in the group are arranged in substantially the same manner as the arrangement of the above described slice image data group.

The communication circuit 24 is implemented with a high-capacity, high-speed communication modem or the like. The communication circuit 24 receives the volume data from the three-dimensional MRI apparatus 25 through the network 27 which performs a predetermined optical communication or a high-speed telephone communication and transmits the received volume data to the controlling unit 23 under the control of the controlling unit 23, or the communication circuit 24 receives the two-dimensional CT image data group from the X-ray three-dimensional helical CT apparatus 26 and transmits the received two-dimensional CT image data group to the controlling unit 23 under the control of the controlling unit 24.

On receiving the two-dimensional CT image data group from the communication circuit 24, the controlling unit 23 associates the received two-dimensional CT image data group with the orthogonal coordinate system x'y'z', in substantially the same manner as the association of the above described slice image data group with the orthogonal coordinate system x'y'z', and stores the associated two-dimensional CT image data group in the image storing unit 14. Subsequently, the controlling unit 23 performs the processing procedure from step S101 to step S110 using the two-dimensional CT image data group instead of the above described slice image data group. Here, the controlling unit 23, using the two-dimensional CT image data group in place of the above described slice image data group, performs the processing procedure of steps S201 to S206 to set the above described feature points, and performs the processing procedure of steps S401 to S403 to create the above described guide image data.

On the other hand, on receiving the volume data from the communication circuit 24, the controlling unit 23 sets the orthogonal coordinate system x'y'z', so that a predetermined position of the volume data, e.g., a corner of a frame representing an outer rim of the volume data coincides with the origin O', and stores the volume data with which the orthogonal coordinate system x'y'z' is associated in the image storing unit 14. Then, the controlling unit 23 performs the processing procedure of steps S101 to S110 as described above using the volume data in place of the above described slice image data group.

Figure 13:
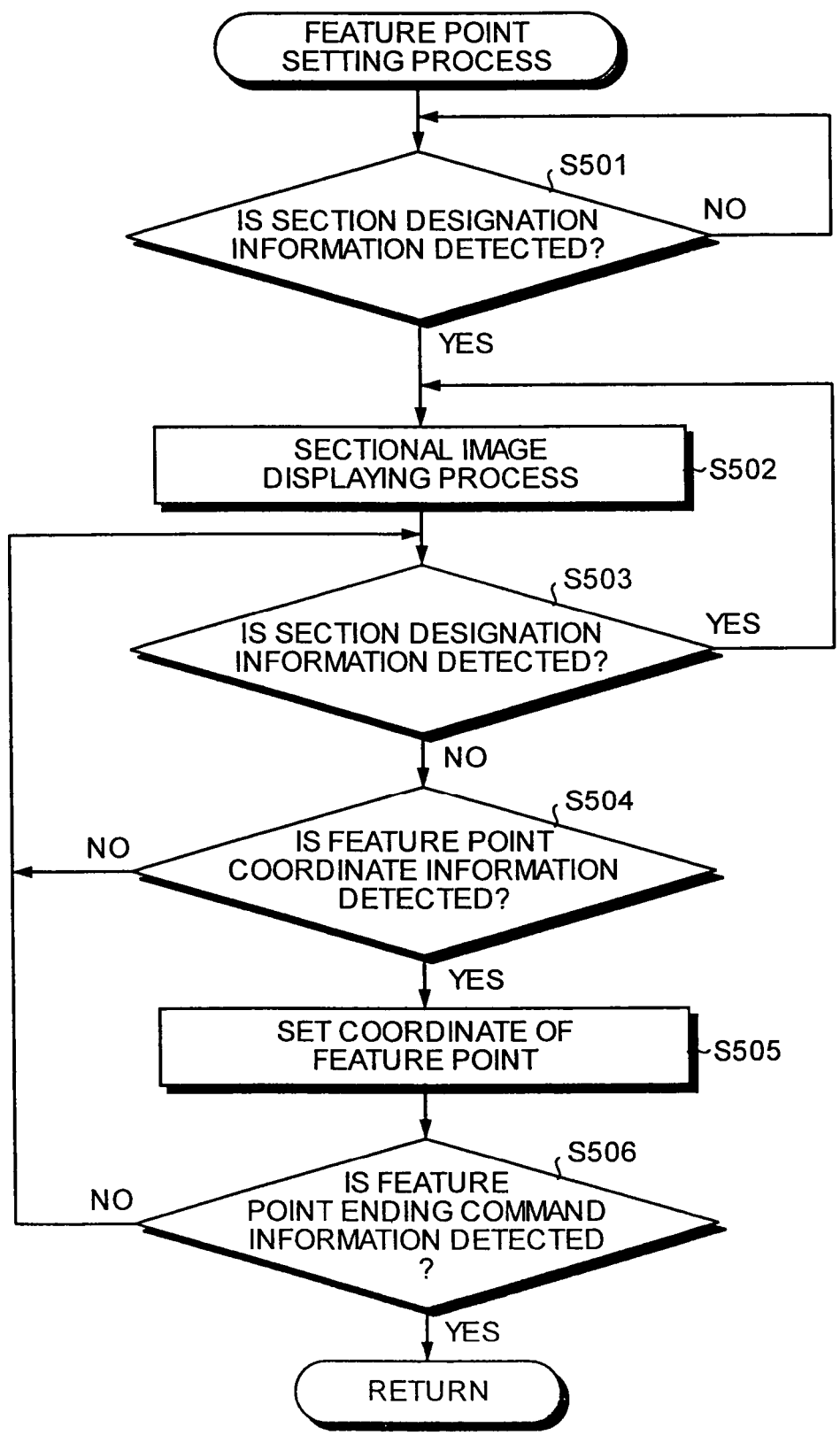
FIG. 13 is a flowchart illustrating a processing procedure up to a completion of a feature point setting process with volume data.
Figure 14:
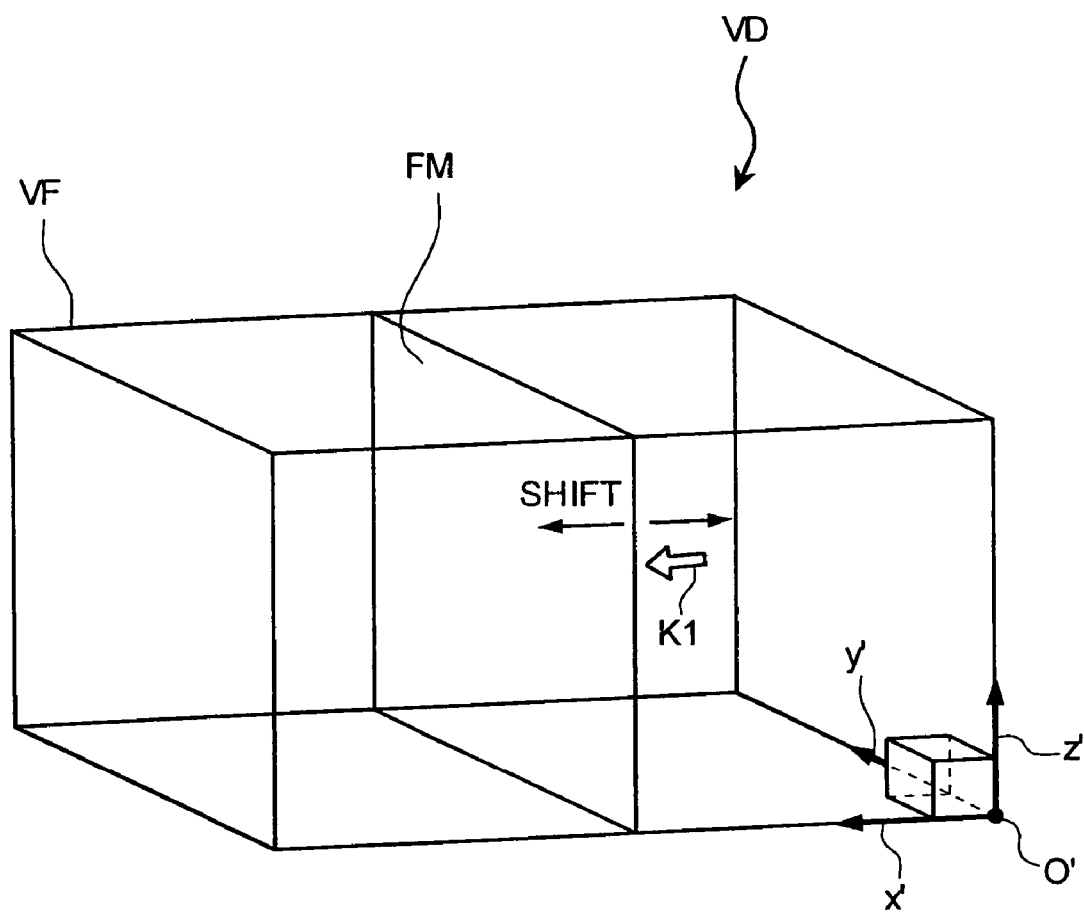
FIG. 14 is a schematic diagram illustrating an operation of setting a section of the volume data.

FIG. 13 is a flowchart illustrating a processing procedure up to a completion of feature point setting as described above with the volume data by the controlling unit 23. FIG. 14 is a schematic diagram illustrating an operation performed by the controlling unit 23 to set a section of the volume data. In FIGS. 13 and 14, volume data VD has a frame VF corresponding to an outer rim thereof and an image information plane marker FM which corresponds to a sectional position of the volume data VD and shifts in parallel within the volume data VD. Further, on the volume data VD, the orthogonal coordinate system x'y'z' is set so that a predetermined corner of the frame VF coincides with the origin O', as described above. The controlling unit 23, based on the command information input from the input device 11, outputs and displays the volume data VD on the display unit 12. In this state, the controlling unit 23 performs the feature point setting process shown in FIG. 13 using the volume data VD instead of the process of steps S201 to S206.

Specifically, when the operator performs an input manipulation to input section designation information to designate a section of the volume data VD using the input device 11, the controlling unit 23 detects the input section designation information (Yes in Step S501). Then, the controlling unit 23 performs a sectional image displaying process in which the controlling unit 23 sets a section of the volume data VD based on the detected section designation information, reads out sectional image data of the volume data VD corresponding to the set section from the image storing unit 14, and outputs and displays a section image corresponding to the read sectional image data on the display device 12 (step S502).

Here, the operator can achieve the input manipulation of the section designation information to notify the controlling unit 23 of a position which is designated as a position of the image information plane marker FM by moving a cursor K1 displayed on the display device 12 as shown in FIG. 14, for example, to a desired position within the volume data VD by manipulating the input device 11. The controlling unit 23 sets a section whose position and orientation coincide with those of the image information plane marker FM as designated by the section designation information as the section of the volume data VD. Then, the controlling unit 23 reads out the sectional image data of the volume data VD corresponding to the set section from the image storing unit 14, and transmits the read sectional image data to the display circuit 15. The display circuit 15 outputs image signals corresponding to the received sectional image data to the display device 12 substantially similarly to the processing of the slice image data described above. Thus, the controlling unit 23 achieves the sectional image displaying process using the sectional image data, and outputs and displays the volume data VD and the sectional image together in an aligned manner on the same screen of the display device 12. On the other hand, when the operator does not perform the input manipulation of the section designation information, the controlling unit 23 does not detect the section designation information (No in step S501), and repeats the processing procedure of step S501.

If the operator performs an input manipulation of the section designation information using the input device 11 while the sectional image is output and displayed on the display device 12, the controlling unit 23 detects the input section designation information (Yes in step S503), and repeats the processing procedure from step S502 described above. Then, the controlling unit 23 sequentially reads out the sectional image data of the volume data VD from the image storing unit 14 for each piece of the detected section designation information based on the section designation information detected in step S503, sequentially transmits the read sectional image data to the display circuit 15, and sequentially updates, outputs and displays the sectional image of each piece of the sectional image data on the display device 12. Thus, with repetitive execution of the processing procedure from step S501 to S503 described above by the controlling unit 23, the operator can find an anatomically characteristic region, such as ensiform cartilage, right end of pelvis, pylorus, and duodenal papilla in a similar manner as with the processing with the slice image data described above.

When the operator finds an anatomically characteristic region on the sectional image output and displayed, the operator performs an input manipulation of feature point coordinate information related with a feature point using the input device 11 in order to designate the feature point on the region. Here, the controlling unit 23 does not detect the section designation information (No in step S503), but detects the input feature point coordinate information (Yes in step S504). Then, similarly to the step S205 described above, the controlling unit 23 sets coordinate data depending on the detected feature point coordinate information as coordinate data of the feature point on the orthogonal coordinate system x'y'z' (step S505). Here, in response to the detection of the feature point coordinate information as a trigger, the controlling unit 23 is switched from a mode of setting a section of the volume data VD (section setting mode) to a mode of setting a feature point (feature point setting mode).

Thereafter, if the operator does not perform an input manipulation of the feature point ending command information, the controlling unit 23 does not detect the feature point ending command information (No in step S506), and repeats the processing procedure from step S503 described above. Thus, the operator can sequentially designate and input feature point coordinate information of each of the feature points $P_0'$ to $P_3'$ for respective points corresponding to anatomically characteristic regions, such as ensiform cartilage, right end of pelvis, pylorus, and duodenal papilla, similarly to the processing of the slice image data described above. The controlling unit 23 sequentially sets the feature points $P_0'$ to $P_3'$ as the coordinate points on the orthogonal coordinate system x'y'z' each corresponding to the ensiform cartilage, right end of pelvis, pylorus, and duodenal papilla, based on the respective pieces of the feature point coordinate information that sequentially designated and input, similarly to the processing in the first embodiment described above. Thereafter, if the controlling unit 23 detects the section designation information in step S503 described above, the controlling unit 23 is switched from the feature point setting mode mentioned above to the section setting mode mentioned above in response to the detection of the section designation information as a trigger, and repeats the processing procedure from step S502 described above.

On the other hand, if the operator performs an input manipulation of the feature point ending command information using the input device 11, the controlling unit 23 detects the input feature point ending command information (Yes in step S506), and performs the processing procedure from step S102 described above using the volume data VD as necessary instead of the slice image data group SDG described above. Further, if the controlling unit 23 does not detect the feature point coordinate information in step S504 described above (No in step S504), the controlling unit 23 repeats the processing procedure from step S503 described above.

Figure 15:
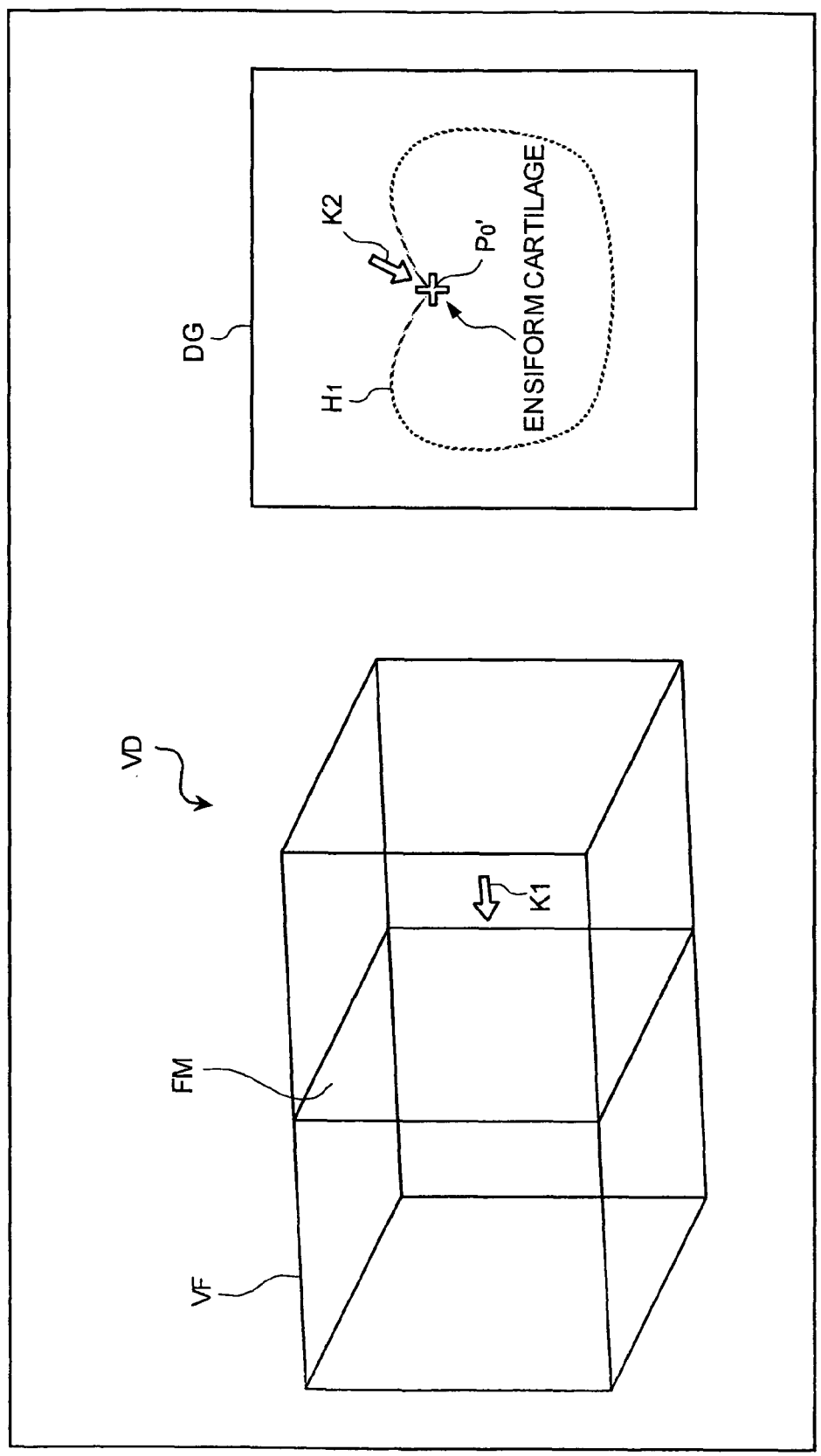
FIG. 15 is a schematic diagram illustrating an example of the volume data and a sectional image output and displayed on one screen in an aligned manner.

FIG. 15 is a schematic diagram illustrating a state where the volume data VD and the sectional image of a section corresponding to the image information plane marker FM of the volume data VD are output and displayed in an aligned manner on the same screen. As an example of the displayed sectional image, a sectional image DG of an ensiform cartilage of a costa $H_1$ is shown. The controlling unit 23 outputs and displays the volume data VD and the sectional image (for example, sectional image DG) of a section corresponding to the image information plane marker FM on the same screen of the display device 12 as described above. In other words, the controlling unit 23 outputs and displays the volume data VD which has the frame VF and the image information plane marker FM, together with the sectional image DG on the same screen of the display device 12 in an aligned manner as shown in FIG. 15. Further, the controlling unit 23 superposes the movable cursor K1 on the volume data VD in the above described section setting mode, whereas superposes a movable cursor K2 on the sectional image DG in the feature point setting mode described above as shown in FIG. 15.

The controlling unit 23 moves the cursor K1 to a position corresponding to the section designation information described above, and moves the image information plane marker FM to the position to which the cursor K1 is moved in the section setting mode. Thus, the controlling unit 23 makes the position corresponding to the section designation information and the position of the image information plane marker FM coincide with each other. Thereafter, the controlling unit 23 outputs and displays the volume data VD and the sectional image DG together as shown in FIG. 15.

Further, the controlling unit 23 moves the cursor K2 to a position corresponding to the feature point coordinate information described above and sets a feature point on the position to which the cursor K1 is moved in the feature point setting mode. Thus, the controlling unit 23 sets the feature point $P_0'$ at the position corresponding to the feature point coordinate information, e.g., at a position of the ensiform cartilage of the costa $H_1$, and superposes a marker showing the feature point $P_0'$ on the position of the feature point $P_0'$ as shown in FIG. 15.

In the second embodiment of the present invention, the two-dimensional CT image data group obtained from the X-ray three-dimensional helical CT apparatus 26 is employed as the anatomical image data similarly to the slice image data group described above for the creation of the guide image. The present invention, however, is not limited thereto. Each piece of two-dimensional CT image data in the two-dimensional CT image data group may be superposed, or an interpolating process may be performed on the pieces of two-dimensional CT image data, so that the three-dimensional CT image data is created based on the two-dimensional CT image data group. Then, the three-dimensional CT image data may be employed similarly to the volume data described above, for the setting of feature points and the creation of the guide image.

Further, in the second embodiment of the present invention, the volume data obtained from the three-dimensional MRI apparatus 25 or the two-dimensional CT image data group obtained from the X-ray three-dimensional helical CT apparatus 26 is employed as anatomical image information, and the guide image is created with a feature point set as described above. The present invention, however, is not limited thereto. A two-dimensional image data group obtained by an ultrasonic diagnosis apparatus which has the same function as the ultrasonic diagnosis apparatus of the first embodiment described above may be colored with respect to each organ in advance; the colored two-dimensional image data group may be obtained from the ultrasonic diagnosis apparatus via the network 27; and the obtained two-dimensional image data group may be employed for feature point setting and the creation of the guide image. Further, three-dimensional image data may be previously obtained via the network 27 with the use of an ultrasonic diagnosis apparatus which employs another modality such as PET (Position Emission Tomography), or an ultrasonic diagnosis apparatus which irradiates ultrasound from outside the subject body, obtained via the network, and employed for feature point setting and the creation of the guide image. Further, controlling unit 23 may color the volume data obtained from the three-dimensional MRI apparatus 25 or the two-dimensional CT image data group obtained from the X-ray three-dimensional helical CT apparatus 26 through the network 27 with respect to each organ based on luminance of the data, and store the resulting data in the image storing unit 14. Then, the stored data may be employed similarly to the slice image data group described above for the creation of the colored guide image.

As described above, in addition to the structure and the function of the first embodiment described above, the second embodiment of the present invention obtains the anatomical image data, such as the two-dimensional CT image data group or the volume data as three-dimensional image data from the outside by optical communication or high-speed telephone communication, and creates the guide image using the obtained anatomical image data. Therefore, the anatomical image data of the subject him/herself can be employed as source data for the guide image data. Thus, the advantage of the first embodiment can be enjoyed similarly in the second embodiment. In addition, since the anatomical image data of a desired area corresponding to a target interest region can be obtained, a guide image which shows more precise anatomical correspondence with the output and displayed two-dimensional ultrasound image of the subject can be created.

A third embodiment of the present invention will be described in detail below. In the first embodiment described above, the two-dimensional ultrasound image and the guide image which anatomically corresponds to the two-dimensional ultrasound image are output and displayed on the same screen in an aligned manner. In the third embodiment, at least one of the output and displayed two-dimensional ultrasound image and the guide image can be rotated.

Figure 16:
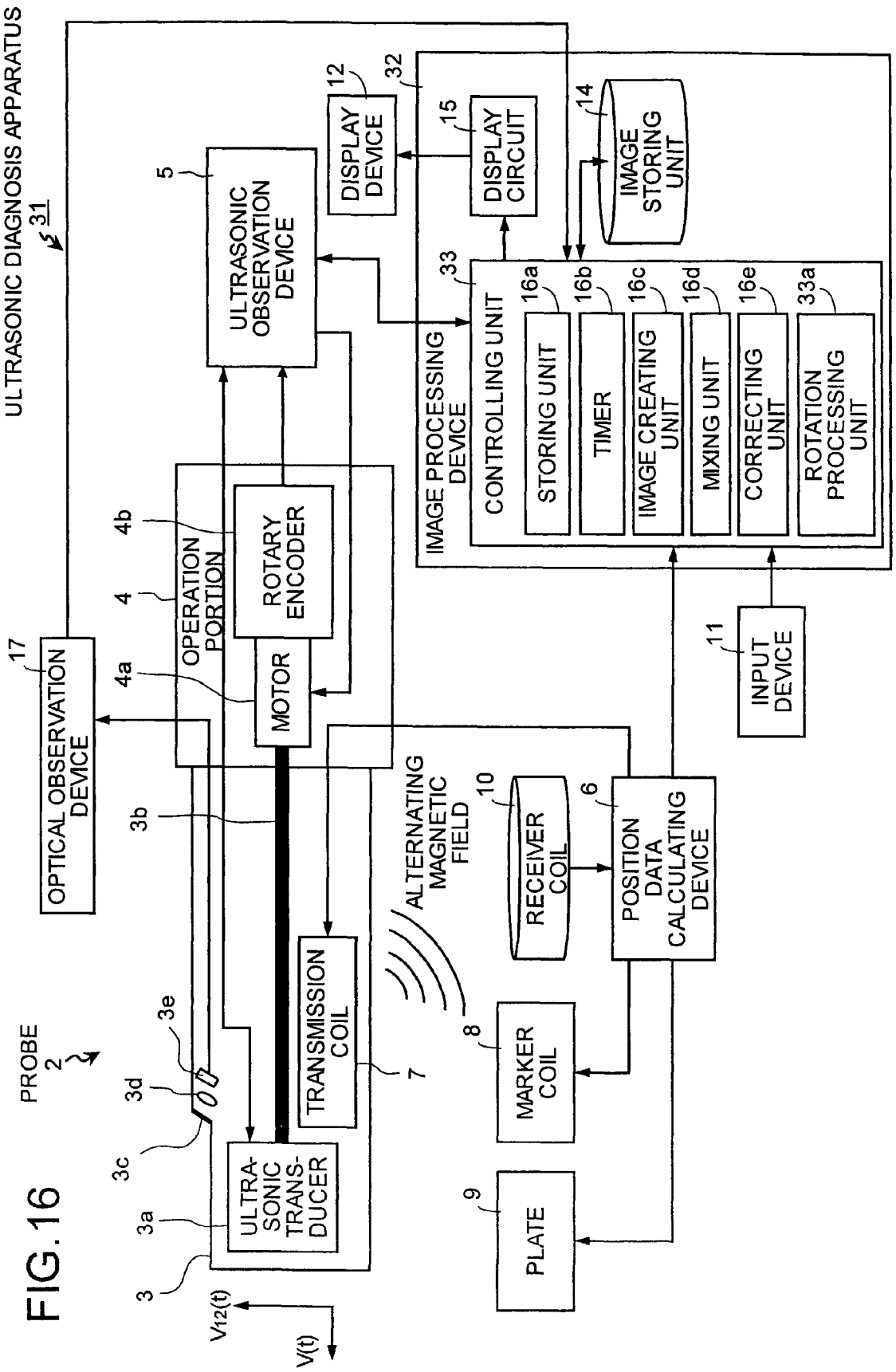
FIG. 16 is a block diagram illustrating an exemplary structure of an ultrasonic diagnosis apparatus according to a third embodiment of the present invention.

FIG. 16 is a block diagram illustrating an exemplary structure of an ultrasonic diagnosis apparatus according to the third embodiment of the present invention. An ultrasonic diagnosis apparatus 31 includes an image processing device 32 in place of the image processing device 13. The image processing device 32 includes a controlling unit 33 in place of the controlling unit 16. The controlling unit 33 has the structure and the function of the controlling unit 16 described above, and further includes a rotation processing unit 33a. In other respects, the apparatus of the third embodiment is the same with the apparatus of the first embodiment, and the same elements are denoted by the same reference characters.

When the operator performs an input manipulation of mode switching command information to switch the mode to a two-dimensional image rotation mode using the input device 11, the controlling unit 33 switches the operation mode to the two-dimensional image rotation mode based on the mode switching command information input by the input manipulation. When the operation mode of the controlling unit 33 is the two-dimensional image rotation mode, the rotation processing unit 33a performs a rotation process on the two-dimensional image data of a two-dimensional ultrasound image output and displayed on the display device 12 under the control of the controlling unit 33 based on angle information input from the input device 11, and rotates each coordinate point on a two-dimensional image plane around a central position C of the two-dimensional image plane. The angle information is information concerning a rotation angle of the two-dimensional ultrasound image around the image center. After the rotation process, the controlling unit 33 sends the rotated two-dimensional image data to the display circuit 15, and the display circuit 15 sends the image signals corresponding to the two-dimensional image data to the display device 12. Thus, the controlling unit 33 can output and display the two-dimensional ultrasound image corresponding to the two-dimensional image data to-which the rotation process is performed on-the display device 12.

Here, in the rotation process, the rotation processing unit 33a rotates each coordinate point of the two-dimensional image data according to a direction and an angle based on the angle information input from the input device 11. The input device 11 supplies, in addition to the above described various types of information such as command information and coordinate information, the angle information to the controlling unit 33. For example, when the keyboard or the touch panel is employed, the operator inputs or selects a numerical value corresponding to the angle information, or the operator manipulates the key so as to move the cursor or the like displayed in a superposed manner on the two-dimensional ultrasound image on the display device 12 in a predetermined direction, thereby inputting the angle information. On the other hand, when the track ball, mouse, or the joystick is employed, the operator selects a numerical value corresponding to the angle information, or the operator performs a manipulation (drag manipulation) so as to move the cursor or the like displayed in a superposed manner on the two-dimensional ultrasound image on the display device 12 in a predetermined direction while pressing down the mouse, thereby inputting the angle information corresponding to a shift amount of the drag manipulation.

When the operator performs a drag manipulation or a key manipulation to move the cursor upward on the screen, the controlling unit 33 receives angle information for rotating the two-dimensional ultrasound image in a positive direction by an angle corresponding to an amount of shift of the cursor through the input device 11, whereas when the operator moves the cursor downward on the screen, the controlling unit 33 receives angle information for rotating the two-dimensional ultrasound image in a negative direction by an angle corresponding to an amount of shift of the cursor through the input device 11, for example. Alternatively, when the operator performs a drag manipulation or a key manipulation to move the cursor rightward on the screen, the input device 11 inputs angle information for rotating the two-dimensional ultrasound image to a positive direction by an angle corresponding to the amount of shift of the cursor to the controlling unit 33, whereas when the operator moves the cursor leftward on the screen, the input device 11 inputs angle information for rotating the two-dimensional ultrasound image in a negative direction by an angle corresponding to the amount of shift of the cursor to the controlling unit 33.

Figure 17:
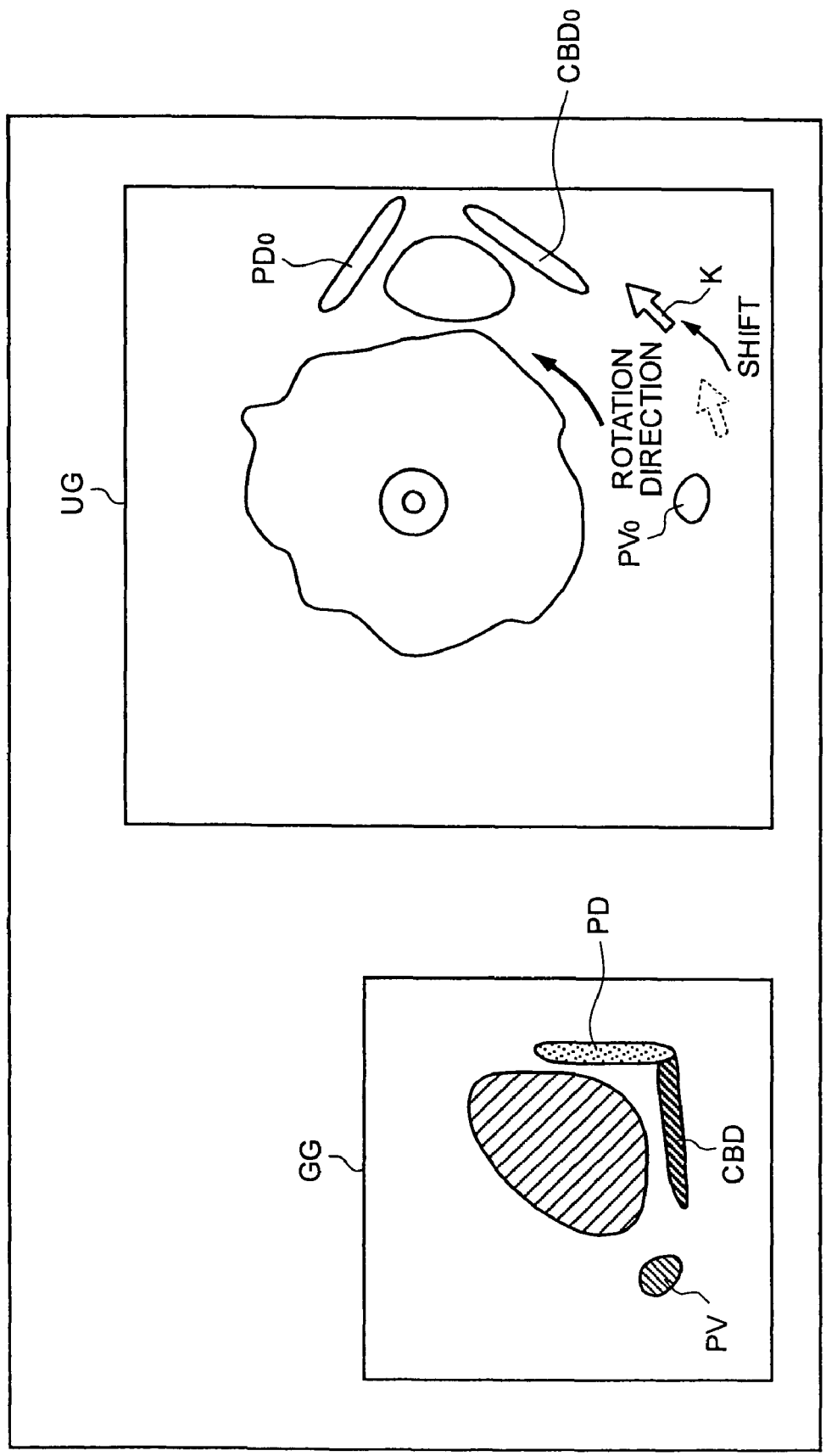
FIG. 17 is a schematic diagram illustrating an example of a guide image and a two-dimensional ultrasound image to which a rotating process is performed both output and displayed on one screen.

FIG. 17 is a schematic diagram illustrating a state in which the guide image and the two-dimensional ultrasound image after the rotation process are output and displayed on the same screen in an aligned manner. In FIG. 17, the two-dimensional ultrasound image UG described above is shown as the two-dimensional ultrasound image. Further, the guide image GG described above is shown as the guide image. Here, the two-dimensional ultrasound image UG and the guide image GG anatomically correspond with each other as described above. Further, a cursor K is superposed on the two-dimensional ultrasound image UG.

The controlling unit 33 moves the cursor K in a predetermined direction on the screen, for example, based on the angle information supplied from the input device 11 in the two-dimensional image rotating mode described above. The rotation processing unit 33a performs the rotation process to rotate each coordinate point in the two-dimensional image data of the two-dimensional ultrasound image UG in a rotation direction corresponding to the direction of shift of the cursor K by an angle corresponding to the amount of shift of the cursor K based on the angle information under the control of the controlling unit 33. The controlling unit 33 can output and display a rotated two-dimensional ultrasound image UG, which is rotated by an angle corresponding to the amount of shift of the cursor K in the rotation direction corresponding to the direction of shift of the cursor K as shown in FIG. 17, by using the two-dimensional image data to which the rotation process is performed. Thus, the controlling unit 33 can match an actual orientation of the subject as visually observed by the operator with four directions of the two-dimensional ultrasound image of the subject substantially. Such arrangement allows the operator to easily grasp the correspondence between the two-dimensional ultrasound image on the screen and the actual subject, thereby enhancing efficiency in medical diagnosis of the subject.

On the other hand, when the operator performs an input manipulation of the mode switching command information to switch to the guide image rotation mode using the input device 11, the controlling unit 33 switches the operation mode to the guide image rotation mode based on the mode switching command information input via the input manipulation. When the controlling unit 33 is in the guide image rotation mode, the rotation processing unit 33a performs the rotation process with respect to the guide image data of the guide image output and displayed on the display device 12 to rotate each coordinate point on the guide image plane around a central position C' of the guide image plane based on the angle information input from the input device 11 under the control of the controlling unit 33. Here, the angle information input in the guide image rotation mode is information concerning an angle by which the guide image is rotated around the image center. Further, the angle information in the guide image rotation mode is input to the controlling unit 33 when the operator performs an input manipulation similar to the input manipulation in the two-dimensional image rotation mode described above using the input device 11.

After the rotation process, the controlling unit 33 sends the rotated guide image data to the display circuit 15, and the display circuit 15 sends image signals corresponding to the guide image data to the display device 12. Thus, the controlling unit 33 can output and display a guide image corresponding to the guide image data after the rotation process on the display device 12.

Figure 18:
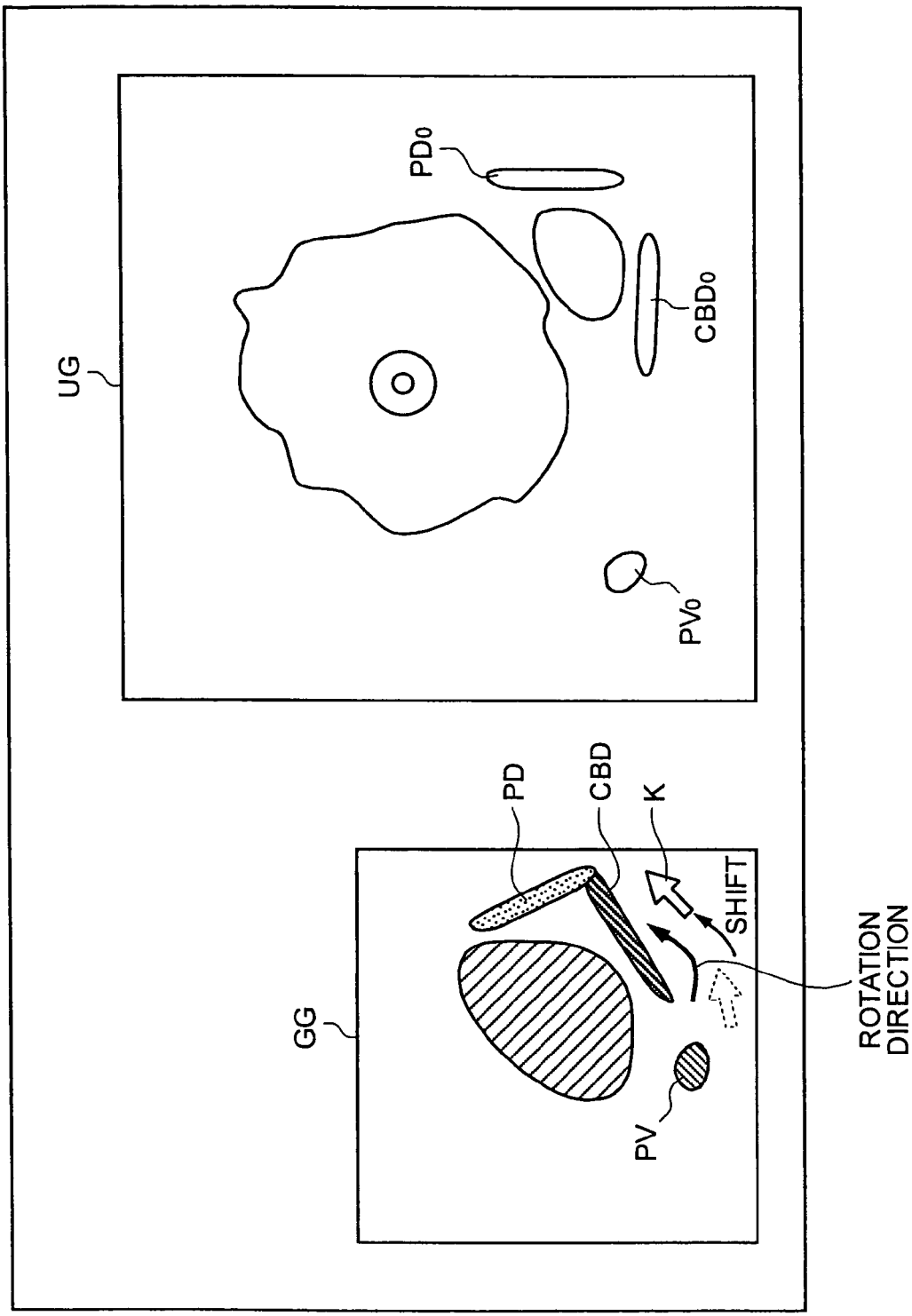
FIG. 18 is a schematic diagram illustrating an example of the two-dimensional ultrasound image and the guide image to which the rotating process is performed both output and displayed on one screen.

FIG. 18 is a schematic diagram illustrating a state in which the two-dimensional ultrasound image and the guide image to which the rotation process is performed are output and displayed on the same screen in an aligned manner. In FIG. 18, the two-dimensional ultrasound image UG is shown as the two-dimensional ultrasound image. Further, the guide image GG described above is shown as the guide image. The cursor K is superposed on the guide image GG.

In the guide image rotation mode described above, the controlling unit 33 moves the cursor K on the screen in a predetermined direction based on the angle information input from the input device 11, for example. The rotation processing unit 33a performs the rotation process so as to rotate each coordinate point on the guide image data of the guide image GG in a rotation direction corresponding to a direction of shift of the cursor K by an angle corresponding to an amount of shift of the cursor K based on the angle information under the control of the controlling unit 33. The controlling unit 33 can output and display the guide image GG which is rotated by the angle corresponding to the amount of shift of the cursor K in the rotation direction corresponding to the direction of shift of the cursor K as shown in FIG. 18 by using the guide image data after the rotation process. Thus, the controlling unit 33 can match an actual orientation of the subject as visually observed by the operator with four directions of the guide image substantially. Such arrangement allows the operator to easily grasp the correspondence between the guide image on the screen and the actual subject.

On the other hand, when the operator performs an input manipulation of the mode switching command information to switch to a tied image rotation mode using the input device 11, the controlling unit 33 switches the operation mode to the tied image rotation mode based on the mode switching command information input by the input manipulation. When the controlling unit 33 is in the tied image rotation mode as the operation mode, the rotation processing unit 33a performs a rotation process with respect to the two-dimensional image data of the two-dimensional ultrasound image output and displayed on the display device 12 so as to rotate each coordinate point on the two-dimensional image plane around the central position C of the two-dimensional image plane based on the angle information input from the input device 11 under the control of the controlling unit 33, at the same time, the rotation processing unit 33a performs the rotation process with respect to the guide image data of the guide image output and displayed on the display device 12 so as to rotate each coordinate point on the guide image plane around the central position C' of the guide image plane based on the angle information input from the input device 11 under the control of the controlling unit 33.

Here, the angle information supplied in the tied image rotation mode is information concerning an angle of rotation around the image center of the two-dimensional ultrasound image, and also is information concerning an angle of rotation around the image center of the guide image. The angle information of the tied image rotation mode is input to the controlling unit 33 when the operator performs an input manipulation using the input device 11, similarly to the manipulation in the two-dimensional image rotation mode or the guide image rotation mode described above.

Thereafter, the controlling unit 33 sends the two-dimensional image data and the guide image data both subjected to the rotation process to the display circuit 15, and the display circuit 15 sends image signals corresponding to the two-dimensional image data and the guide image data to the display device 12. Thus, the controlling unit 33 can simultaneously output and display the two-dimensional ultrasound image corresponding to the two-dimensional image data to which the rotation process is performed and the guide image corresponding to the guide image data to which the rotation process is performed on the display device 12.

Figure 19:
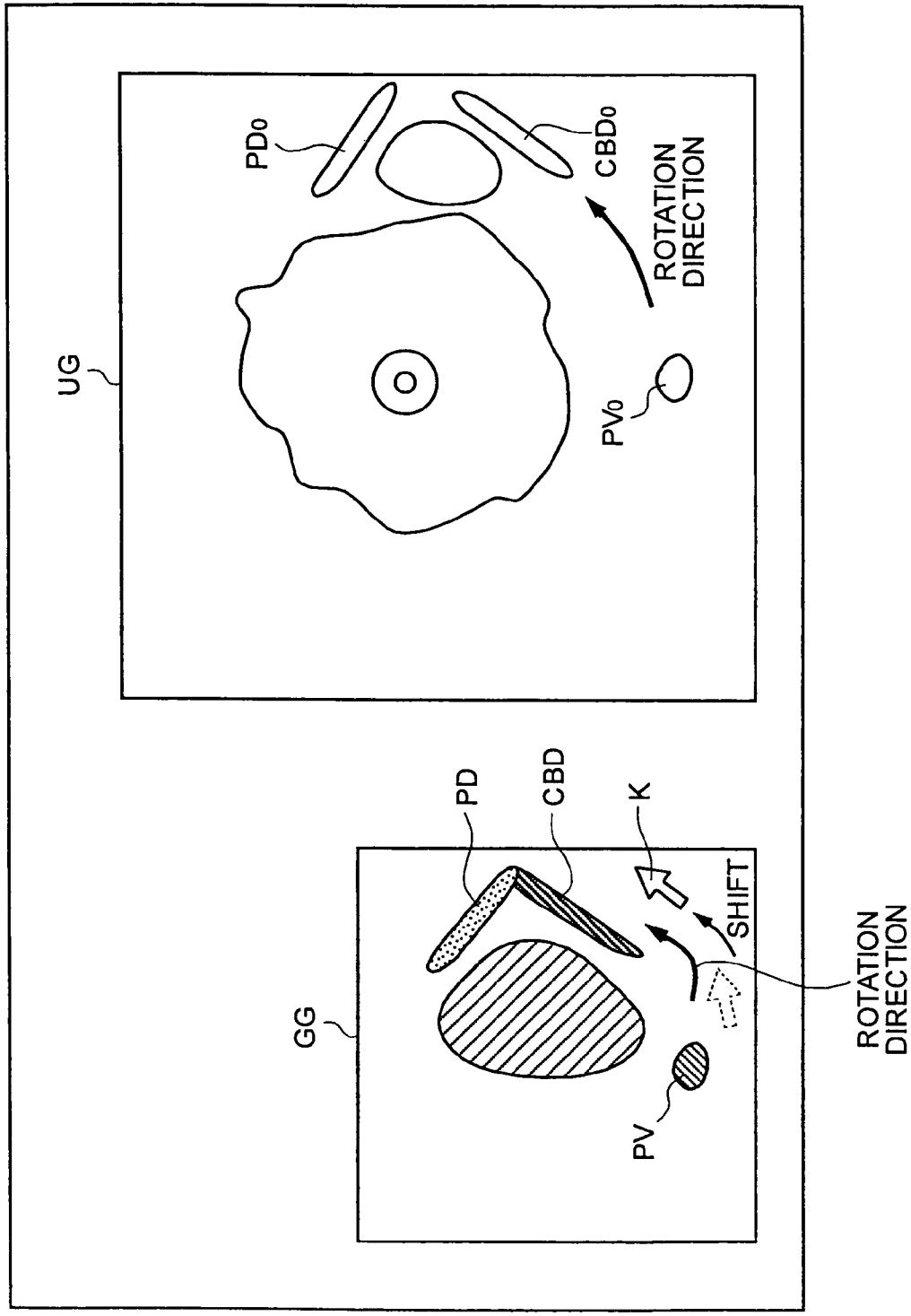
FIG. 19 is a schematic diagram illustrating an example of the two-dimensional ultrasound image to which the rotating process is performed and the guide image to which the rotating process is performed, both output and displayed on one screen.

FIG. 19 is a schematic diagram illustrating a state in which the two-dimensional ultrasound image to which the rotation process is performed and the guide image to which the rotation process is performed are output and displayed on the same screen in an aligned manner. In FIG. 19, the two-dimensional ultrasound image UG described above is shown as the two-dimensional ultrasound image, and the guide image GG described above is shown as the guide image. Further in FIG. 19, an exemplary operation is shown in which the cursor K is superposed on the guide image GG, and moves according to the input manipulation of the angle information by the operator, and the two dimensional ultrasound image UG is rotated together with the guide image GG. The present invention, however, is not limited thereto. For example, the cursor K may be superposed on the two-dimensional ultrasound UG, and moves according to the input manipulation of the angle information by the operator, and the guide image GG is rotated together with the two-dimensional ultrasound image UG.

In the above described tied image rotation mode, the controlling unit 33 moves the cursor K on the screen in a predetermined direction, for example, based on the angle information supplied from the input device 11. The rotation processing unit 33a performs the rotation process on each coordinate point on the guide image data of the guide image GG in a rotation direction corresponding to a direction of shift of the cursor K by an angle corresponding to an amount of shift of the cursor K based on the angle information under the control of the controlling unit 33, for example. At the same time, the rotation processing unit 33a performs the rotation process on each coordinate point of the two-dimensional image data of the two-dimensional ultrasound image UG in the same rotation direction as the rotation direction of each coordinate point of the guide image data by the same angle as the angle by which each coordinate point of the guide image data is rotated based on the angle information under the control of the controlling unit 33.

By using the guide image data and the two-dimensional image data both subjected to the rotation process, the controlling unit 33, as shown in FIG. 17, can output and display the guide image GG which is rotated by an angle corresponding to the amount of shift of the cursor K in the rotation direction corresponding to the direction of shift of the cursor K and the two-dimensional ultrasound image UG which is rotated by the same angle in the same rotation direction as the guide image GG. Thus, the controlling unit 33 can match an actual orientation of the subject as visually observed by the operator with four directions of each of the two-dimensional ultrasound image of the subject and the guide image substantially. Such arrangement allows the operator to easily grasp the correspondence between the two-dimensional ultrasound image on the screen and the actual subject, and at the same time allows the operator to easily grasp the correspondence between the guide image on the screen and the actual subject. Thus, an interest region such as pathological lesions inside the subject can be readily observed, and efficiency in medical diagnosis of the subject can be enhanced.

In the third embodiment of the present invention, the input manipulation, such as the drag manipulation, the key manipulation, and the selection manipulation to input or select a numerical value corresponding to an angle and a rotation direction, is performed to input angle information with the use of the input device 11, and thereby information is input concerning an angle by which each coordinate point is to be rotated and a rotation direction in which each coordinate point is to be rotated concerning at least one of the two-dimensional image data and the guide image data. The present invention, however, is not limited thereto. Alternatively, an unit angle and a rotation direction to rotate each coordinate point of at least one of the two-dimensional image data and the guide image data may be input, and each coordinate point of at least one of the two-dimensional image data and the guide image data may be sequentially rotated by the unit angle in the rotation direction, every time the command information to command the rotation of the two-dimensional ultrasound image or the guide image is input.

As described above, in addition to the structure and the function of the first embodiment described above, the third embodiment of the present invention performs the rotation process on each coordinate point of at least one of the two-dimensional image data corresponding to the two-dimensional ultrasound image and the guide image data corresponding to the guide image, based on the angle information corresponding to the rotation direction and the angle of at least one of the two-dimensional ultrasound image and the guide image; and outputs and displays the two-dimensional ultrasound image to which the rotation process is performed and the guide image to which the rotation process is performed, or alternatively outputs and displays the two-dimensional ultrasound image and the guide image to both of which the rotation process is performed by the same angle in the same direction. Thus, an actual orientation of the subject as visually observed by the operator matches with four directions of at least one of the two-dimensional ultrasound image of the subject and the guide image substantially. Such arrangement allows the operator to easily grasp at least one of the correspondence between the two-dimensional ultrasound image on the screen and the actual subject and the correspondence between the guide image on the screen and the actual subject. Thus, in addition to the enjoyment of the effect and advantage of the first embodiment described above, the third embodiment can realize the ultrasonic diagnosis apparatus which facilitates the observation of an interest region such as pathological lesions inside the subject body and enhances efficiency in medical diagnosis of the subject.

When employing the ultrasonic diagnosis apparatus, even when the direction of twelve o'clock of the ultrasonic transducer comes to be angularly misaligned with the direction of twelve o'clock detected by the ultrasonic observation device due to contortion of a shaft which flexibly connects the ultrasonic transducer and the motor, the operator can perform an observation by adjusting at least one of the two-dimensional ultrasound image and the guide image to a proper orientation in accordance with the posture of the subject. For example, when the subject under examination takes a certain posture in which the right end of pelvis comes to an upper position, the operator can rotate at least one of the two-dimensional ultrasound image and the guide image so that the right end of pelvis is located in an upper portion of the image, thereby visually matching an orientation of at least one of the two-dimensional ultrasound image and the guide image with the actual orientation of the subject.

A fourth embodiment of the present invention will be described in detail below. In the third embodiment described above, the position data concerning the two-dimensional image plane of the two-dimensional image data is detected based on the alternating magnetic field from the transmission coil 7 including the first and the second coils. In the fourth embodiment, position data concerning a direction of rotation axis and a position of rotation center of the ultrasonic transducer 3a is detected based on the alternating magnetic field from the transmission coil. The two-dimensional image plane and the guide image plane are initially set based on the detected position data and default position data previously set.

Figure 20:
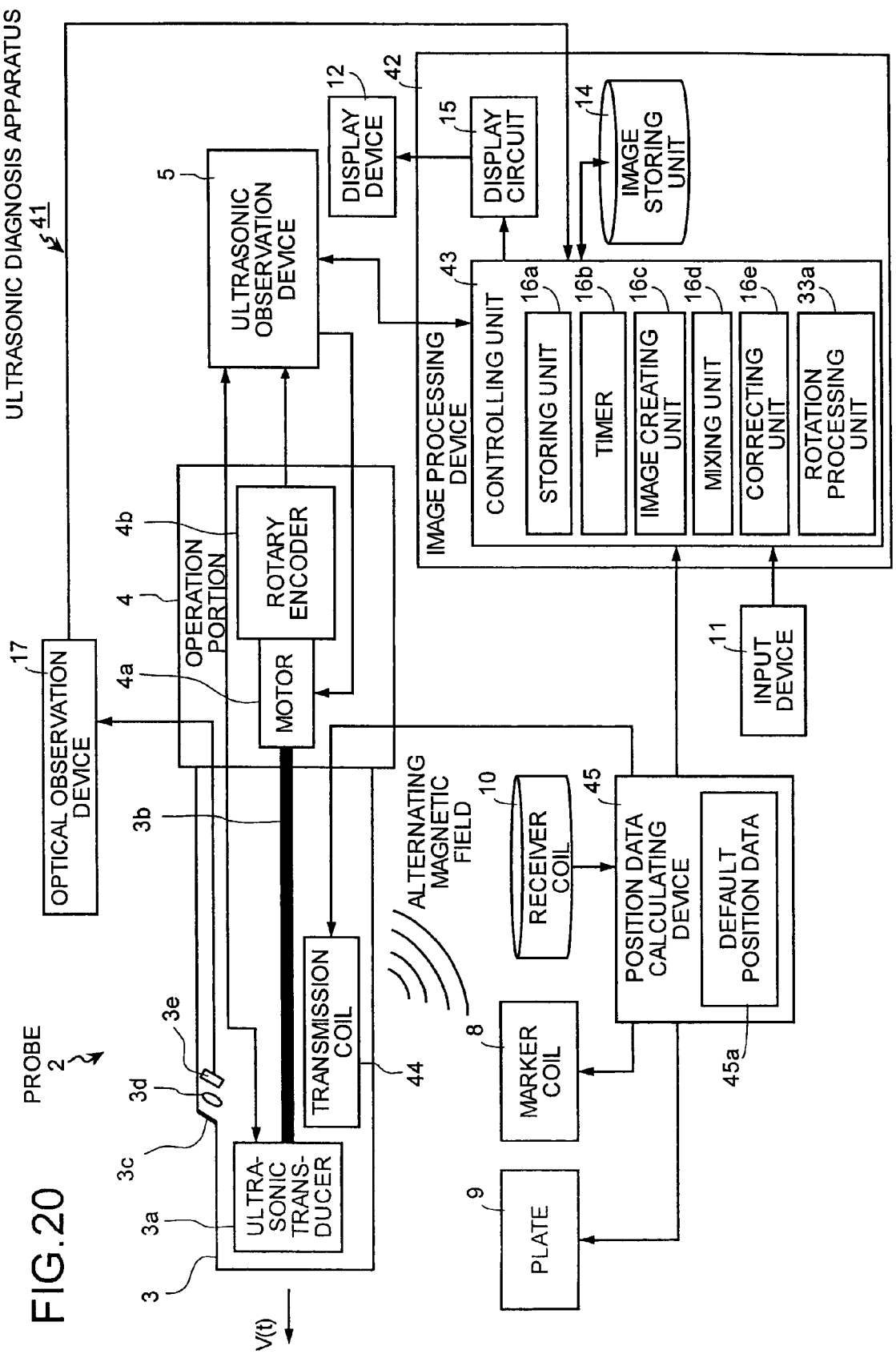
FIG. 20 is a block diagram illustrating an exemplary structure of an ultrasonic diagnosis apparatus according to a fourth embodiment of the present invention.

FIG. 20 is a block diagram illustrating an exemplary structure of an ultrasonic diagnosis apparatus according to the fourth embodiment of the present invention. The ultrasonic diagnosis apparatus 31 includes an image processing device 42 in place of the image processing device 32, includes a transmission coil 44 in place of the transmission coil 7, and includes a position data calculating device 45 in place of the position data calculating device 6. The image processing device 42 includes a controlling unit 43 in place of the controlling unit 33. The controlling unit 43 has substantially the same structure and function as those of the controlling unit 33 described above. In other respects, the fourth embodiment is the same as the third embodiment, and the same elements are denoted by the same reference characters.

The transmission coil 44 is implemented with a first coil whose coil axis is fixed in a direction of insertion axis of the insertion portion 3 to the interior of the subject, i.e., in a direction of rotation axis of the ultrasonic transducer 3a. The transmission coil 44 is detachably arranged near the ultrasonic transducer 3a substantially in the same manner as the arrangement of the transmission coil 7 described above. Further, the transmission coil 44 generates an alternating magnetic field indicating a position and a direction of rotation axis of the ultrasonic transducer 3a driven by electric currents supplied to the first coil from the position data calculating device 45.

The position data calculating device 45 has substantially the same structure and the function as those of the position data calculating device 6 described above. Default position data 45a is previously set in the position data calculating device 45. The default position data 45a is vector data which is previously set on the orthogonal coordinate system xyz as default position data to indicate an initial direction of twelve o'clock in the above described two-dimensional image plane. The position data calculating device 45 receives position detection signals from the receiver coil 10. The position detection signals are based on the alternating magnetic field from the transmission coil 44. The position data calculating device 45 further calculates position data corresponding to the center of rotation and the direction of rotation axis of the ultrasonic transducer 3a based on the received position detection signals. Thereafter, the position data calculating device 45 transmits the calculated position data and the default position data 45a to the controlling unit 43.

The controlling unit 43 performs the processing procedure of step S101 to step S110 described above, and outputs and displays the two-dimensional ultrasound image (default two-dimensional ultrasound image) and the guide image (default guide image) on the display device 12 based on the calculated position data and the default position data 45a. Here, the image creating unit 16c associates the two-dimensional image data obtained from the ultrasonic observation apparatus 5 with the position data and the default position data received from the position data calculating device 45 at the same timing under the control of the controlling unit 43. Specifically, the image creating unit 16c sets a central position C(t) and a direction vector V(t) based on the position data and a direction vector $V_{12}(t)$ based on the default position data as information that determines the position and the orientation of the two-dimensional image data. Based on the above setting, the controlling unit 43 obtains two-dimensional image data (default two-dimensional image data) having the central position C(t) and the direction vector V(t) based on the position data and the direction vector $V_{12}(t)$ based on the default position data 45a, and guide image data (default guide image data) having a central position C'(t) and a direction vector V'(t) based on the position data and a direction vector $V_{12}'(t)$ based on the default position data 45a.

Here, when the mode switching command information described above is supplied from the input device 11, the controlling unit 43 switches the operation mode to the two-dimensional image rotation mode or the guide image rotation mode as described above based on the input mode switching command information. When the controlling unit 43 is in the two-dimensional image rotation mode or the guide image rotation mode, the rotation processing unit 33a performs the rotation process on each coordinate point on the two-dimensional image plane of the default two-dimensional image data or each coordinate point on the guide image plane of the default guide image data based on the angle information input from the input device 11 similarly to the third embodiment described above. Thereafter, the controlling unit 43, similarly to the third embodiment described above, updates and displays the two-dimensional ultrasound image which is obtained by rotating the default two-dimensional ultrasound image according to the rotation process or the guide image which is obtained by rotating the default guide image according to the rotation process on the display device 12.

Further, when command information (update command information) is input from the input device 11 concerning the updating of the position data, the controlling unit 43 updates the direction vector in the direction of twelve o'clock (twelve o'clock direction vector) of the default two-dimensional image data with the twelve o'clock direction vector of the two-dimensional image data obtained through the rotation process based on the input update command information. Alternatively, the controlling unit 43 updates the twelve o'clock direction vector of the default guide image data with a twelve o'clock direction vector of the guide image data obtained through the rotation process based on the update command information.

Thereafter, the image creating unit 16c associates sequentially obtained two-dimensional image data with the updated twelve o'clock direction vector, and the central position and a direction vector in a direction of normal line (normal vector) based on the above described position data under the control of the controlling unit 43. Further, the image creating unit 16c creates the guide image data using the updated twelve o'clock direction vector, and the central position and the normal vector based on the position data described above under the control of the controlling unit 43. Alternatively, the image creating unit 16c may convert the twelve o'clock direction vector of the updated guide image data into a twelve o'clock direction vector on the orthogonal coordinate system xyz, and associate the obtained twelve o'clock direction vector, and the central position and the normal vector based on the position data described above with the sequentially obtained two-dimensional image data under the control of the controlling unit 43.

As described above, in addition to the function of the above described third embodiment, the fourth embodiment of the present invention detects the position data concerning the central position and the direction of normal line in the two-dimensional image data using the coil whose coil axis is oriented towards the direction of rotation axis of the ultrasonic transducer 3a; outputs and displays the default two-dimensional ultrasound image and the default guide image using the detected position data and the previously set default position data concerning the direction of twelve o'clock; and performs the rotation process of each coordinate point of the default two-dimensional ultrasound image or the default guide image to update the direction of twelve o'clock of the default position data. Therefore, the insertion portion to be inserted inside the subject body can be made thinner and the two-dimensional ultrasound image of the subject and the guide image which anatomically corresponds to the two-dimensional ultrasound image can be output and displayed on the same screen. Thus, in addition to the enjoyment of the effect and advantages of the third embodiment described above, according to the fourth embodiment, the ultrasonic diagnosis apparatus which is suitable for an ultrasonic examination that can alleviate the pain of the subject at a time of insertion of the probe inside the subject can be realized.

A fifth embodiment of the present invention will be described in detail below. In the first to the fourth embodiments described above, the two-dimensional ultrasound image corresponding to the two-dimensional image data and the guide image anatomically corresponding to the two-dimensional ultrasound image are output and displayed every time the two-dimensional image data of the subject is obtained through the radial scan. In the fifth embodiment, identification information which identifies the obtained two-dimensional ultrasound image is stored in association with the two-dimensional image data, and the search, output and display of the two-dimensional ultrasound image is allowed based on the identification information.

Figure 21:
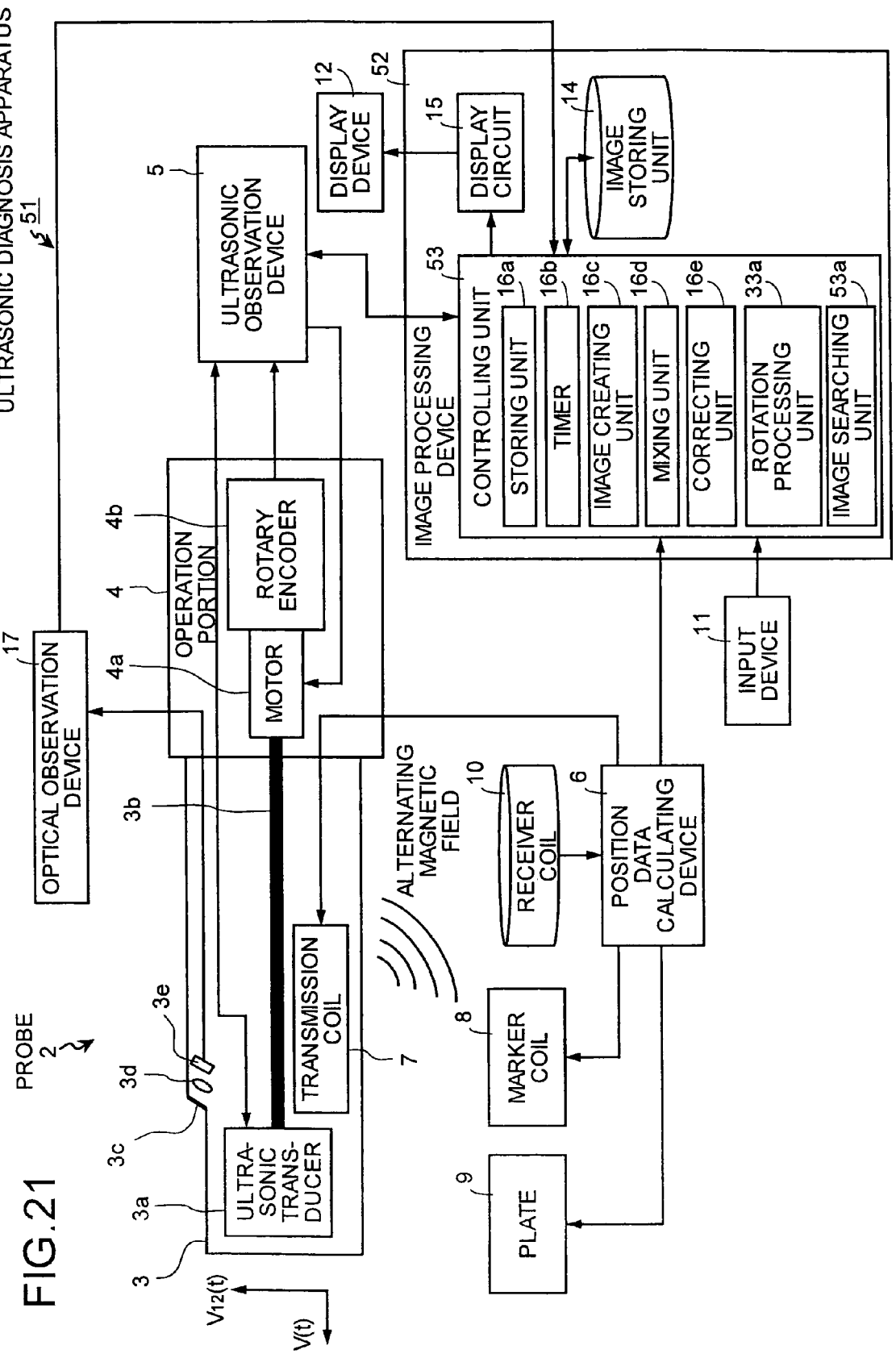
FIG. 21 is a block diagram illustrating an exemplary structure of an ultrasonic diagnosis apparatus according to a fifth embodiment of the present invention.

FIG. 21 is a block diagram illustrating an exemplary structure of an ultrasonic diagnosis apparatus according to the fifth embodiment of the present invention. An ultrasonic diagnosis apparatus 51 includes an image processing device 52 in place of the image processing device 32. The image processing device 52 includes a controlling unit 53 in place of the controlling unit 33. The controlling unit 53 has substantially the same structure and function as those of the controlling unit 33 described above. The controlling unit 53 further includes an image searching unit 53a. In other respects, the fifth embodiment is the same as the third embodiment, and the same elements are denoted by the same reference characters.

The controlling unit 53 performs the processing procedure from step S101 to step S110 described above, sequentially obtains the two-dimensional image data and creates the guide image data, each piece of which anatomically corresponds to the two-dimensional image data, and sequentially outputs and displays the two-dimensional ultrasound image each corresponding to the two-dimensional image data and the guide image each corresponding to the guide image data on the display device 12. Here, the controlling unit 53 stores the position data corresponding to the position and the orientation of the two-dimensional image data in association with each piece of the two-dimensional image data in the image storing unit 14, and stores the position data corresponding to the position and the orientation of each piece of the guide image data in association with the guide image data in the image storing unit 14.

Further, when the above described mode switching command information is input from the input device 11, the controlling unit 53 switches the operation mode to the two-dimensional image rotation mode, guide image rotation mode, or the tied image rotation mode described above based on the input mode switching command information. When the controlling unit 53 is in one of the two-dimensional image rotation mode, the guide image rotation mode, and the tied image rotation mode, the rotation processing unit 33a performs the rotation process on each coordinate point of at least one of the two-dimensional image plane of the two-dimensional image data and the guide image plane of the guide image data based on the angle information input from the input device 11 similarly to the process in the third embodiment described above. Thereafter, similarly to the third embodiment described above, the controlling unit 53 updates the two-dimensional ultrasound image to which the rotation process is performed and the guide image to which the rotation process is performed, or the two-dimensional ultrasound image and the guide image both subjected to the rotation process by the same rotation angle in the same rotation direction, and displays the updated images on the display device 12. Here, when the update command information is input from the input device 11, the controlling unit 53 updates the position data concerning the two-dimensional image data to the position data of the two-dimensional image data after the rotation process based on the input update command information, or updates the position data of the guide image data to the position data of the guide image data after the rotation process. Thereafter, the controlling unit 53 stores the updated position data of the two-dimensional image data in association with the two-dimensional image data in the image storing unit 14, or stores the updated position data of the guide image data in association with the guide image data in the image storing unit 14.

Further, when the operator inputs identification information concerning the two-dimensional ultrasound image using the input device 11, the controlling unit 53 detects the input identification information and stores the two-dimensional image data of the two-dimensional ultrasound image in association with the identification information in the image storing unit 14. Specifically, when the identification information is sequentially input from the input device 11 for each two-dimensional ultrasound image, the controlling unit 53 sequentially detects each piece of the input identification information, and stores the two-dimensional image data of the two-dimensional ultrasound image in association with each piece of the sequentially input identification information in the storing unit 16a or the image storing unit 14. Thus, the controlling unit 53 can associate the two-dimensional image data, position data thereof, the guide image data anatomically corresponds with the two-dimensional image data, and position data thereof, and identification information thereof with each of the two-dimensional ultrasound image which is designated by the identification information and for which the identification information is input. Further, when the above described rotation process is performed, the controlling unit 53 associates angle information of each rotation process performed, or the position data of each updated two-dimensional image data or each updated guide image data with each of the above described two-dimensional ultrasound image.

The identification information is information that identifies each of the two-dimensional ultrasound images output and displayed. For example, the identification information may be a name of the two-dimensional ultrasound image, an identification code, and information of a subject related with the two-dimensional ultrasound image. The controlling unit 53 may output and display the input identification information in association with each of the two-dimensional ultrasound images on the display unit 12.

Here, when the operator performs an input manipulation of the identification information which is already associated in the above described manner as information for searching a target two-dimensional ultrasound image using the input device 11, the controlling unit 53 detects the input identification information and controls the image searching unit 53a. The image searching unit 53a searches the image storing unit 14 or the storing unit 16a for the two-dimensional image data and the position data thereof, and the guide image data and the position data thereof, each associated with the above identification information using the already associated identification information input from the input device 11 under the control of the controlling unit 53. Further, when the two-dimensional image data or the guide image data that is associated with the above associated identification information has been subjected to the rotation process as described above, the image searching unit 53a further searches the image storing unit 14 or the storing unit 16a for the angle information of the rotation process or the updated position data of the two-dimensional image data or the updated position data of the guide image data.

Thereafter, the controlling unit 53 outputs and displays the two-dimensional ultrasound image and the guide image both associated with the above associated identification information on the display device 12 using various pieces of information searched by the image searching unit 53a. Here, the controlling unit 53 may control the image processing device 52 so that the two-dimensional ultrasound image found as a result of the search is output and displayed together with a current two-dimensional ultrasound image obtained by the radial scan on the same screen.

In the ultrasonic diagnosis apparatus according to the fifth embodiment of the present invention, the structure and the function of searching, outputting, and displaying the two-dimensional ultrasound image and the guide image are further added to the structure and the function of the third embodiment described above. The present invention, however, is not limited thereto. The structure and the function of searching, outputting, and displaying the two-dimensional ultrasound image and the guide image may be added to the ultrasonic diagnosis apparatus having the structure and the function of the first embodiment described above. In other words, the ultrasonic diagnosis apparatus may not have the rotation processing unit 33a. Further, the structure and the function of searching, outputting, and displaying the two-dimensional ultrasound image and the guide image may be added to the ultrasonic diagnosis apparatus having the structure and the function of the second embodiment described above. Still further, the structure and the function of searching, outputting, and displaying the two-dimensional ultrasound image and the guide image may be added to the ultrasonic diagnosis apparatus having the structure and the function of the fourth embodiment described above.

As described above, in addition to the structure and the function of one of the first to the fourth embodiments described above, the fifth embodiment stores, when the identification information for each of the two-dimensional ultrasound images is sequentially input, the two-dimensional image data and the position data thereof, the guide image data each anatomically corresponding to the two-dimensional image data and the position data thereof, and the identification information in association with each of the two-dimensional ultrasound image identified by each piece of the sequentially input identification information; further stores the angle information for each rotation process or the updated position data of each piece of the two-dimensional image data or the guide image data in association as necessary; and, if the already associated identification information is input, searches for the two-dimensional image data and the position data thereof, the guide image data and the position data thereof, and if necessary, the angle information of each rotation process or the updated position data of the two-dimensional image data or the guide image data based on the input associated identification information. Therefore, the desired two-dimensional ultrasound image and the guide image can be searched, output, and displayed based on the identification information. Thus, in addition to the enjoyment of the effects and the advantage of one of the above described first to the fourth embodiments, the ultrasonic diagnosis apparatus that facilitates an observation of the desired two-dimensional ultrasound image and the guide image, and allows for a facilitated management of the two-dimensional ultrasound images on a desired search unit basis for each subject or for each observation region can be realized.

By employing the above ultrasonic diagnosis apparatus, the operator can readily grasp which region of the subject the two-dimensional ultrasound image represents from which direction, by referring to the identification information input for the image search and comparing the identification information and the two-dimensional ultrasound image which is output and displayed as a result of the image search. Further, the operator can easily compare the two-dimensional ultrasound image displayed as a result of the image search and the current two-dimensional ultrasound image to efficiently confirm a progression of the disease, a degree of recovery, or the like.

A sixth embodiment of the present invention will be described in detail below. In the first to the fifth embodiments described above, the position data of the ultrasonic transducer 3a is calculated according to the position detection signals that are based on the alternating magnetic field from the transmission coil 7. In the sixth embodiment, the shape of the insertion portion 3 inserted inside the subject body is further detected, output, and displayed.

Figure 22:
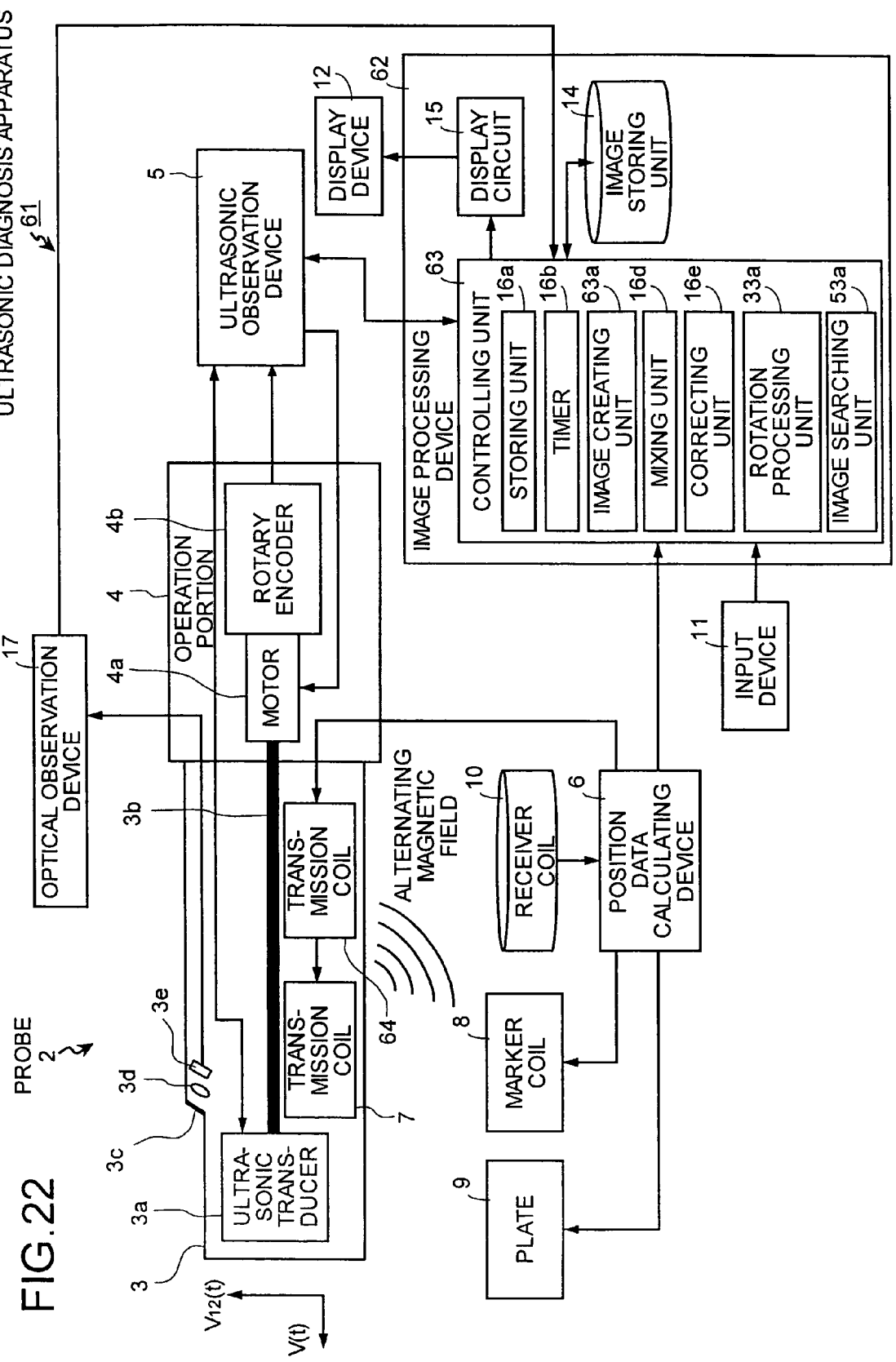
FIG. 22 is a block diagram illustrating an exemplary structure of an ultrasonic diagnosis apparatus according to a sixth embodiment of the present invention.

FIG. 22 is a block diagram illustrating an exemplary structure of an ultrasonic diagnosis apparatus according to the sixth embodiment of the present invention. An ultrasonic diagnosis apparatus 61 includes an image processing device 62 in place of the image processing device 52 in the ultrasonic diagnosis apparatus 51 described above, and further includes a transmission coil 64. The image processing device 62 includes a controlling unit 63 in place of the controlling unit 53. The controlling unit 63 has substantially the same structure and function as those of the controlling unit 53 described above, and includes an image creating unit 63a in place of the image creating unit 16c. Further, the transmission coil 64 is electrically connected to the position data calculating device 6, and electrically connected to the transmission coil 7. Hence, the position data calculating device 6 and the transmission coil 7 are electrically connected via the transmission coil 64. In other respects, the structure of the sixth embodiment is the same as the structure of the fifth embodiment, and the same elements will be denoted by the same reference characters.

The transmission coil 64 is implemented with plural coils. The transmission coil 64 is arranged on a back end side of the insertion portion 3 relative to the transmission coil 7, in other words, at a side where the operation portion 4 is arranged. Here, plural coils $W_1, W_2, \ldots, W_m$ (m is an integer number not less than two) embedded in the transmission coil 64 are sequentially arranged from a transmission coil 7 side to the back end side of the insertion portion 3 in a substantially linear manner. Thus, the plural coils $W_1, W_2, \ldots, W_m$ are arranged next to the first coil of the transmission coil 7 described above following a lengthwise shape of the insertion portion 3 in this order. Here, it is desirable that the number of the plural transmission coils $W_1, W_2, \ldots, W_m$ be ten or more (for example, approximately ten).

The transmission coil 64 outputs an alternating magnetic field with different frequency with respect to each embedded coil when the position data calculating device 6 supplies electric currents. The receiver coil 10 receives the alternating magnetic field from the transmission coil 64 as well as the alternating magnetic field from the transmission coil 7 or the like described above, and transmits position detection signals based on the received alternating magnetic field to the position data calculating device 6. The position data calculating device 6, on receiving the position detection signals from the receiver coil 10, calculates each direction component of position vectors $OU_1, OU_2, \ldots, OU_m$ of positions $U_1, U_2, \ldots, U_m$ of the plural coils $W_1, W_2, \ldots, W_m$ on the orthogonal coordinate system xyz based on the received position detection signals.

Subsequently, the position data calculating device 6 transmits the respective calculated direction components of the position vectors $OU_1, OU_2, \ldots, OU_m$ of positions $U_1, U_2, \ldots, U_m$ of the plural coils $W_1, W_2, \ldots, W_m$ to the controlling unit 63 as the position data (insertion portion position data) based on the alternating magnetic field from the transmission coil 64. In brief, the position data calculating device 6 transmits the transmission coil position data from the transmission coil 7, the marker coil position data from the marker coil 8, and the plate position data from the plate 9, to the controlling unit 63, and further transmits the insertion portion position data to the controlling unit 63.

The controlling unit 63 performs the processing procedure of steps S101 to S110 as described above, to sequentially obtain the two-dimensional image data and to create guide image data, each piece of which anatomically corresponds to the two dimensional image data, and sequentially outputs and displays the two-dimensional ultrasound images each correspond to the two-dimensional image data and the guide images each correspond to the guide image data on the display device 12. When the position data calculating device 6 inputs the insertion portion position data to the controlling unit 63, the controlling unit 63 detects the insertion portion position data, detects the time t at which the insertion portion position data is detected with the timer 16b, and controls the image creating unit 63a.

The image creating unit 63a has substantially the same structure and function as those of the image creating unit 16c described above. Further, the image creating unit 63a functions as to create inserted shape image data corresponding to an inserted shape image which indicates a shape of the insertion portion 3 inserted inside the subject body. The image creating unit 63a sets the insertion portion position data input from the position data calculating device 6, i.e., the respective direction components of the position vectors $OU_1, OU_2, \ldots, OU_m$, as coordinate data of the inserted shape image data at a time t under the control of the controlling unit 63. Here, the image creating unit 63a obtains the respective direction components of the position vectors $OU_1(t), OU_2(t), \ldots, OU_m(t)$ as the coordinate data of the inserted shape image data at the time t. Further, the image creating unit 63a obtains only the direction component of the position vector OC(t) of the central position C(t) at the time t from the transmission coil position data at the time t as the insertion portion position data at the time t under the control of the controlling unit 63.

Further, the image creating unit 63a creates the inserted shape image data based on the respective direction components of the position vectors $OU_1(t), OU_2(t), \ldots, OU_m(t)$ and the direction component of the position vector OC(t) obtained as the insertion portion position data at the time t. The image creating unit 63a can create the inserted shape image data at the time t by interpolating the coordinate points as if sequentially connecting the coordinate points based on the respective direction components of the position vectors $OU_1(t), OU_2(t), \ldots, OU_m(t)$, starting from the coordinate point based on the direction component of the position vector OC(t). The inserted shape image data at the time t corresponds to the inserted shape image which includes marks each corresponding to the coordinate points based on the position vectors obtained at time t, and an inserted shape line that represents the shape of the inserted insertion portion 3 at the time t, and that sequentially connects the marks.

The mixing unit 16d creates mixed image data based on the inserted shape image data at the time t, the two-dimensional image data obtained at the same timing, i.e., at the time t, and the guide image data at the time t anatomically corresponding to the two-dimensional image data, under the control of the controlling unit 63, to output and display an inserted shape image, a two-dimensional ultrasound image, and a guide image corresponding respectively to the inserted shape image data, the two-dimensional image data, and the guide image data that are created as plural pieces of image data of the same timing, on the same screen of the display device 12 in an aligned manner. Thereafter, the mixed image data is output to the display circuit 15 under the control of the controlling unit 63. The display circuit 15 outputs image signals corresponding to the mixed image data through conversion under the control of the controlling unit 63 as described above. The display device 12 outputs and displays the two-dimensional ultrasound image, the guide image, and the inserted shape image of the same timing corresponding to the mixed image data on the same screen in an aligned manner based on the image signals received from the display circuit 15.

Figure 23:
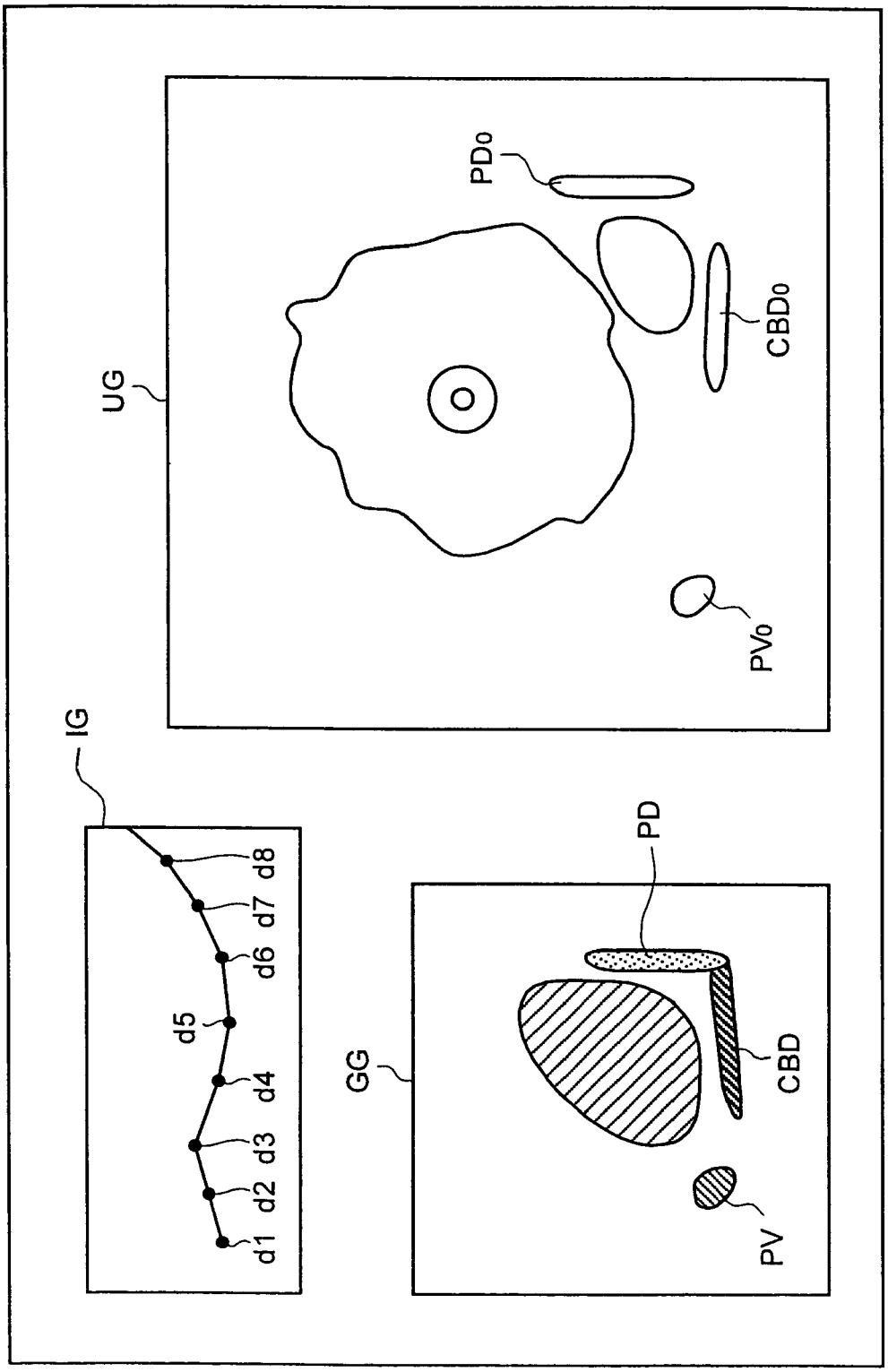
FIG. 23 is a schematic diagram illustrating an example of a display of a two-dimensional ultrasound image, a guide image, and an inserted shape image of a same timing.

FIG. 23 is a schematic diagram illustrating an example of a display where the two-dimensional ultrasound image, the guide image, and the inserted shape image obtained at the same timing are output and displayed in the same screen in an aligned manner. The controlling unit 64 can output and display the two-dimensional ultrasound image UG of time ts, the guide image GG of time ts, and the inserted shape image IG of time ts on the same screen in an aligned manner as shown in FIG. 23 by outputting the mixed image data based on the two-dimensional image data, the guide image data, and the inserted shape image data of the same timing, for example of time ts, to the display circuit 15. Here, the two-dimensional ultrasound image UG and the guide image GG anatomically correspond with each other as described above.

Further, the inserted shape image IG shows an inserted shape of the insertion portion 3 of the probe 2 which detects the two-dimensional image data corresponding to the two-dimensional ultrasound image UG, i.e., the shape of the insertion portion 3 which is inserted inside the subject at the time ts. Specifically, the inserted shape image IG shows marks d1, d2, . . . , dm (note that only marks d1 to d8 are shown in the drawing) that respectively correspond to the coordinate points that are based on the position vectors OC(ts), $OU_1$(ts), $OU_2$(ts), . . . , $OU_m$(ts) of the time ts, and the inserted shape line sequentially connecting the marks d1, d2, . . . , dm as shown in FIG. 23.

Here, the mark d1 corresponds to a coordinate point which is based on the direction component of the position vector OC(ts) at a time t the insertion portion position data is obtained, for example, at the time ts. The marks d2, d3, . . . , dm that sequentially follow the mark d1 correspond to coordinate points that are based on the direction components of the position vectors $OU_1$(ts), $OU_2$(ts), . . . , $OU_m$(ts) at the time t, for example, at the time ts, respectively. When the marks d1 to dm are shown in the inserted shape image, the mark d1 may be displayed in a different manner from the marks d2 to dm. With such manner of display, the position of the distal end of the probe can be easily found in the inserted shape image.

Further, every time the controlling unit 63 obtains the two-dimensional image data, the controlling unit 63 sequentially creates the guide image data anatomically corresponding to the obtained two-dimensional image data, respectively, and further sequentially creates the inserted shape image data based on the insertion portion position data sequentially obtained at the same timing as the timing of sequential obtainment of the two-dimensional image data. Thereafter, every time the controlling unit 63 obtains the two-dimensional image data, the controlling unit 63 sequentially updates the two-dimensional ultrasound image displayed on the display device 12 based on the sequentially obtained two-dimensional image data, and at the same time, sequentially updates the guide image displayed on the display device 12 based on the sequentially created guide image data, and at the same time, updates the inserted shape image displayed on the display device 12 based on the sequentially created inserted shape image data. In brief, when the operator looks for an interest region of the subject by repeatedly performing the radial scan described above with the ultrasonic diagnosis apparatus 61, the controlling unit 63 sequentially updates the two-dimensional ultrasound image, the guide image, and the inserted shape image, on real time, and the display device 12 displays the updated images.

The sixth embodiment of the present invention illustrates the ultrasonic diagnosis apparatus which has, in addition to the structure and the function of the fifth embodiment described above, the structure and the function to output and display the inserted shape image. The present invention, however, is not limited thereto. The structure and the function to output and display the inserted shape image may be added to the ultrasonic diagnosis apparatus which has the structure and the function of one of the third and the fourth embodiments described above. Specifically, the ultrasonic diagnosis apparatus may not have the image searching unit 53a. Further, the structure and the function to output and display the inserted shape image may be added to the ultrasonic diagnosis apparatus having the structure and the function of one of the first and the second embodiments described above. In other words, the ultrasonic diagnosis apparatus may not have the rotation processing unit 33a and the image searching unit 53a.

In the sixth embodiment of the present invention, every time the two-dimensional image data is obtained, the two-dimensional ultrasound image is sequentially updated based on the sequentially obtained two-dimensional image data, and at the same time, the guide image is sequentially updated based on the sequentially created guide image data, and at the same time, the inserted shape image is updated based on the sequentially created inserted shape image data. The present invention, however, is not limited thereto. For example, every time the distal end of the probe 2 moves by a predetermined amount, as calculated from the insertion portion position data, or every time a predetermined time elapses as detected with the timer 16b, the two-dimensional ultrasound image may be sequentially updated based on the sequentially obtained two-dimensional image data, the guide image may be sequentially updated based on the sequentially created guide image data, and the inserted shape image may be updated based on the sequentially created inserted shape image data.

As described above, in the sixth embodiment of the present invention, in addition to the structure and the function of one of the first to the fifth embodiments described above, the ultrasonic diagnosis apparatus has the structure to sequentially obtain the insertion portion position data corresponding to the inserted shape of the probe insertion portion which is inserted inside the subject body, to sequentially create the inserted shape image data which indicates the inserted shape based on each piece of the insertion portion position data obtained at the same timing as the timing of the sequential obtainment of the two-dimensional image data, to sequentially update the two-dimensional ultrasound image based on the sequentially obtained two-dimensional image data, to sequentially update the guide image based on the sequentially created guide image data, and at the same time to update the inserted shape image based on the sequentially created inserted shape image data. Therefore, the two-dimensional ultrasound image of the interior of the subject body, the guide image that anatomically corresponds to the two-dimensional ultrasound image, and the inserted shape image of the probe insertion portion that detects the two-dimensional image data of the two-dimensional ultrasound image can be output and displayed on the same screen on real time. Therefore, the operator can easily grasp the current shape of the probe insertion portion which is inserted inside the subject body. Thus, in addition to the enjoyment of the effect and advantage of one of the first to the fourth embodiments described above, the ultrasonic diagnosis apparatus which can enhance operation efficiency up to the output and the display of the two-dimensional ultrasound image of the target interest region can be realized.

By employing the above ultrasonic diagnosis apparatus, the operator can easily grasp the current shape of the probe insertion portion which is inserted inside the subject body.

Therefore, the operator can correctly and easily position the scanning plane of the probe insertion portion provided for the radial scan towards the target interest region, whereby the two-dimensional ultrasound image of the target interest region can be efficiently observed.

A seventh embodiment of the present invention will be described in detail below. In the first to the sixth embodiments as described above, the radial scan of the interior of the subject body is performed with a rotational driving of the ultrasonic transducer 3a provided near the distal end of the insertion portion 3 and a repetitive radial transmission/reception of the ultrasound. In the seventh embodiment, a group of ultrasonic transducers is provided in which plural ultrasonic transducers are arranged in a circle, so that the electric radial scan can be performed to the interior of the subject body.

Figure 24:
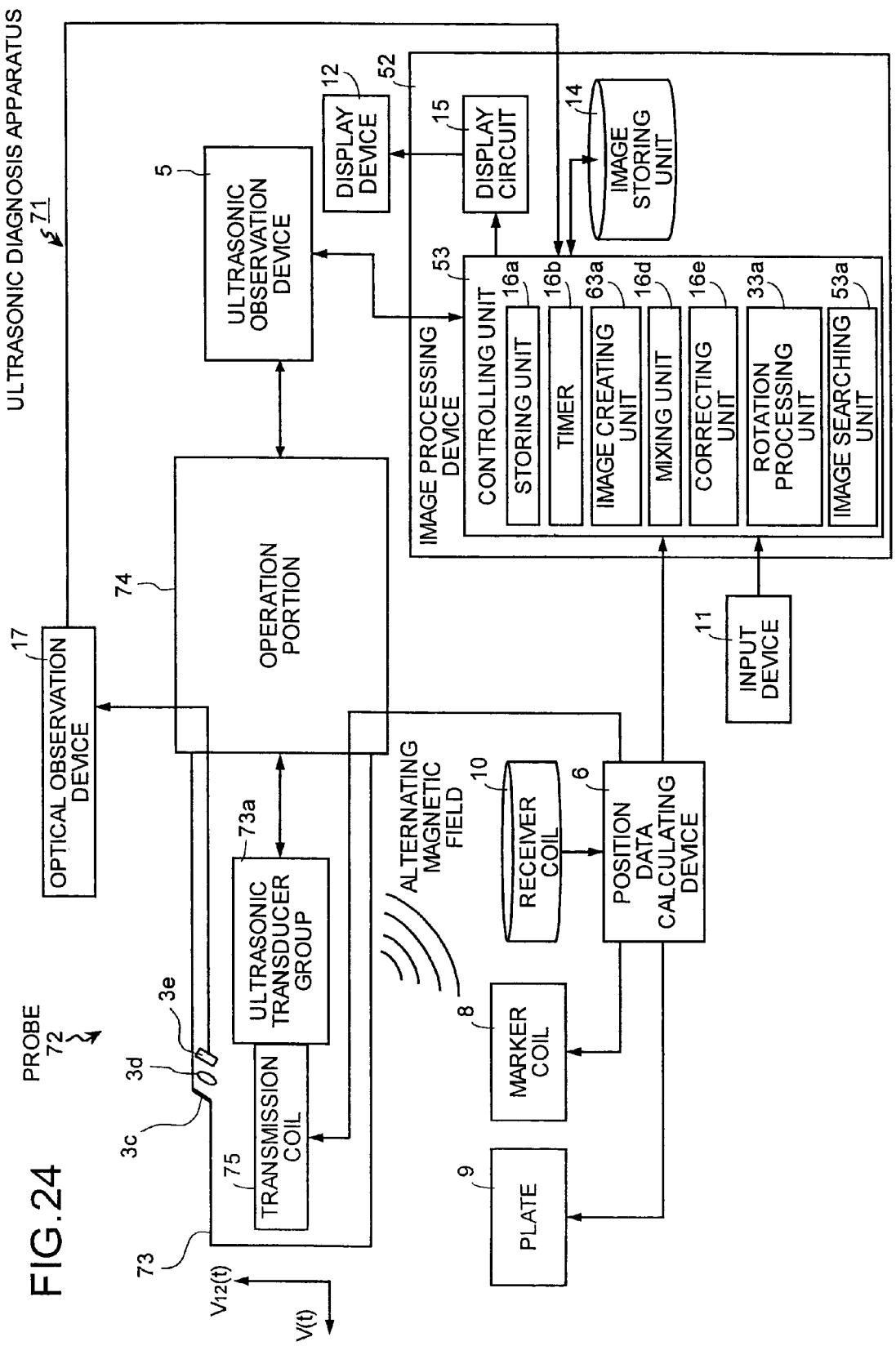
FIG. 24 is a block diagram illustrating an exemplary structure of an ultrasonic diagnosis apparatus according to a seventh embodiment of the present invention.

FIG. 24 is a block diagram illustrating an exemplary structure of an ultrasonic diagnosis apparatus according to the seventh embodiment of the present invention. An ultrasonic diagnosis apparatus 71 includes a probe 72 in place of the probe 2 of the ultrasonic diagnosis apparatus 51 described above. The probe 72 includes an insertion portion 73 in place of the insertion portion 3, an operation portion 74 in place of the operation portion 4, and a transmission coil 75 in place of the transmission coil 7. The insertion portion 73 includes an ultrasonic transducer group 73a in place of the ultrasonic transducer 3a. In other respects, the structure of the seventh embodiment is the same as the structure of the fifth embodiment, and the same elements will be denoted by the same reference characters.

Figure 25:
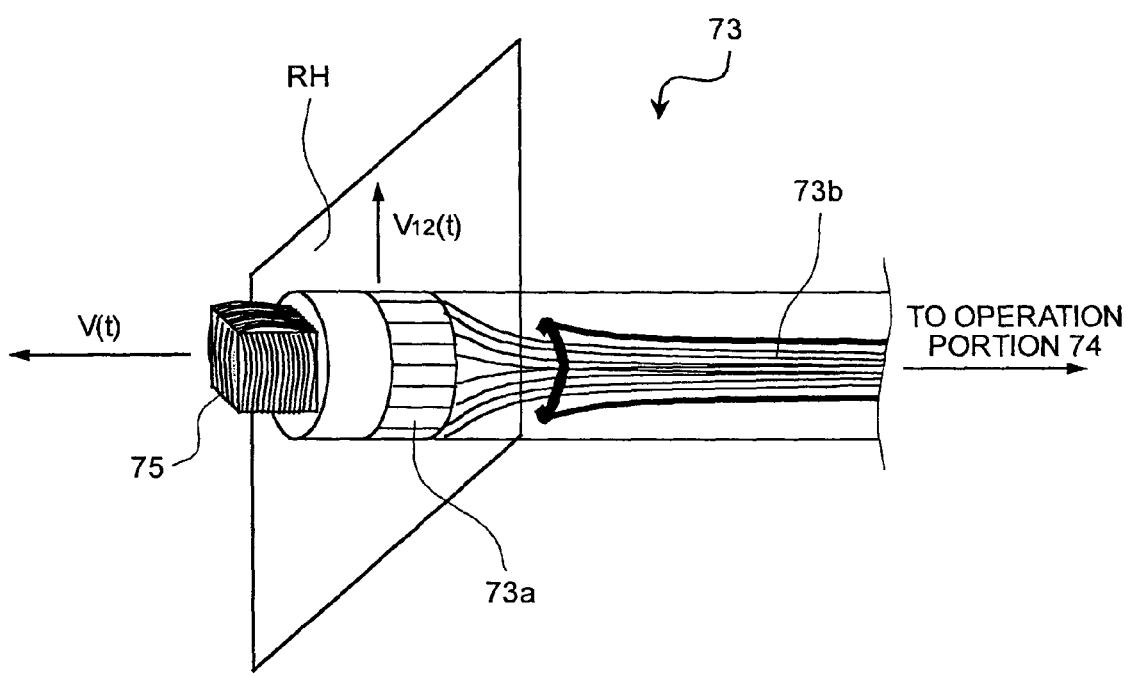
FIG. 25 is a schematic diagram illustrating a structure of a distal end of an electronic radial scan type probe.

FIG. 25 is a schematic diagram illustrating an exemplary structure of a distal end of the insertion portion 73 of the probe 72. In FIGS. 24 and 25, the probe 72 is implemented with an electronic radial scanning ultrasonic endoscope. As described above, the probe 72 includes the insertion portion 73 to be inserted inside the subject body and the operation portion 74. At the distal end of the insertion portion 73, the ultrasonic transducer group 73a and the transmission coil 75 are provided. The ultrasonic transducer group 73a consists of plural ultrasonic transducers. The ultrasonic transducer is a small piece cut into a strip-like shape, and the ultrasonic transducers are arranged around a central axis, which runs along the direction of insertion axis into the subject body, in a circle, for example over the entire circumference of 360°. Each ultrasonic transducer forming the ultrasonic transducer group 73a is electrically connected to the ultrasonic observation device 5 through the signal line 73b and the operation portion 74.

The operation portion 74, substantially similarly to the operation portion 4 described above, has a function of bending the distal end of the insertion portion 73 where the ultrasonic transducer group 73a and the transmission coil 75 are arranged in response to the manipulation by the operator. Further, the operation portion 74 makes the ultrasonic transducer group 73a and the ultrasonic observation device 5 electrically connected with each other when the operator turns a power switch in the operation portion 74 on.

The transmission coil 75 has a structure where the two coils are integrally arranged, so that the coil axes of the respective coils run orthogonal with each other. Each of the two coils is electrically connected to the position data calculating device 6. Further, the transmission coil 75 is arranged at an end of the ultrasonic transducer group 73a near the distal end side of the insertion portion 73 as shown in FIG. 25. Here, it is desirable that the transmission coil 75 be arranged so that the outer shape thereof does not extend over the sectional plane of the ultrasonic transducer group 73a. Thus, the diameter of the insertion portion 73 can be made thinner.

In the transmission coil 75, one of the two orthogonal coils is arranged so that the direction of the coil axis thereof corresponds with the direction of insertion axis of the insertion portion 73 inside the subject body, whereas another of the two orthogonal coils is arranged so that the direction of the coil axis thereof corresponds with a direction of twelve o'clock of a scanning plane of the electronic radial scan by the ultrasonic transducer group 73a, i.e., a radial scanning plane RH shown in FIG. 25. Hence, in the transmission coil 75, substantially similarly to the transmission coil 7 described above, the direction of the coil axis of one coil corresponds to the direction of normal line of the two-dimensional image data, i.e., the direction vector V(t) described above, and the direction of the coil axis of another coil corresponds to the direction of twelve o'clock of the two-dimensional image data, i.e., the direction vector $V_{12}(t)$ described above.

Here, when start command information for the electronic radial scan is input from the input device 11, the controlling unit 53 commands the ultrasonic observation device 5 to start the electronic radial scan by sending control signals to the ultrasonic observation device 5 based on the start command information as input. The ultrasonic observation device 5 transmits exciting signals to each of the ultrasonic transducer in the ultrasonic transducer group 73a via the operation portion 74 and the signal line 73b based on the control signals received from the controlling unit 53, thereby applying pulsing voltage of approximately 100 V to each ultrasonic transducer in the ultrasonic transducer group 73a. Here, the ultrasonic observation apparatus 5 delays each exciting signal to be transmitted to the ultrasonic transducers in the ultrasonic transducer group 73a, and controls the transmission of the exciting signals so that the transmitted exciting signals reach the respective ultrasonic transducers in the ultrasonic transducer group 73a at different timings. Thus, when the ultrasound irradiated from the ultrasonic transducers in the ultrasonic transducer group 73a is combined together inside the subject body, they form one ultrasound beam.

Each ultrasonic transducer in the ultrasonic transducer group 73a, on receiving the exciting signals from the ultrasonic observation device 5, sequentially converts the exciting signal to the ultrasound which is a compressional wave in media, and irradiates the resulting ultrasound. The ultrasound is sequentially emitted from the ultrasonic transducer group 73a, and the ultrasonic transducer group 73a sequentially irradiates the interior of the subject from the probe 72 with the ultrasound beam as described above. Thereafter, the reflective wave of the ultrasound beam from the interior of the subject body travels through the path of the ultrasound irradiation in a reverse direction, and sequentially returns to the ultrasonic transducer. Thus, the ultrasonic transducer group 73a achieves one electronic radial scan. Then, each ultrasonic transducer of the ultrasonic transducer group 73a, on receiving the reflective wave, sequentially converts the reflective wave into the scan signals described above, and at the same time, sequentially transmits the scan signals to the ultrasonic observation device 5 through the signal path of the above described exciting signal via the signal cable 73b and the operation portion 74, in reverse direction.

Here, when the ultrasonic transducer group 73a sequentially emits the ultrasound beam described above to perform the electronic radial scan within the radial scanning plane RH, the ultrasonic observation device 5 transmits the exciting signal first to one of the ultrasonic transducers previously set as the ultrasonic transducer at an original position, then, sequentially to the ultrasonic transducer adjacent to the first ultrasonic transducer in a predetermined direction. Thus, the ultrasonic transducer group 73a can sequentially irradiates the radial scan plane RH with the ultrasound beam in a clockwise direction or in a counterclockwise direction starting from the ultrasonic transducer at the original position as a starting point of the scan.

Further, the ultrasonic observation device 5 is previously set with respect to which of the ultrasonic transducers in the ultrasonic transducer group 73a is the ultrasonic transducer that irradiates the radial scan plane RH with the ultrasound beam in a twelve o'clock direction. Therefore, when the ultrasonic observation device 5 transmits the exciting signals to the ultrasonic transducer of the twelve o'clock direction, the ultrasonic observation device 5 receives the scan signal from the ultrasonic transducer as a scan signal corresponding to the ultrasonic scanning in the twelve o'clock direction on the radial scan plane RH, and determines the twelve o'clock direction of the two-dimensional image data described above.

On the other hand, the position data calculating device 6 supplies electric currents to the marker coil 8 and the plate 9 as described above, and further supplies electric currents to the transmission coil 75. Each of the two coils constituting the transmission coil 75 outputs an alternating magnetic field with different frequency based on the electric currents supplied from the position data calculating device 6. The receiver coil 10 detects, in addition to the alternating magnetic field from the marker coil 8 and the alternating magnetic field from the plate 9 described above, the alternating magnetic field output from each coil of the transmission coil 75, converts the detected alternating magnetic field into the position detection signals described above, and transmits the position detection signals to the position data calculating device 6. The position data calculating device 6 obtains the position detection signal which is based on each of the alternating magnetic field from the two coils in the transmission coil 75, in addition to the position detection signal from the marker coil 8 described above and the position detection signal from the plate 9 as described above by separating the position detection signals input from the receiver coil 10 with respect to each frequency.

Thereafter, the position data calculating device 6 calculates, in addition to the position data of the marker coil 8 described above and the position data of the plate 9, position data of each of the two coils of the transmission coil 75, i.e., the coordinate data concerning the central position of the two-dimensional image data, the coordinate data concerning the direction of normal line, and the coordinate data concerning the direction of twelve o'clock, based on the obtained position detection signals, and transmits the calculated position data to the controlling unit 53.

In the seventh embodiment of the present invention, the ultrasonic diagnosis apparatus which has the structure and the function to perform the electronic radial scan in addition to substantially the same structure and the function as those of the fifth embodiment described above is illustrated. The present invention, however, is not limited thereto. The ultrasonic diagnosis apparatus having substantially the same structure and the function as those of one of the third and the fourth embodiments may be further provided with the structure and the function to perform the electronic radial scan. In other words, the image searching unit 53a may not be provided. Further, the ultrasonic diagnosis apparatus having substantially the same structure and the function as those of one of the first and the second embodiments described above may be further provided with the structure and the function to perform the electronic radial scan. In other words, the rotation processing unit 33a and the image searching unit 53a may not be provided. Still further, the ultrasonic diagnosis apparatus having substantially the same structure and the function as those of the sixth embodiment described above may be further provided with the structure and the function to perform the electronic radial scan.

Further, in the seventh embodiment of the present invention, the plural ultrasonic transducers are arranged around the central axis, which is arranged along the direction of the insertion axis, in a circle, i.e., over the entire circumference of 360° as the ultrasonic transducer group 73a. The present invention, however, is not limited to such arrangement. In place of the ultrasonic transducer 73a, an ultrasonic transducer group including plural ultrasonic transducers arranged around the central axis, which is arranged along the direction of the insertion axis, like a fan, for example over an angle of 180° or 270° may be employed.

Further, in the seventh embodiment of the present invention, an electronic radial scanning type ultrasonic endoscope is employed as the probe 72. The present invention, however, is not limited thereto. An electronic radial scanning probe which does not include an optical system may be employed in place of the probe 72.

As described above, the seventh embodiment of the present invention has the structure to perform the electronic radial scan in addition to substantially the same structure and the function as those of one of the first to the sixth embodiments described above. Therefore, angular deviance of the twelve o'clock direction in the two-dimensional ultrasound images is not caused by the contortion of the flexible shaft, and the twelve o'clock direction of the two-dimensional image data determined by the electronic radial scan can be made to securely match with the twelve o'clock direction of the two-dimensional image data determined based on the alternating magnetic field from the transmission coil. Thus, in addition to the enjoyment of the effect and the advantage of one of the fist to the sixth embodiments described above, the ultrasonic diagnosis apparatus which is capable of securely outputting and displaying the two-dimensional ultrasound image inside the subject body and the guide image anatomically corresponding to the two-dimensional ultrasound image can be realized.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic diagnosis apparatus which performs a scan of an interior of a subject to obtain two-dimensional image data of the interior, creates and outputs a two-dimensional ultrasound image of the interior based on the two-dimensional image data, and detects a posit ion and an orientation of a scanning plane of the scan according to which the two-dimensional image data is obtained, the ultrasonic diagnosis apparatus comprising:

an image processing controlling unit that creates a guide image which corresponds to an anatomical position and orientation of the two-dimensional ultrasound image based on anatomical image data, which is previously stored as anatomical image data of a human body, and the position and the orientation of the scanning plane;

a display unit that outputs and displays various types of images including the guide image and the two-dimensional ultrasound image so that plural images are simultaneously output and displayed; and a sample point detecting unit that detects, from the subject, positions of sample points that correspond to feature points on the anatomical image data, wherein the image processing controlling unit sets a nonorthogonal feature point three-axis coordinate system on the anatomical image data based on the feature points, sets in a space where the subject is in a nonorthogonal sample point three-axis coordinate system that anatomically corresponds to the feature point three-axis coordinate system based on the sample points, converts the detected position and orientation of the scanning plane into a position and an orientation on the sample point three-axis coordinate system, converts the position and the orientation obtained as a result of conversion into a position and an orientation on the feature point three-axis coordinate system, and creates the guide image based on the position and the orientation on the feature point three-axis coordinate system obtained as a result of conversion.

2. The ultrasonic diagnosis apparatus according to claim 1, further comprising an input unit that designates and inputs the feature points, wherein the anatomical image data includes plural pieces of slice image data each corresponding to a slice image taken along a transverse section that is vertical to a body axis of the human body, and the input unit designates and inputs the feature points on the slice image.

3. The ultrasonic diagnosis apparatus according to claim 2, wherein the image processing controlling unit calculates a sectional plane of the anatomical image data based on the feature points, the sample points, and the position and orientation of the scanning plane, creates sectional image data corresponding to a sectional image on the sectional plane based on the anatomical image data, and creates the guide image based on the sectional plane and the sectional image data.

4. The ultrasonic diagnosis apparatus according to claim 3, wherein the image processing controlling unit interpolates on intersecting lines between the sectional plane and the plural pieces of slice image data to create the sectional image data.

5. The ultrasonic diagnosis apparatus according to claim 3, wherein the anatomical image data is anatomical three-dimensional image data of the human body, the input unit designates a cut position of the three-dimensional image data, the image processing controlling unit creates the sectional image data by cutting the three-dimensional image data along the cut position, and the input unit directly designates and input the feature point on the sectional image.

6. The ultrasonic diagnosis apparatus according to claim 2, wherein the input unit inputs at least four of the feature points, and the sample point detecting unit detects at least four sample points each anatomically corresponding to the at least four feature points, respectively.

7. The ultrasonic diagnosis apparatus according to claim 6, wherein the sample point detecting unit includes a reference sample point detecting unit that is arranged on a body surface of the subject and that detects an orientation of itself, and the image processing controlling unit corrects, when the subject changes a posture, each of coordinates of the four samples points based on the positions of the four sample points and the orientation of the reference sample point detecting unit.

8. The ultrasonic diagnosis apparatus according to claim 2, further comprising a probe that is inserted inside a body cavity, wherein the sample point detecting unit is arranged at a distal end of the probe to detect, when the distal end is in contact with the subject, the sample points from the inside of the body cavity of the subject.

9. The ultrasonic diagnosis apparatus according to claim 8, wherein the probe has on its distal end an optical observation unit which obtains an optical image inside the body cavity of the subject, the display unit displays the optical image obtained by the optical observation unit, and the sample point detecting unit detects the sample points from inside the body cavity of the subject while the display unit displays the optical image and when the distal end is in contact with the subject.

10. The ultrasonic diagnosis apparatus according to claim 2, wherein the sample points anatomically correspond to four of an ensiform cartilage, a right end of pelvis, a pylorus, a duodenal papilla, and a cardiac orifice.

11. The ultrasonic diagnosis apparatus according to claim 2, wherein the input unit inputs a rotation angle of the two dimensional ultrasound image or the guide image around an image center as a rotation center, and the image processing controlling unit sequentially creates and outputs a two-dimensional ultrasound image without changing a direction of a normal line of the two-dimensional ultrasound image and setting the rotation angle at a direction perpendicular to the direction of the normal line, or sequentially creates and outputs a guide image without changing a direction of a normal line of the guide image and setting the rotation angle at a direction perpendicular to the direction of the normal line.

12. The ultrasonic diagnosis apparatus according to claim 11, wherein the image processing controlling unit sequentially creates and outputs a guide image without changing a direction of a normal line of the guide image and setting the rotation angle in a direction perpendicular to the direction of the normal line, and sequentially creates and outputs a two-dimensional ultrasound image without changing a direction of a normal line of the two-dimensional ultrasound image and setting the rotation angle at a direction perpendicular to the direction of the normal line.

13. The ultrasonic diagnosis apparatus according to claim 11, wherein the input unit inputs the rotation angle which is variable according to an amount of input of the input unit.

14. The ultrasonic diagnosis apparatus according to claim 11, further comprising a position detecting unit that detects a central position and a direction of a normal line of a scanning plane of the scan which is a radial scan, the position detecting unit having previously set default orientation data concerning a direction perpendicular to the direction of the normal line, wherein the image processing controlling unit makes the central position detected and the direction of the normal line detected match with the orientation of the two-dimensional ultrasound image and the orientation of the guide image according to the default orientation data based on the rotation angle.

15. The ultrasonic diagnosis apparatus according to claim 2, wherein the input unit further inputs identification information to identify the two-dimensional ultrasound image, and the image processing controlling unit associates the identification information with the two-dimensional ultrasound image and the guide image for every input identification information, searches for a two-dimensional ultrasound image based on the input identification information, and makes the display unit display a found two-dimensional ultrasound image and a guide image associated with the found two-dimensional ultrasound image.

16. The ultrasonic diagnosis apparatus according to claim 1, further comprising:

an image creating unit that creates the anatomical image data using a desired human body; and a communicating unit that transmits the anatomical image data from the image creating unit to the image processing controlling unit.

17. The ultrasonic diagnosis apparatus according to claim 16, wherein the image creating unit includes one of an X-ray CT apparatus, an MRI apparatus, and a PET apparatus.

18. The ultrasonic diagnosis apparatus according to claim 1, wherein the anatomical image data is previously classified with respect to each region.

19. The ultrasonic diagnosis apparatus according to claim 18, wherein the anatomical image data is previously colored and classified with respect to each region.

20. The ultrasonic diagnosis apparatus according to claim 1, further comprising an inserted shape detecting unit that detects an inserted shape of an insertion portion, which is insertable inside the body, of the probe that performs the scan, wherein the image processing controlling unit makes the display unit display an inserted shape image which indicates the inserted shape together with the two-dimensional ultrasound image and the guide image.

21. The ultrasonic diagnosis apparatus according to claim 1, further comprising an electronic radial scanning type probe that includes plural ultrasonic transducers arranged in a circle, the ultrasonic transducers transmitting and receiving ultrasound in a predetermined order inside the body, to perform the scan.

* * * * *